United States Patent
Butler et al.

(10) Patent No.: US 9,604,981 B2
(45) Date of Patent: Mar. 28, 2017

(54) IP RECEPTOR AGONIST HETEROCYCLIC COMPOUNDS

(71) Applicant: Novartis AG, Basel (CH)

(72) Inventors: Rebecca Butler, Horsham (GB); Catherine Leblanc, Basel (CH); Stephen Carl McKeown, Horsham (GB); Steven John Charlton, Horsham (GB)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/767,500

(22) PCT Filed: Feb. 11, 2014

(86) PCT No.: PCT/IB2014/058905
§ 371 (c)(1),
(2) Date: Aug. 12, 2015

(87) PCT Pub. No.: WO2014/125413
PCT Pub. Date: Aug. 21, 2014

(65) Prior Publication Data
US 2015/0376183 A1    Dec. 31, 2015

Related U.S. Application Data

(60) Provisional application No. 61/764,308, filed on Feb. 13, 2013.

(51) Int. Cl.
C07D 471/04 (2006.01)
A61K 31/4375 (2006.01)

(52) U.S. Cl.
CPC ........ C07D 471/04 (2013.01); A61K 31/4375 (2013.01)

(58) Field of Classification Search
None
See application file for complete search history.

(56) References Cited

U.S. PATENT DOCUMENTS

| | | | |
|---|---|---|---|
| 3,960,876 A | 6/1976 | Curran | |
| 7,119,207 B2 | 10/2006 | O'Neill et al. | |
| 2003/0087925 A1 | 5/2003 | O'Neill et al. | |
| 2008/0027039 A1 | 1/2008 | Arakawa et al. | |
| 2008/0064871 A1 | 3/2008 | Hirata et al. | |
| 2008/0305169 A1 | 12/2008 | Miki et al. | |
| 2009/0005434 A1 | 1/2009 | Olesen et al. | |
| 2010/0280041 A1 | 11/2010 | Chen et al. | |
| 2013/0184282 A1 | 7/2013 | Adcock et al. | |

FOREIGN PATENT DOCUMENTS

| | | |
|---|---|---|
| EP | 558062 | 9/1993 |
| EP | 753528 | 1/1997 |
| EP | 0976732 | 2/2000 |
| EP | 1400518 | 3/2004 |
| EP | 1475368 | 11/2004 |
| EP | 1820515 | 8/2007 |
| JP | 2004/501072 | 1/2004 |
| WO | 92/020642 | 11/1992 |
| WO | 95/09872 | 4/1995 |
| WO | 96/35713 | 11/1996 |
| WO | 98/18796 | 5/1998 |
| WO | 00/33838 | 6/2000 |
| WO | 00/78724 | 12/2000 |
| WO | 01/17959 | 3/2001 |
| WO | 20010119788 | 3/2001 |
| WO | 01/34602 | 5/2001 |
| WO | 20011049675 | 7/2001 |
| WO | 01/58441 | 8/2001 |
| WO | 01/77100 | 10/2001 |
| WO | 03/039544 | 5/2003 |
| WO | 2004/083207 | 9/2004 |
| WO | 2004/099159 | 11/2004 |
| WO | 2005/020926 | 3/2005 |
| WO | 2005/051386 | 6/2005 |
| WO | 2005/063766 | 7/2005 |
| WO | 2006/122156 | 2/2007 |
| WO | 2007/017096 | 3/2007 |

(Continued)

OTHER PUBLICATIONS

Neipp et al. Tetrahedron Letters (1997), 38(43), pp. 7499-7502.*
Lahue et al, Journal of Organic Chemistry (2004), 69(21), pp. 7171-7182.*
Woo et al., Tetrahedron (2007), 63(25), pp. 5649-5655.*
Driscoll et al., "Medical therapy for pulmonary arterial hypertension", Expert Opinion in Pharmacotherapy; 9(1):65-81 (2008).
Paetzel et al., Journal of Heterocyclic Chemistry 29(5): 1067-1068, 1992.
Cosmao et al., Canadian Journal of Chemistry 60(22):2785-2791, 1982.
Armand et al., Canadian Journal of Chemistry 56(13):1804-1816, 1978.

(Continued)

Primary Examiner — Brian J Davis
(74) Attorney, Agent, or Firm — Shawn Britt

(57) ABSTRACT

The present invention provides heterocyclic derivatives of formula (Ia) which activate the IP receptor. Activating the IP receptor signaling pathway is useful to treat many forms of PAH, pulmonary fibrosis and exert beneficial effects in fibrotic conditions of various organs in animal models and in patients. Pharmaceutical compositions comprising such derivatives are also encompassed.

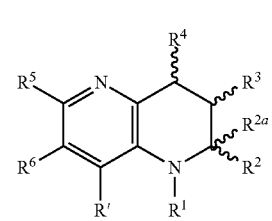

9 Claims, No Drawings

(56) References Cited

FOREIGN PATENT DOCUMENTS

| WO | 2007/024944 | | 3/2007 |
| WO | 2007/088019 | | 8/2007 |
| WO | 2007/088019 | A1 | 8/2007 |
| WO | 2008/154221 | | 12/2008 |
| WO | 2010/008864 | | 1/2010 |
| WO | 2010/009208 | | 1/2010 |
| WO | 2010/020366 | | 2/2010 |
| WO | 2010/088177 | A1 | 8/2010 |
| WO | 2011/075628 | A1 | 6/2011 |
| WO | 2011/096461 | A1 | 8/2011 |
| WO | 2011/111880 | | 9/2011 |
| WO | 2012/007539 | | 1/2012 |
| WO | 2013/105057 | | 7/2013 |
| WO | 2013/105058 | | 7/2013 |
| WO | 2013/105061 | | 7/2013 |
| WO | 2013/105063 | | 7/2013 |
| WO | 2013/105065 | | 7/2013 |
| WO | 2013/105066 | | 7/2013 |

OTHER PUBLICATIONS

Armand et al., Compte Rendus des Seances de l'Academie des Sciences, Serie C: Sciences Chimiques 281(13):547-549, 1975.
Vinot et al., Bulletin de la Societe Chimique de France (1973), (vol. 11, Pt. 2), 3100-3102.
E.Kelly et al., NaF and Guanine Nucleotides Modulate Adenylate Cyclase Activity in NG108-15 Cells by Interacting with Both G8 and Gt Br J Pharmacal. 100(2):223-230 Jun. 1990.
Kuwano et al., "2-(4-[(5,6-Diphenylpyrazin-2-yl)(isopropyl)amino]butoxyl-N-(methylsulfonyl)acetamide (NS-304), an Orally Available and Long-Acting Prostacyclin Receptro Agonist Prodrug" Journal QfPharmacology and Experimental Therapeutics, 322(3):1181-1188, 2007.
Driscoll et al., "Medical Therapy for Pulmonary Arterial Hypertension" Expert Opinion on Pharmacotherapy, 9(1):65-81.
International Search Report and Written Opinion for International Application No. PCT/IB2014/058905 mailed Jun. 23, 2014. 12 pages.

* cited by examiner

IP RECEPTOR AGONIST HETEROCYCLIC COMPOUNDS

This application is a U.S. National Phase filing of International Application No. PCT/IB2014/058905 filed Feb. 11, 2014, which claims priority to U.S. Provisional Application No. 61/764,308 filed Feb. 13, 2013.

BACKGROUND OF THE INVENTION

Prostacyclin (or PGI2) is a member of the family of lipid molecules known as eicosanoids. It is a potent vasodilator, antiproliferative, anti-thrombotic agent that mediates its effects as an agonist of the IP receptor. The IP receptor is a G-protein coupled receptor that, upon activation by prostacyclin, stimulates the formation of cyclic adenosine monophosphate (cAMP). Prostacyclin counteracts the vasoconstrictor and pro-thrombotic activity of endothelin.

Pulmonary arterial hypertension (PAH) is a life-threatening disease characterized by a progressive pulmonary vasculopathy leading to right ventricular hypertrophy. Exogenous administration of an agonist of the IP receptor has become an important strategy in the treatment of PAH. (See, e.g., Tuder et al., Am. J. Respir. Crit. Care. Med., 1999, 159: 1925-1932; Humbert et al, J. Am. Coll. Cardiol., 2004, 43:13S-24S; Rosenzweig, Expert Opin. Emerging Drugs, 2006, 11:609-619; McLaughlin et al, Circulation, 2006, 114:1417-1431; Rosenkranz, Clin. Res. Cardiol., 2007, 96:527-541; Driscoll et al, Expert Opin. Pharmacother., 2008, 9:65-81.).

The prostacyclin analogue epoprostenol (flolan) is at least as effective as transplantation in terms of survival. Despite this, it is not used as frontline therapy due to significant tolerability, convenience and cost issues. Instead, patients with PAH are often treated first with either endothelin receptor antagonists (e.g. bosentan) and/or PDE5 inhibitors (e.g. sildenafil), which are better tolerated but can have limited efficacy. Prostacyclin analogues are used mainly as add-on treatment as severity of the disease progresses and tolerability and convenience become less of an issue.

Two key issues prevent current prostacyclin analogues being used as frontline therapy in PAH. Firstly, they are very unstable with an extremely short half-life, meaning they must be constantly infused via an in-dwelling intra venous (i.v.) catheter that is both inconvenient for the patient and also associated with a significant risk of infection and sepsis. Secondly, they are associated with significant side effects including nausea, jaw pain, headache and other side effects associated with systemic hypotension.

One solution to these issues is iloprost, which is available as a nebulised formulation that has reduced tolerability issues, but the short half life results in a 6-9 times daily dosing regime. More recently, researchers made efforts to generate stable, orally available IP receptor agonists. These ligands would improve patient convenience and compliance, but high levels of systemic drug is required to achieve pharmacodynamic effects in the lung; thus, possibly generating similar side effects to those observed with i.v. flolan.

The present invention describes stable, highly selective IP receptor agonists that are suitable for oral and inhaled delivery. The present invention offers a significant improvement over existing prostacyclin analogues and enables their use in less-severe patients. In addition, long term activation of the IP receptor has been shown to reverse remodeling associated with PAH; therefore, earlier intervention with the present invention may have significant effects on disease progression and potentially may show reversal.

In addition, pharmaceutical research has considerable interest in developing IP receptor agonists for the treatment of pulmonary fibrosis. IP deficient mice have been shown to be more susceptible to bleomycin-induced lung fibrosis than wild-type animals (Lovgren A K at al. (2006) *Am J Physiol Lung Cell Mol Physiol.* 291:L144-56), and the IP receptor agonist iloprost increases survival in bleomycin-treated mice (Zhu et al (2010) Respir Res. 11(1):34).

Furthermore, IP receptor signaling has been shown to exert beneficial effects in fibrotic conditions of various organs in animal models and in patients. Benefits of IP receptor agonist were shown for fibrosis of the heart, lung, skin, pancreas and liver, and in systemic sclerosis. (Gayraud M (2007) *Joint Bone Spine.* 74(1):e1-8; Hirata Y et al (2009) *Biomed Pharmacother.* 63(10):781-6; Kaneshige T et al (2007) *J Vet Med Sci.* 69(12):1271-6; Sahsivar M O et al (2009) *Shock* 32(5):498-502; Sato N et al (2010) *Diabetes* 59(4):1092-100; Shouval D S et al (2008) *Clin Exp Rheumatol.* 26(3 Suppl 49):S105-7; Spargias K et al (2009) *Circulation.* 120(18):1793-9; Stratton R et al (2001) *J Clin Invest.* 108(2):241-50; Takenaka M et al (2009) Prostaglandins Leukot Essent Fatty Acids. 80(5-6):263-7; Watanabe M et al (2009) *Am J Nephrol.* 30(1):1-11; Yano T et al (2005) *Am J Pathol.* 166(5):1333-42; Zardi E M et al (2007) *Expert Opin Biol Ther.* 7(6):785-90; Zardi E M et al (2006) *In Vivo* 20(3):377-80; Rehberger P et al (2009) *Acta Derm Venereol.* 89(3):245-9). Fibrotic conditions can occur in most organs secondary to chronic inflammation indications throughout the body and are likely to share common causes. Therefore, antifibrotic agents such as IP receptor agonists of the present invention are of potential benefit in all indications that are associated with fibrotic tissue remodeling.

There is considerable interest in developing agonists of the IP receptor for use in the treatment of other diseases, such as atherothrombosis, preeclampsia. It is highly desirable to develop a stable, inhaled agonists of the IP receptor, which may lead to improved management of PAH.

WO2012/007539, PCT/IB2013/050271, PCT/IB2013/050273, PCT/IB2013/050277, PCT/IB2013/050280, PCT/IB2013/050282 (all Novartis) describe IP receptor agonist heterocyclic compounds.

The invention pertains to the compounds, methods for using them, and uses thereof as described herein.

Embodiment 1

A compound represented by Formula I

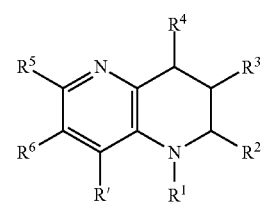

and a pharmaceutically acceptable salt thereof, wherein
R' is H, $C_1$-$C_8$ alkyl optionally substituted by one or more halogen atoms;
$R^1$ is H, $C_1$-$C_8$ alkyl optionally substituted by one or more halogen atoms, $C_1$-$C_4$ alkyl, OH, OR', —$NR^{19}R^{21}$, CN or $C_3$-$C_7$ cycloalkyl; or
$R^1$ is —X—Y; or
$R^1$ is —W—$R^7$—X—Y; or R$^1$ is —S(O)$_2$—W—X—Y; or
R$^1$ is —S(O)$_2$—W—R$^7$—X—Y;
R$^2$ is H, C$_1$-C$_8$ alkyl optionally substituted by one or more halogen atoms, C$_1$-C$_4$ alkyl, OH, OR', —NR$^{19}$R$^{21}$, CN or C$_3$-C$_7$ cycloalkyl; or
R$^2$ is —X—Y; or
R$^2$ is —W—R$^7$—X—Y; or
R$^2$ is —S(O)$_2$—W—X—Y;
R$^2$ is —S(O)$_2$—W—R$^7$—X—Y;
wherein either R$^1$ or R$^2$ must be —X—Y, —W—R$^7$—X—Y, —S(O)$_2$—W—X—Y; or —S(O)$_2$—W—R$^7$—X—Y;
R$^3$ is H, C$_1$-C$_8$ alkyl optionally substituted by one or more halogen atoms, C$_1$-C$_4$ alkoxy, OH, —NR$^{19}$R$^{21}$, CN or C$_3$-C$_7$ cycloalkyl;
R$^4$ is H, C$_1$-C$_8$ alkyl optionally substituted by one or more halogen atoms, C$_1$-C$_4$ alkoxy, OH, —NR$^{19}$R$^{21}$, CN or C$_3$-C$_7$ cycloalkyl;
R$^5$ is C$_1$-C$_8$ alkyl optionally substituted by one or more halogen atoms, C$_1$-C$_4$ alkyl, OH, OR', —NR$^{19}$R$^{21}$, CN or C$_3$-C$_7$ cycloalkyl; C$_1$-C$_8$ alkoxy optionally substituted by one or more halogen atoms; C$_6$-C$_{14}$ aryl; —(C$_0$-C$_4$ alkyl)-4 to 14 membered heteroaryl, or —(C$_0$-C$_4$ alkyl)-3 to 14 membered heterocyclyl wherein the heteroaryl and heterocyclyl contain at least one heteroatom selected from N, O and S, wherein the aryl, heteroaryl and heterocyclyl are each optionally substituted by one or more Z substituents;
R$^6$ is C$_6$-C$_{14}$ aryl; —(C$_0$-C$_4$ alkyl)-4 to 14 membered heteroaryl, —(C$_0$-C$_4$ alkyl)-3 to 14 membered heterocyclyl wherein the heteroaryl and heterocyclyl contain at least one heteroatom selected from N, O and S, wherein the aryl, heteroaryl and heterocyclyl are each optionally substituted by one or more Z substituents;
W is C$_1$-C$_8$ alkylene optionally substituted by hydroxy, halogens or C$_1$-C$_4$ alkyl;
X is C$_1$-C$_8$ alkylene optionally substituted by hydroxy, halogens or C$_1$-C$_4$ alkyl;
Y is carboxy, alkoxycarbonyl, tetrazolyl, carbamoyl, monoalkylcarbamoyl, dialkylcarbamoyl, or —CONH—S(O)$_q$—R$^x$, wherein R$^x$ is —C$_1$-C$_4$ alkyl or —NR$^{19}$R$^{21}$;
q is 0, 1 or 2;
R$^7$ is a divalent moiety represented by —C$_6$-C$_{14}$ aryl-D-; -3 to 14 membered heterocyclyl-D-, wherein the heterocyclyl contains at least one heteroatom selected from N, O and S, wherein D is O, S, NH or not present;
Z is independently OH, aryl, O-aryl, benzyl, O-benzyl, C$_1$-C$_6$ alkyl optionally substituted by one or more OH groups or NH$_2$ groups, C$_1$-C$_6$ alkyl optionally substituted by one or more halogen atoms, C$_1$-C$_6$ alkoxy optionally substituted by one or more OH groups, C$_1$-C$_6$ alkoxy optionally substituted by one or more halogen, C$_1$-C$_6$ alkoxy optionally substituted by C$_1$-C$_4$ alkoxy, NR$^{18}$(SO$_2$)R$^{21}$, (SO$_2$)NR$^{19}$R$^{21}$, (SO$_2$)R$^{21}$, NR$^{18}$C(O)R$^{21}$, C(O)NR$^{19}$R$^{21}$, C(O)NR$^{19}$R$^{21}$, NR$^{18}$C(O)OR$^{19}$, NR$^{19}$R$^{21}$, C(O)OR$^{19}$, C(O)R$^{19}$, SR$^{19}$, OR$^{19}$, oxo, CN, NO$_2$, halogen or a 3 to 14 membered heterocyclyl, wherein the heterocyclyl contains at least one heteroatom selected from N, O and S;
R$^{18}$ is independently H or C$_1$-C$_6$ alkyl;
R$^{19}$ and R$^{21}$ are each independently H; C$_1$-C$_8$ alkyl; C$_3$-C$_8$ cycloalkyl; C$_1$-C$_4$ alkoxy-C$_1$-C$_4$ alkyl; (C$_0$-C$_4$ alkyl)-aryl optionally substituted by one or more groups selected from C$_1$-C$_6$ alkyl, C$_1$-C$_6$ alkoxy and halogen; (C$_0$-C$_4$ alkyl)- 3- to 14-membered heterocyclyl, the heterocyclyl including one or more heteroatoms selected from N, O and S, optionally substituted by one or more groups selected from halogen, oxo, C$_1$-C$_6$ alkyl and C(O)C$_1$-C$_6$ alkyl; (C$_0$-C$_4$ alkyl)-O-aryl optionally substituted by one or more groups selected from C$_1$-C$_6$ alkyl, C$_1$-C$_6$ alkoxy and halogen; and (C$_0$-C$_4$ alkyl)- O-3- to 14-membered heterocyclyl, the heterocyclyl including one or more heteroatoms selected from N, O and S, optionally substituted by one or more groups selected from halogen, C$_1$-C$_6$ alkyl or C(O)C$_1$-C$_6$ alkyl; wherein the alkyl groups are optionally substituted by one or more halogen atoms, C$_1$-C$_4$ alkoxy, C(O)NH$_2$, C(O)NHC$_1$-C$_6$ alkyl or C(O)N(C$_1$-C$_6$ alkyl)$_2$; or
R$^{19}$ and R$^{21}$ together with the nitrogen atom to which they attached form a 5- to 10-membered heterocyclyl, the heterocyclyl including one or more further heteroatoms selected from N, O and S, the heterocyclyl being optionally substituted by one or more substituents selected from OH; halogen; aryl; 5- to 10-membered heterocyclyl including one or more heteroatoms selected from N, O and S; S(O)$_2$-aryl; S(O)$_2$—C$_1$-C$_6$ alkyl; C$_1$-C$_6$ alkyl optionally substituted by one or more halogen atoms; C$_1$-C$_6$ alkoxy optionally substituted by one or more OH groups or C$_1$-C$_4$ alkoxy; and C(O)OC$_1$-C$_6$ alkyl, wherein the aryl and heterocyclyl substituent groups are themselves optionally substituted by C$_1$-C$_6$ alkyl, C$_1$-C$_6$ haloalkyl or C$_1$-C$_6$ alkoxy.

Embodiment 2

A compound represented by Formula Ia

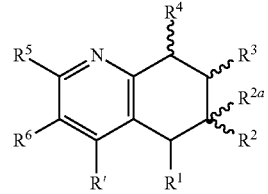

Ia or a pharmaceutically acceptable salt thereof, wherein
R' is H, C$_1$-C$_8$ alkyl optionally substituted by one or more halogen atoms;
R$^1$ is H, C$_1$-C$_8$ alkyl optionally substituted by one or more halogen atoms, C$_1$-C$_4$ alkyl, OH, OR', —NR$^{19}$R$^{21}$, CN or C$_3$-C$_7$ cycloalkyl; or
R$^1$ is —X—Y; or
R$^1$ is —W—R$^7$—X—Y; or
R$^1$ is —S(O)$_2$—W—X—Y; or
R$^1$ is —S(O)$_2$—W—R$^7$—X—Y;
R$^2$ is H, C$_1$-C$_8$ alkyl optionally substituted by one or more halogen atoms, C$_1$-C$_4$ alkyl, OH, OR', —NR$^{19}$R$^{21}$, CN or C$_3$-C$_7$ cycloalkyl; or
R$^2$ is —X—Y; or
R$^2$ is —W—R$^7$—X—Y; or
R$^2$ is —S(O)$_2$—W—X—Y;
R$^2$ is —S(O)$_2$—W—R$^7$—X—Y;
wherein either R$^1$ or R$^2$ is —X—Y, —W—R$^7$—X—Y, —S(O)$_2$—W—X—Y; or —S(O)$_2$—W—R$^7$—X—Y;
R$^{2a}$ is hydrogen;
R$^2$ and R$^{2a}$ taken together are oxo;
R$^3$ is H, C$_1$-C$_4$ alkoxy, OH, —NR$^{19}$R$^{21}$, CN, halogen, C$_3$-C$_7$ cycloalkyl or C$_1$-C$_8$ alkyl optionally substituted by one or more halogen atoms;
R$^4$ is H, C$_1$-C$_4$ alkoxy, OH, —NR$^{19}$R$^{21}$, CN, halogen, C$_3$-C$_7$ cycloalkyl or C$_1$-C$_8$ alkyl optionally substituted by one or more halogen atoms;
R$^5$ is C$_1$-C$_8$ alkyl optionally substituted by one or more halogen atoms, C$_1$-C$_4$ alkyl, OH, OR', —NR$^{19}$R$^{21}$, CN or C$_3$-C$_7$ cycloalkyl; C$_1$-C$_8$ alkoxy optionally substituted by one or more halogen atoms; C$_6$-C$_{14}$ aryl; —(C$_0$-C$_4$ alkyl)-4 to 14 membered heteroaryl, or —($C_0$-$C_4$ alkyl)-3 to 14 membered heterocyclyl wherein the heteroaryl and heterocyclyl contain at least one heteroatom selected from N, O and S, wherein the aryl, heteroaryl and heterocyclyl are each optionally substituted by one or more Z substituents;

$R^6$ is $C_6$-$C_{14}$ aryl; —($C_0$-$C_4$ alkyl)-4 to 14 membered heteroaryl, —($C_0$-$C_4$ alkyl)-3 to 14 membered heterocyclyl wherein the heteroaryl and heterocyclyl contain at least one heteroatom selected from N, O and S, wherein the aryl, heteroaryl and heterocyclyl are each optionally substituted by one or more Z substituents;

W is $C_1$-$C_8$ alkylene optionally substituted by hydroxy, halogens or $C_1$-$C_4$ alkyl;

X is $C_1$-$C_8$ alkylene optionally substituted by hydroxy, halogens or $C_1$-$C_4$ alkyl;

Y is carboxy, alkoxycarbonyl, tetrazolyl, carbamoyl, monoalkylcarbamoyl, dialkylcarbamoyl, or —CONH—S(O)$_q$—$R^x$, wherein $R^x$ is —$C_1$-$C_4$ alkyl or —$NR^{19}R^{21}$;

q is 0, 1 or 2;

$R^7$ is a divalent moiety represented by —O—, —NHC(O)—, —$CH_2$=$CH_2$—, —$C_6$-$C_{14}$ aryl-D-; -3 to 14 membered heterocyclyl-D-, wherein the heterocyclyl contains at least one heteroatom selected from N, O and S, wherein D is O, S, NH or not present;

Z is independently OH, aryl, O-aryl, benzyl, O-benzyl, $C_1$-$C_6$ alkyl optionally substituted by one or more OH groups or $NH_2$ groups, $C_1$-$C_6$ alkyl optionally substituted by one or more halogen atoms, $C_1$-$C_6$ alkoxy optionally substituted by one or more OH groups, $C_1$-$C_6$ alkoxy optionally substituted by one or more halogen, $C_1$-$C_6$ alkoxy optionally substituted by $C_1$-$C_4$ alkoxy, $NR^{18}(SO_2)R^{21}$, $(SO_2)NR^{19}R^{21}$, $(SO_2)R^{21}$, $NR^{18}C(O)R^{21}$, $C(O)NR^{19}R^{21}$, $NR^{18}C(O)NR^{19}R^{21}$, $NR^{18}C(O)OR^{19}$, $NR^{19}R^{21}$, $C(O)OR^{19}$, $C(O)R^{19}$, $SR^{19}$, $OR^{19}$, oxo, CN, $NO_2$, halogen or a 3 to 14 membered heterocyclyl, wherein the heterocyclyl contains at least one heteroatom selected from N, O and S;

$R^{18}$ is independently H or $C_1$-$C_6$ alkyl;

$R^{19}$ and $R^{21}$ are each independently H; $C_1$-$C_8$ alkyl; $C_3$-$C_8$ cycloalkyl; $C_1$-$C_4$ alkoxy-$C_1$-$C_4$ alkyl; ($C_0$-$C_4$ alkyl)-aryl optionally substituted by one or more groups selected from $C_1$-$C_6$ alkyl, $C_1$-$C_6$ alkoxy and halogen; ($C_0$-$C_4$ alkyl)- 3- to 14-membered heterocyclyl, the heterocyclyl including one or more heteroatoms selected from N, O and S, optionally substituted by one or more groups selected from halogen, oxo, $C_1$-$C_6$ alkyl and $C(O)C_1$-$C_6$ alkyl; ($C_0$-$C_4$ alkyl)-O-aryl optionally substituted by one or more groups selected from $C_1$-$C_6$ alkyl, $C_1$-$C_6$ alkoxy and halogen; and ($C_0$-$C_4$ alkyl)-O-3- to 14-membered heterocyclyl, the heterocyclyl including one or more heteroatoms selected from N, O and S, optionally substituted by one or more groups selected from halogen, $C_1$-$C_6$ alkyl or $C(O)C_1$-$C_6$ alkyl; wherein the alkyl groups are optionally substituted by one or more halogen atoms, $C_1$-$C_4$ alkoxy, $C(O)NH_2$, $C(O)NHC_1$-$C_6$ alkyl or $C(O)N(C_1$-$C_6$ alkyl)$_2$; or $R^{19}$ and $R^{21}$ together with the nitrogen atom to which they attached form a 5- to 10-membered heterocyclyl, the heterocyclyl including one or more further heteroatoms selected from N, O and S, the heterocyclyl being optionally substituted by one or more substituents selected from OH; halogen; aryl; 5- to 10-membered heterocyclyl including one or more heteroatoms selected from N, O and S; $S(O)_2$-aryl; $S(O)_2$—$C_1$-$C_6$ alkyl; $C_1$-$C_6$ alkyl optionally substituted by one or more halogen atoms; $C_1$-$C_6$ alkoxy optionally substituted by one or more OH groups or $C_1$-$C_4$ alkoxy; and $C(O)OC_1$-$C_6$ alkyl, wherein the aryl and heterocyclyl substituent groups are themselves optionally substituted by $C_1$-$C_6$ alkyl, $C_1$-$C_6$ haloalkyl or $C_1$-$C_6$ alkoxy.

Embodiment 3

The compound according to embodiment 1 or 2, wherein
R' is H, $C_1$-$C_8$ alkyl optionally substituted by one or more halogen atoms;

$R^1$ is H, $C_1$-$C_8$ alkyl optionally substituted by one or more halogen atoms, $C_1$-$C_4$ alkyl, OH, or OR'; or $R^1$ is —X—Y; or $R^1$ is —W—$R^7$—X—Y; or $R^1$ is —$S(O)_2$—X—Y or $R^2$ is —$S(O)_2$—W—$R^7$—X—Y;

$R^2$ is H, $C_1$-$C_8$ alkyl optionally substituted by one or more halogen atoms, $C_1$-$C_4$ alkyl, OH, or OR'; $R^2$ is —X—Y; or $R^2$ is —W—$R^7$—X—Y; or $R^2$ is —$S(O)_2$—X—Y; $R^2$ is —$S(O)_2$—W—$R^7$—X—Y;

$R^{2a}$ is H; or $R^2$ and $R^{2a}$ together are oxo;

$R^3$ is H, $C_1$-$C_4$ alkoxy, OH, —$NR^{19}R^{21}$, CN, halogen, $C_3$-$C_7$ cycloalkyl or $C_1$-$C_4$ alkyl optionally substituted by one or more halogen atoms;

$R^4$ is H, $C_1$-$C_4$ alkoxy, OH, —$NR^{19}R^{21}$, CN, halogen, $C_3$-$C_7$ cycloalkyl or $C_1$-$C_4$ alkyl optionally substituted by one or more halogen atoms;

wherein either $R^1$ or $R^2$ is —X—Y, —W—$R^7$—X—Y, —$S(O)_2$—W—X—Y; or —$S(O)_2$—W—$R^7$—X—Y;

W is $C_1$-$C_6$ alkylene optionally substituted by hydroxy, halogens or $C_1$-$C_4$ alkyl;

X is $C_1$-$C_6$ alkylene optionally substituted by hydroxy, halogens or $C_1$-$C_4$ alkyl;

Y is —C(O)OH, —C(O)OR$^x$, tetrazolyl, carbamoyl, monoalkylcarbamoyl, dialkylcarbamoyl, or —CONH—S(O)$_q$—$R^x$, wherein $R^x$ is —$C_1$-$C_4$ alkyl or —$NR^{19}R^{21}$;

q is 2;

$R^7$ is a divalent moiety represented by —$C_6$-$C_{14}$ aryl-D-; -3 to 14 membered heterocyclyl-D-, wherein the heterocyclyl contains at least one heteroatom selected from N, O and S, wherein D is O; and $R^{19}$ and $R^{21}$ are each independently H; $C_1$-$C_6$ alkyl.

Embodiment 4

The compound according to any of the preceding embodiment, wherein
$R^1$ is —X—Y; or —W—$R^7$—X—Y;

$R^2$ is H, $C_1$-$C_8$ alkyl optionally substituted by one or more halogen atoms, $C_1$-$C_4$ alkyl, OH, or OR';

$R^3$ is H, $C_1$-$C_4$ alkoxy, OH, —$NR^{19}R^{21}$, CN, halogen, $C_3$-$C_7$ cycloalkyl or $C_1$-$C_4$ alkyl optionally substituted by one or more halogen atoms;

$R^4$ is H, $C_1$-$C_4$ alkoxy, OH, —$NR^{19}R^{21}$, CN, halogen, $C_3$-$C_7$ cycloalkyl or $C_1$-$C_4$ alkyl optionally substituted by one or more halogen atoms;

W is $C_1$-$C_6$alkylene optionally substituted by hydroxy, halogens or $C_1$-$C_4$ alkyl;

X is $C_1$-$C_6$ alkylene optionally substituted by hydroxy, halogens or $C_1$-$C_4$ alkyl;

Y is —C(O)OH, —C(O)OR$^x$, tetrazolyl, carbamoyl, monoalkylcarbamoyl, dialkylcarbamoyl, or —CONH—S(O)$_q$—$R^x$, wherein $R^x$ is —$C_1$-$C_4$ alkyl or —$NR^{19}R^{21}$;

q is 2;

R' is H, $C_1$-$C_4$ alkyl optionally substituted by one or more halogen atoms;

$R^7$ is a divalent moiety represented by —$C_6$-$C_{14}$ aryl-D-; -3 to 14 membered heterocyclyl-D-, wherein the heterocyclyl contains at least one heteroatom selected from N, O and S, wherein D is O; and $R^{19}$ and $R^{21}$ are each independently H; $C_1$-$C_8$ alkyl.

Embodiment 5

The compound according to any of the preceding embodiment, wherein
$R^1$ is —X—Y; or —W—$R^7$—X—Y;
$R^2$ is H, $C_1$-$C_4$ alkyl optionally substituted by one or more halogen atoms;
$R^3$ is H, $C_1$-$C_4$ alkoxy, OH, —$NR^{19}R^{21}$, CN, halogen, $C_3$-$C_7$ cycloalkyl or $C_1$-$C_4$ alkyl optionally substituted by one or more halogen atoms;
$R^4$ is H, $C_1$-$C_4$ alkoxy, OH, —$NR^{19}R^{21}$, CN, halogen, $C_3$-$C_7$ cycloalkyl or $C_1$-$C_4$ alkyl optionally substituted by one or more halogen atoms;
W is $C_1$-$C_6$ alkylene optionally substituted by hydroxy, halogens or $C_1$-$C_4$ alkyl;
X is $C_1$-$C_6$ alkylene optionally substituted by hydroxy, halogens or $C_1$-$C_4$ alkyl;
Y is —C(O)OH; and
$R^7$ is a divalent moiety represented by —$C_6$-$C_{14}$ aryl-D-; -3 to 14 membered heterocyclyl-D-, wherein the heterocyclyl contains at least one heteroatom selected from N, O and S, wherein D is O.

Embodiment 6

The compound according to any of the preceding embodiment, wherein
$R^1$ is $C_1$-$C_4$ alkyl optionally substituted by one or more halogen atoms, —$(CH_2)_m$—C(O)OR", or —$(CH_2)_m$—$R^7$—$(CH_2)_n$—C(O)OR";
$R^2$ is H, $C_1$-$C_4$ alkyl optionally substituted by one or more halogen atoms;
$R^3$ is H, $C_1$-$C_4$ alkoxy, OH, —$NR^{19}R^{21}$, CN, halogen, $C_3$-$C_7$ cycloalkyl or $C_1$-$C_4$ alkyl optionally substituted by one or more halogen atoms;
$R^4$ is H, $C_1$-$C_4$ alkoxy, OH, —$NR^{19}R^{21}$, CN, halogen, $C_3$-$C_7$ cycloalkyl or $C_1$-$C_4$ alkyl optionally substituted by one or more halogen atoms;
m is 1, 2, 3, 4, 5, 6, 7 or 8;
n is 0, 1, 2 or 3;
R" is H or $C_1$-$C_4$ alkyl optionally substituted by one or more halogen atoms; and
$R^7$ is a divalent moiety represented by —$C_6$-$C_{14}$ aryl-D-; -3 to 14 membered heterocyclyl-D-, wherein the heterocyclyl contains at least one heteroatom selected from N, O and S, wherein D is O

Embodiment 7

The compound according to any of the preceding embodiment, wherein
$R^1$ is —$(CH_2)_m$—C(O)OR", or —$(CH_2)_m$—$R^7$—$(CH_2)_n$—C(O)OR";
$R^2$ is H, $C_1$-$C_4$ alkyl optionally substituted by one or more halogen atoms;
$R^3$ is H, $C_1$-$C_4$ alkoxy, OH, —$NR^{19}R^{21}$, CN, halogen, $C_3$-$C_7$ cycloalkyl or $C_1$-$C_4$ alkyl optionally substituted by one or more halogen atoms;
$R^4$ is H, $C_1$-$C_4$ alkoxy, OH, —$NR^{19}R^{21}$, CN, halogen, $C_3$-$C_7$ cycloalkyl or $C_1$-$C_4$ alkyl optionally substituted by one or more halogen atoms;
m is 1, 2, 3, 4, 5, 6, 7 or 8;
n is 0, 1, 2 or 3;
R" is H or $C_1$-$C_4$ alkyl optionally substituted by one or more halogen atoms; and
$R^7$ is a divalent moiety represented by —$C_6$-$C_{14}$ aryl-D-; -3 to 14 membered heterocyclyl-D-, wherein the heterocyclyl contains at least one heteroatom selected from N, O and S, wherein D is O.

Embodiment 8

The compound according to any of the preceding embodiment, wherein
$R^1$ is —$(CH_2)_m$—C(O)OR";
$R^2$ is H, $C_1$-$C_4$ alkyl optionally substituted by one or more halogen atoms;
$R^3$ is H, $C_1$-$C_4$ alkoxy, OH, —$NR^{19}R^{21}$, CN, halogen, $C_3$-$C_7$ cycloalkyl or $C_1$-$C_4$ alkyl optionally substituted by one or more halogen atoms;
$R^4$ is H, $C_1$-$C_4$ alkoxy, OH, —$NR^{19}R^{21}$, CN, halogen, $C_3$-$C_7$ cycloalkyl or $C_1$-$C_4$ alkyl optionally substituted by one or more halogen atoms;
m is 1, 2, 3, 4, 5, 6, 7 or 8; and
R" is H or $C_1$-$C_4$ alkyl optionally substituted by one or more halogen atoms.

Embodiment 9

The compound according to any of the preceding embodiment, wherein
$R^1$ is —$(CH_2)_m$—C(O)OR";
$R^2$ is H;
$R^3$ is H, $C_1$-$C_4$ alkoxy, OH, —$NR^{19}R^{21}$, CN, halogen, $C_3$-$C_7$ cycloalkyl or $C_1$-$C_4$ alkyl optionally substituted by one or more halogen atoms;
$R^4$ is H, $C_1$-$C_4$ alkoxy, OH, —$NR^{19}R^{21}$, CN, halogen, $C_5$-$C_7$ cycloalkyl or $C_1$-$C_4$ alkyl optionally substituted by one or more halogen atoms;
R" is H; and
m is 4, 5 or 6.

Embodiment 10

The compound according to embodiment 1 or 2, wherein
$R^1$ is X—Y;
$R^2$ is H, or $C_1$-$C_8$ alkyl optionally substituted by one or more halogen atoms;
$R^3$ is H, $C_1$-$C_4$ alkoxy, OH, —$NR^{19}R^{21}$, CN, halogen, $C_3$-$C_7$ cycloalkyl or $C_1$-$C_4$ alkyl optionally substituted by one or more halogen atoms;
$R^4$ is H, $C_1$-$C_4$ alkoxy, OH, —$NR^{19}R^{21}$, CN, halogen, $C_3$-$C_7$ cycloalkyl or $C_1$-$C_4$ alkyl optionally substituted by one or more halogen atoms;
X is $C_1$-$C_6$ alkylene optionally substituted by hydroxy, halogens or $C_1$-$C_4$ alkyl;
Y is —C(O)OH, —C(O)$OR^x$, or —CONH—S(O)$_q$—$R^x$, wherein $R^x$ is —$C_1$-$C_4$ alkyl; and
q is 2.

Embodiment 11

The compound according to embodiment 1 or 2, wherein $R^1$ is

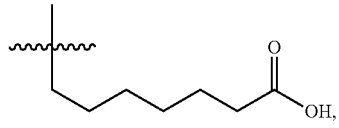

9
-continued
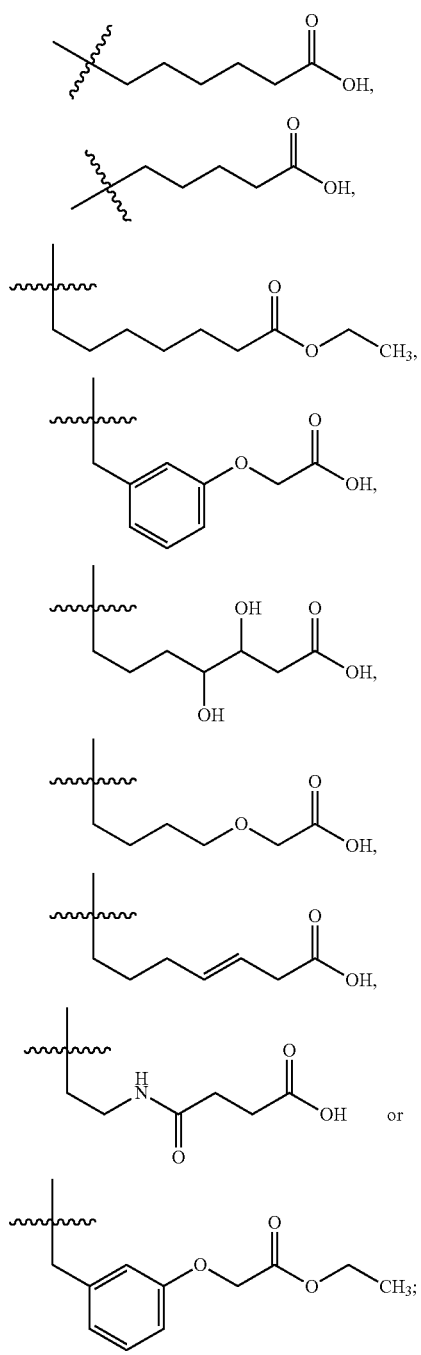
$R^2$ is H,
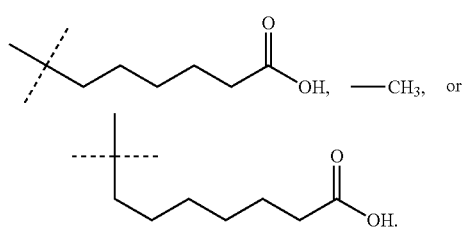—CH₃, or
10
Embodiment 12
The compound according to embodiment 1 or 2, wherein $R^1$ is H, —CH₃,
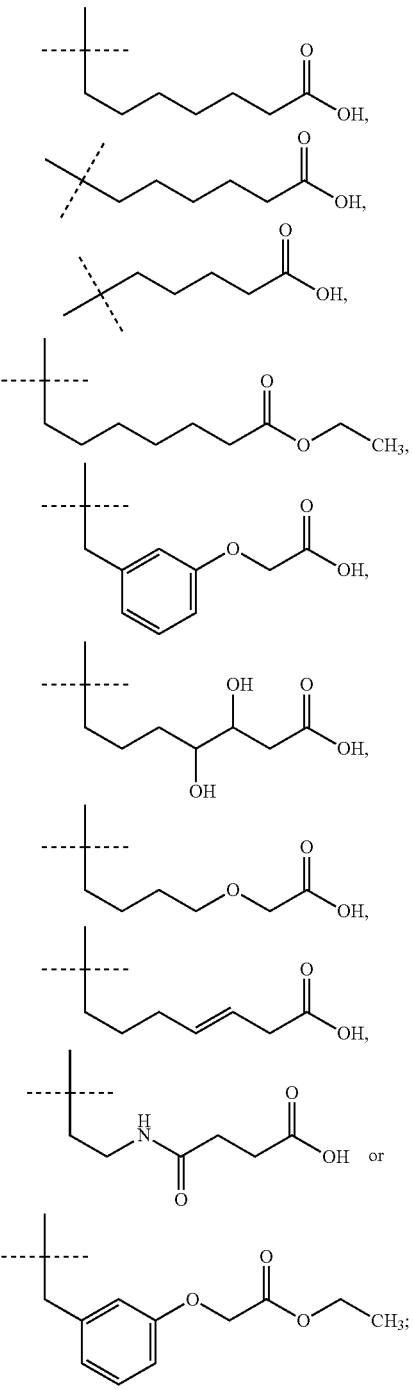
$R^2$ is
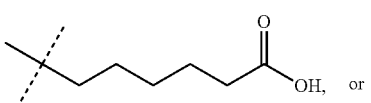 or -continued

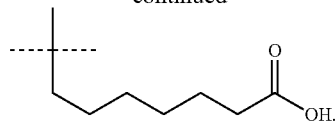

Embodiment 12.1

The compound according to embodiment 2, wherein
$R^2$ and $R^{2a}$ together are oxo.
$R^1$ is X—Y;
$R^3$ is H, $C_1$-$C_4$ alkoxy, OH, —$NR^{19}R^{21}$, CN, halogen, $C_3$-$C_7$ cycloalkyl or $C_1$-$C_4$ alkyl optionally substituted by one or more halogen atoms;
$R^4$ is H, $C_1$-$C_4$ alkoxy, OH, —$NR^{19}R^{21}$, CN, halogen, $C_3$-$C_7$ cycloalkyl or $C_1$-$C_4$ alkyl optionally substituted by one or more halogen atoms;
X is $C_1$-$C_6$ alkylene optionally substituted by hydroxy, halogens or $C_1$-$C_4$ alkyl;
Y is —C(O)OH, —C(O)$OR^x$, or —CONH—S(O)$_q$—$R^x$, wherein $R^x$ is —$C_1$-$C_4$ alkyl; and
q is 2.

Embodiment 13

The compound according to any of the preceding embodiment, wherein
$R^5$ is $C_6$-$C_{14}$ aryl; —($C_0$-$C_4$ alkyl)-4 to 14 membered heteroaryl, or —($C_0$-$C_4$ alkyl)-3 to 14 membered heterocyclyl wherein the heteroaryl and heterocyclyl contain at least one heteroatom selected from N, O and S, wherein the aryl, heteroaryl and heterocyclyl are each optionally substituted by one or more Z substituents; and
$R^6$ is $C_6$-$C_{14}$ aryl; —($C_0$-$C_4$ alkyl)-4 to 14 membered heteroaryl, —($C_0$-$C_4$ alkyl)-3 to 14 membered heterocyclyl wherein the heteroaryl and heterocyclyl contain at least one heteroatom selected from N, O and S, wherein the aryl, heteroaryl and heterocyclyl are each optionally substituted by one or more Z substituents.

Embodiment 14

The compound according to any of the preceding embodiment, wherein
$R^5$ is $C_6$-$C_{14}$ aryl; -5 to 6 membered heteroaryl, or -5 to 6 membered heterocyclyl wherein the heteroaryl and heterocyclyl contain at least one heteroatom selected from N, O and S, wherein the aryl, heteroaryl and heterocyclyl are each optionally substituted by one or more Z substituents; and
$R^6$ is $C_6$-$C_{14}$ aryl; -5 to 6 membered heteroaryl, -5 to 6 membered heterocyclyl wherein the heteroaryl and heterocyclyl contain at least one heteroatom selected from N, O and S, wherein the aryl, heteroaryl and heterocyclyl are each optionally substituted by one or more Z substituents.

Embodiment 15

The compound according to any of the preceding embodiment, wherein
$R^5$ is phenyl; 2-pyridyl, 3-pyridyl, or 4-pyridyl, and
$R^6$ is phenyl; 2-pyridyl, 3-pyridyl, or 4-pyridyl,
wherein the phenyl, 2-pyridyl, 3-pyridyl, and 4-pyridyl are each optionally substituted by one or more Z substituents.

Embodiment 16

The compound according to embodiments 1 to 14, wherein
$R^5$ is phenyl optionally substituted by OH, $C_1$-$C_4$ alkyl optionally substituted by one or more OH groups or $NH_2$ groups; $C_1$-$C_4$ alkyl optionally substituted by one or more halogen atoms; $C_1$-$C_4$ alkoxy optionally substituted by one or more OH groups or $C_1$-$C_4$ alkoxy; $NR^{19}R^{21}$; C(O)$OR^{19}$; C(O)$R^{19}$; $SR^{19}$; $OR^{19}$; CN; $NO_2$; or halogen; and
$R^6$ is phenyl optionally substituted by OH, $C_1$-$C_4$ alkyl optionally substituted by one or more OH groups or $NH_2$ groups; $C_1$-$C_4$ alkyl optionally substituted by one or more halogen atoms; $C_1$-$C_4$ alkoxy optionally substituted by one or more OH groups or $C_1$-$C_4$ alkoxy; $NR^{19}R^{21}$, C(O)$OR^{19}$, C(O)$R^{19}$, $SR^{19}$, $OR^{19}$, CN, $NO_2$, or halogen.

Embodiment 17

The compound according to embodiments 1 to 14 or 16, wherein
$R^5$ is phenyl optionally substituted by $C_1$-$C_4$ alkyl optionally substituted by one or more OH groups or $NH_2$ groups; $C_1$-$C_4$ alkyl optionally substituted by one or more halogen atoms; $C_1$-$C_4$ alkoxy optionally substituted by one or more OH groups or $C_1$-$C_4$ alkoxy; or halogen; and
$R^6$ is phenyl optionally substituted by $C_1$-$C_4$ alkyl optionally substituted by one or more OH groups or $NH_2$ groups; $C_1$-$C_4$ alkyl optionally substituted by one or more halogen atoms; $C_1$-$C_4$ alkoxy optionally substituted by one or more OH groups or $C_1$-$C_4$ alkoxy; or halogen.

Embodiment 18

The compound according to embodiments 1 to 14 or 16-17, wherein
$R^5$ is phenyl optionally substituted by $C_1$-$C_4$ alkoxy, halogen or $C_1$-$C_4$ alkyl optionally substituted by one or more halogen atoms; and
$R^6$ is phenyl optionally substituted by $C_1$-$C_4$ alkoxy, halogen or $C_1$-$C_4$ alkyl optionally substituted by one or more halogen atoms.

Embodiment 19

The compound according to embodiments 1 to 14 or 16-18, wherein
$R^5$ is phenyl optionally substituted by methyl, trifluoromethyl, methoxy or halogen; and
$R^6$ is phenyl optionally substituted by methyl, trifluoromethyl, methoxy or halogen.

Embodiment 20

The compound according to embodiments 1 to 13, wherein
$R^5$ is

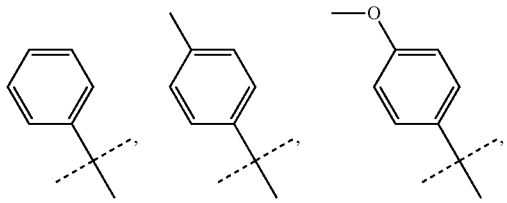

-continued

R⁶ is

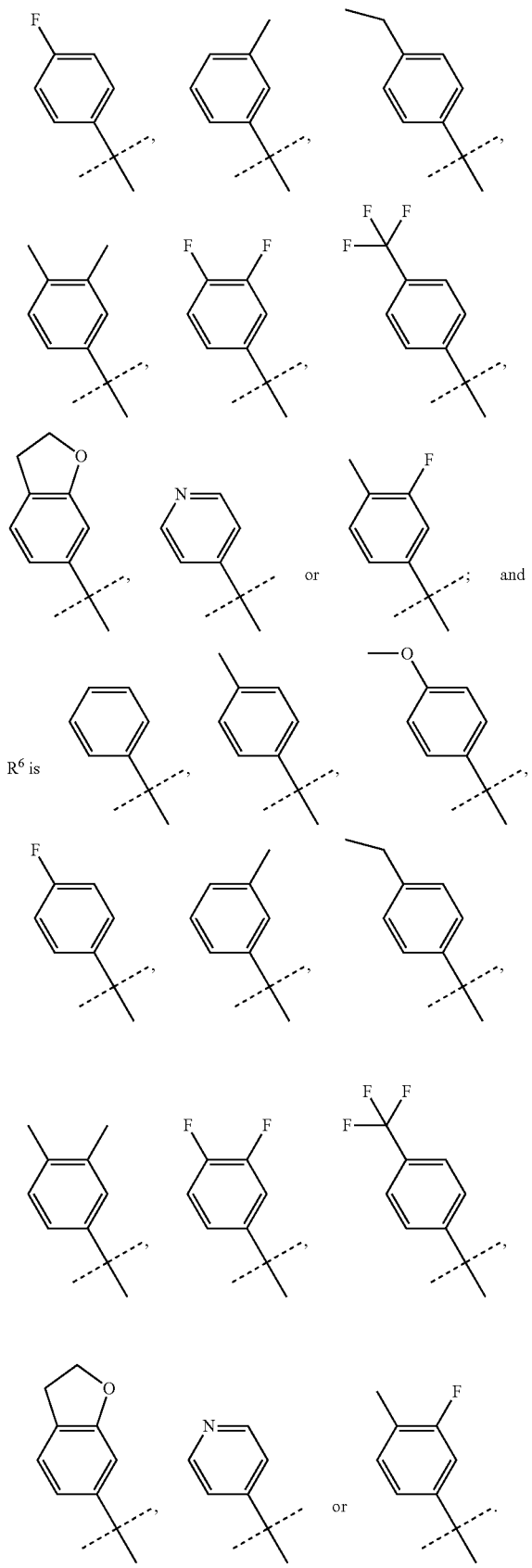

Embodiment 21

The compound according to embodiment 1 or 2, represented by Formula IIa

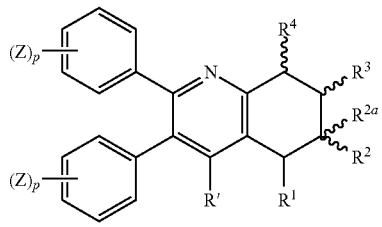

IIa wherein,
$R^1$ is H, $C_1$-$C_8$ alkyl optionally substituted by one or more halogen atoms, $C_1$-$C_4$ alkyl, OH, or OR'; or $R^1$ is —X—Y; or $R^1$ is —W—$R^7$—X—Y; or $R^1$ is —S(O)$_2$—X—Y or $R^2$ is —S(O)$_2$—W—$R^7$—X—Y;

$R^2$ is H, $C_1$-$C_8$ alkyl optionally substituted by one or more halogen atoms, $C_1$-$C_4$ alkyl, OH, OR', —NR$^{19}$R$^{21}$, CN or $C_3$-$C_7$ cycloalkyl; or $R^2$ is —X—Y; or
$R^2$ is —W—$R^7$—X—Y; or
$R^2$ is —S(O)$_2$—W—X—Y;
$R^2$ is —S(O)$_2$—W—$R^7$—X—Y;
wherein either $R^1$ or $R^2$ is —X—Y, —W—$R^7$—X—Y, —S(O)$_2$—W—X—Y; or —S(O)$_2$—W—$R^7$—X—Y;

$R^{2a}$ is hydrogen;
$R^2$ and $R^{2a}$ taken together are oxo;
wherein either $R^1$ or $R^2$ is —X—Y, —W—$R^7$—X—Y, —S(O)$_2$—W—X—Y; or —S(O)$_2$—W—$R^7$—X—Y;

$R^3$ is H, $C_1$-$C_4$ alkoxy, OH, —NR$^{19}$R$^{21}$, CN, halogen, $C_3$-$C_7$ cycloalkyl or $C_1$-$C_8$ alkyl optionally substituted by one or more halogen atoms;

$R^4$ is H, $C_1$-$C_4$ alkoxy, OH, —NR$^{19}$R$^{21}$, CN, halogen, $C_3$-$C_7$ cycloalkyl or $C_1$-$C_8$ alkyl optionally substituted by one or more halogen atoms;

W is $C_1$-$C_6$ alkylene optionally substituted by hydroxy, halogens or $C_1$-$C_4$ alkyl;

X is $C_1$-$C_6$ alkylene optionally substituted by hydroxy, halogens or $C_1$-$C_4$ alkyl;

Y is —C(O)OH, —C(O)OR$^x$, tetrazolyl, carbamoyl, monoalkylcarbamoyl, dialkylcarbamoyl, or —CONH—S(O)$_q$—R$^x$, wherein R$^x$ is —$C_1$-$C_4$ alkyl or —NR$^{19}$R$^{21}$;

p is 0, 1, 2, 3, or 4;
q is 2;
R' is H, $C_1$-$C_4$ alkyl optionally substituted by one or more halogen atoms;

$R^7$ is a divalent moiety represented by —O—, —NHC(O)—, —CH$_2$=CH$_2$—, —C$_6$-C$_{14}$ aryl-D-; -3 to 14 membered heterocyclyl-D-, wherein the heterocyclyl contains at least one heteroatom selected from N, O and S, wherein D is O, S, NH or not present; and $R^{19}$ and $R^{21}$ are each independently H; $C_1$-$C_8$ alkyl.

Embodiment 22

The compound according to embodiment 21, wherein
$R^1$ is —X—Y; or —W—$R^7$—X—Y;
$R^2$ is H, $C_1$-$C_8$ alkyl optionally substituted by one or more halogen atoms, $C_1$-$C_4$ alkyl, OH, oxo or OR';
$R^3$ is H, $C_1$-$C_4$ alkoxy, OH, —NR$^{19}$R$^{21}$, CN, halogen, $C_3$-$C_7$ cycloalkyl or $C_1$-$C_4$ alkyl optionally substituted by one or more halogen atoms;

R$^4$ is H, C$_1$-C$_4$ alkoxy, OH, —NR$^{19}$R$^{21}$, CN, halogen, C$_3$-C$_7$ cycloalkyl or C$_1$-C$_4$ alkyl optionally substituted by one or more halogen atoms;

W is C$_1$-C$_6$ alkylene optionally substituted by hydroxy, halogens or C$_1$-C$_4$ alkyl;

X is C$_1$-C$_6$ alkylene optionally substituted by hydroxy, halogens or C$_1$-C$_4$ alkyl;

Y is —C(O)OH, —C(O)OR$^x$, tetrazolyl, carbamoyl, monoalkylcarbamoyl, dialkylcarbamoyl, or —CONH—S(O)$_q$—R$^x$, wherein R$^x$ is —C$_1$-C$_4$ alkyl or —NR$^{19}$R$^{21}$;

q is 2;

p is 0, 1, 2, 3, or 4;

R' is H, C$_1$-C$_4$ alkyl optionally substituted by one or more halogen atoms; and R$^7$ is a divalent moiety represented by —O—, —NHC(O)—, —CH$_2$=CH$_2$—, —C$_6$-C$_{14}$ aryl-D-; -3 to 14 membered heterocyclyl-D-, wherein the heterocyclyl contains at least one heteroatom selected from N, O and S, wherein D is O, S, NH or not present.

Embodiment 23

The compound according to embodiment 21 or 22, wherein
R$^1$ is —X—Y; or —W—R$^7$—X—Y;
R$^2$ is H, C$_1$-C$_4$ alkyl optionally substituted by one or more halogen atoms;
R$^3$ is H, C$_1$-C$_4$ alkoxy, OH, —NR$^{19}$R$^{21}$, CN, halogen, C$_3$-C$_7$ cycloalkyl or C$_1$-C$_4$ alkyl optionally substituted by one or more halogen atoms;
R$^4$ is H, C$_1$-C$_4$ alkoxy, OH, —NR$^{19}$R$^{21}$, CN, halogen, C$_3$-C$_7$ cycloalkyl or C$_1$-C$_4$ alkyl optionally substituted by one or more halogen atoms;
W is C$_1$-C$_6$ alkylene optionally substituted by hydroxy, halogens or C$_1$-C$_4$ alkyl;
X is C$_1$-C$_6$ alkylene optionally substituted by hydroxy, halogens or C$_1$-C$_4$ alkyl;
Y is —C(O)OH;
p is 0, 1 or 2; and
R$^7$ is a divalent moiety represented by —C$_6$-C$_{14}$ aryl-D-; -3 to 14 membered heterocyclyl-D-, wherein the heterocyclyl contains at least one heteroatom selected from N, O and S, wherein D is O.

Embodiment 24

The compound according to embodiment 21 to 23, wherein
R$^1$ is —(CH$_2$)$_m$—C(O)OR", or —(CH$_2$)$_m$—R$^7$—(CH$_2$)$_n$—C(O)OR";
R$^2$ is H, C$_1$-C$_4$ alkyl optionally substituted by one or more halogen atoms;
R$^3$ is H, C$_1$-C$_4$ alkoxy, OH, —NR$^{19}$R$^{21}$, CN, halogen, C$_3$-C$_7$ cycloalkyl or C$_1$-C$_4$ alkyl optionally substituted by one or more halogen atoms;
R$^4$ is H, C$_1$-C$_4$ alkoxy, OH, —NR$^{19}$R$^{21}$, CN, halogen, C$_3$-C$_7$ cycloalkyl or C$_1$-C$_4$ alkyl optionally substituted by one or more halogen atoms;
m is 1, 2, 3, 4, 5, 6, 7 or 8;
n is 0, 1, 2 or 3;
p is 0, 1 or 2;
R" is H or C$_1$-C$_4$ alkyl optionally substituted by one or more halogen atoms; and
R$^7$ is a divalent moiety represented by —C$_6$-C$_{14}$ aryl-D-; -3 to 14 membered heterocyclyl-D-, wherein the heterocyclyl contains at least one heteroatom selected from N, O and S, wherein D is O;

Embodiment 25

The compound according to embodiment 21 to 24, wherein
R$^1$ is —(CH$_2$)$_m$—C(O)OR", or —(CH$_2$)$_m$—R$^7$—(CH$_2$)$_n$—C(O)OR";
R$^2$ is H, C$_1$-C$_4$ alkyl optionally substituted by one or more halogen atoms;
R$^3$ is H, C$_1$-C$_4$ alkoxy, OH, —NR$^{19}$R$^{21}$, CN, halogen, C$_3$-C$_7$ cycloalkyl or C$_1$-C$_4$ alkyl optionally substituted by one or more halogen atoms;
R$^4$ is H, C$_1$-C$_4$ alkoxy, OH, —NR$^{19}$R$^{21}$, CN, halogen, C$_3$-C$_7$ cycloalkyl or C$_1$-C$_4$ alkyl optionally substituted by one or more halogen atoms;
m is 1, 2, 3, 4, 5, 6, 7 or 8;
n is 0, 1, 2 or 3;
p is 0, 1 or 2;
R" is H or C$_1$-C$_4$ alkyl optionally substituted by one or more halogen atoms; and
R$^7$ is a divalent moiety represented by -phenyl-D-; or -pyridyl-D-, wherein D is O.

Embodiment 26

The compound according to embodiment 21 to 25, wherein
R$^1$ is —(CH$_2$)$_m$—C(O)OR";
R$^2$ is H, C$_1$-C$_4$ alkyl optionally substituted by one or more halogen atoms;
R$^3$ is H, C$_1$-C$_4$ alkoxy, OH, —NR$^{19}$R$^{21}$, CN, halogen, C$_3$-C$_7$ cycloalkyl or C$_1$-C$_4$ alkyl optionally substituted by one or more halogen atoms;
R$^4$ is H, C$_1$-C$_4$ alkoxy, OH, —NR$^{19}$R$^{21}$, CN, halogen, C$_3$-C$_7$ cycloalkyl or C$_1$-C$_4$ alkyl optionally substituted by one or more halogen atoms;
m is 1, 2, 3, 4, 5, 6, 7 or 8;
p is 0, 1 or 2; and
R" is H or C$_1$-C$_4$ alkyl optionally substituted by one or more halogen atoms.

Embodiment 27

The compound according to embodiment 21 to 26, wherein
R$^1$ is —(CH$_2$)$_m$—C(O)OR";
R$^2$ is H;
R$^3$ is H, C$_1$-C$_4$ alkoxy, OH, —NR$^{19}$R$^{21}$, CN, halogen, C$_3$-C$_7$ cycloalkyl or C$_1$-C$_4$ alkyl optionally substituted by one or more halogen atoms;
R$^4$ is H, C$_1$-C$_4$ alkoxy, OH, —NR$^{19}$R$^{21}$, CN, halogen, C$_3$-C$_7$ cycloalkyl or C$_1$-C$_4$ alkyl optionally substituted by one or more halogen atoms;
R" is H;
m is 4, 5 or 6; and
p is 0 or 1.

Embodiment 28

The compound according to embodiment 21 to 27, wherein
R$^1$ is

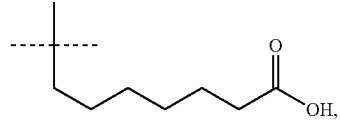

17
-continued
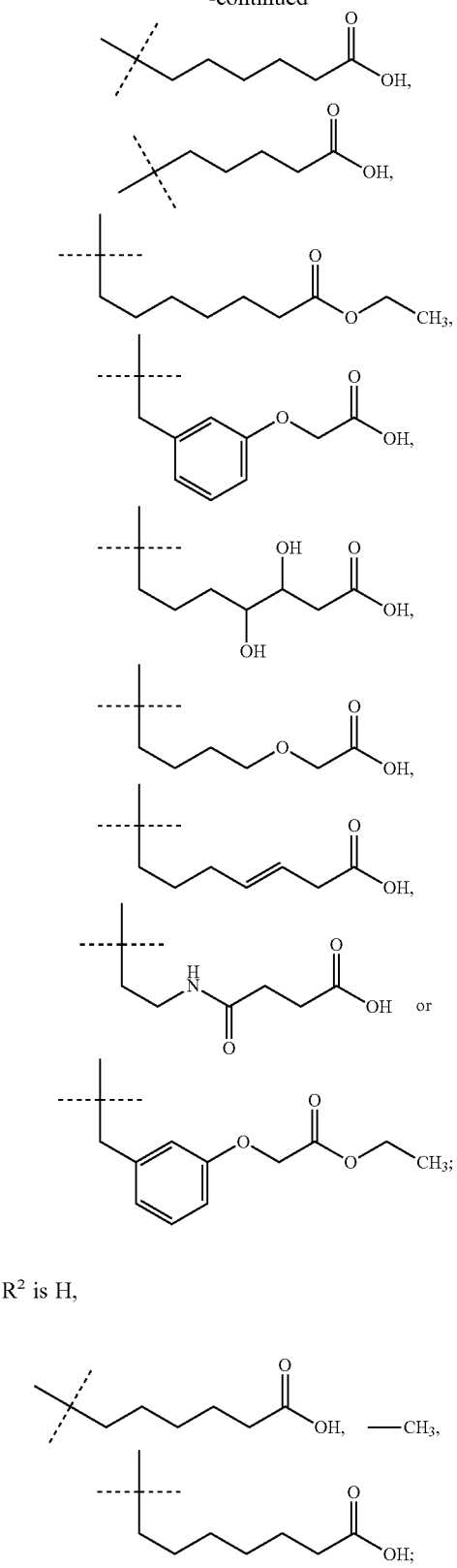
$R^2$ is H,
$R''$ is H;
m is 4, 5 or 6; and
p is 0 or 1.
18
Embodiment 29
The compound according to embodiment 21 to 27, wherein
$R^1$ is H, —CH$_3$, $R^1$ is
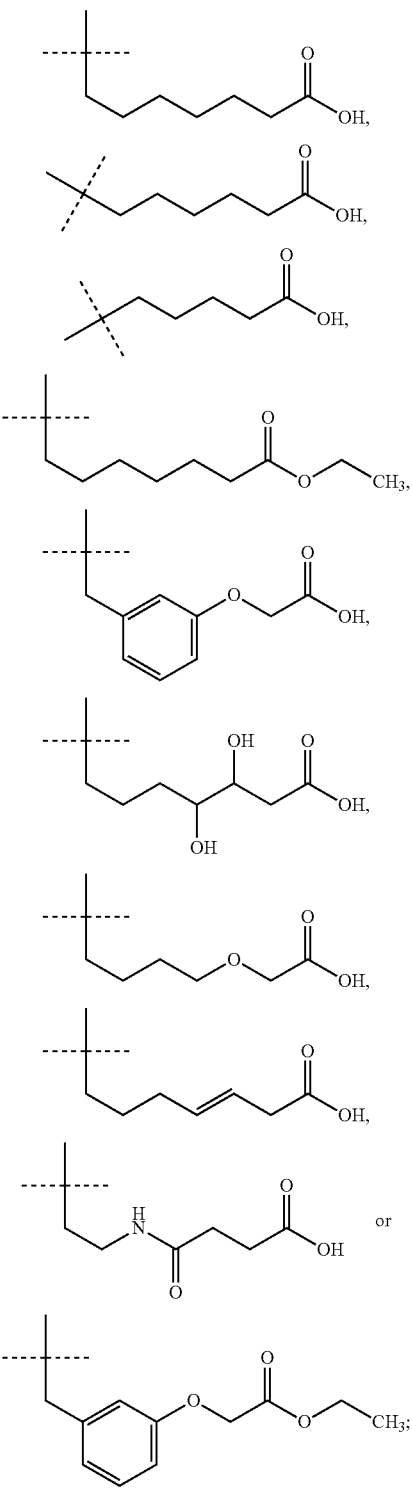

$R^2$ is

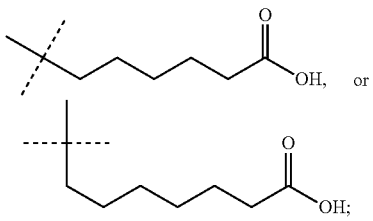

R" is H;
m is 4, 5 or 6; and
p is 0 or 1.

Embodiment 29.1

The compound according to embodiment 1 or 2, wherein $R^2$ and $R^{2a}$ together are oxo.
$R^1$ is X—Y;
$R^3$ is H, $C_1$-$C_4$ alkoxy, OH, —$NR^{19}R^{21}$, CN, halogen, $C_3$-$C_7$ cycloalkyl or $C_1$-$C_4$ alkyl optionally substituted by one or more halogen atoms;
$R^4$ is H, $C_1$-$C_4$ alkoxy, OH, —$NR^{19}R^{21}$, CN, halogen, $C_3$-$C_7$ cycloalkyl or $C_1$-$C_4$ alkyl optionally substituted by one or more halogen atoms;
X is $C_1$-$C_6$ alkylene optionally substituted by hydroxy, halogens or $C_1$-$C_4$ alkyl;
Y is —C(O)OH, or —CONH—S(O)$_q$—$R^x$, wherein $R^x$ is —$C_1$-$C_4$ alkyl; and
q is 2.

Embodiment 29

The compound according to any proceeding embodiment, wherein
$R^3$ and $R^4$ are independently H, OH, $C_1$-$C_4$ alkyl, $C_1$-$C_4$ alkoxy, $C_3$-$C_6$ cycloalkyl, cyano or halogen.

Embodiment 30

The compound according to any proceeding embodiment, wherein
$R^3$ and $R^4$ are independently H, OH, $C_1$-$C_4$ alkyl, $C_1$-$C_4$ alkoxy, $C_3$-$C_5$ cycloalkyl, or halogen.

Embodiment 31

The compound according to any proceeding embodiment, wherein
$R^3$ and $R^4$ are independently H, OH, methyl, ethyl, isopropyl, tert-butyl, methoxy, ethoxy, propoxy, butoxy, cyclopropyl, fluorine, bromine or chlorine.

Embodiment 32

The compound according to any proceeding embodiment, wherein
Z is independently OH, $C_6$-aryl, O—$C_6$-aryl, benzyl, O-benzyl, $C_1$-$C_4$ alkyl optionally substituted by one or more OH groups or $NH_2$ groups, $C_1$-$C_4$ alkyl optionally substituted by one or more halogen atoms, $C_1$-$C_4$ alkoxy optionally substituted by one or more OH groups or $C_1$-$C_4$ alkoxy, $NR^{18}(SO_2)R^{21}$, $(SO_2)NR^{19}R^{21}$, $(SO_2)R^{21}$, $NR^{18}C(O)R^{21}$, $C(O)NR^{19}R^{21}$, $NR^{18}C(O)NR^{21}$, $NR^{18}C(O)OR^{19}$, $NR^{19}R^{21}$, $C(O)OR^{19}$, $C(O)R^{19}$, $SR^{19}$, $OR^{19}$, oxo, CN, $NO_2$, halogen or a 4 to 6 membered heterocyclyl, wherein the heterocyclyl contains at least one heteroatom selected from N, O and S;
$R^{18}$ is H or $C_1$-$C_4$ alkyl;
$R^{19}$ and $R^{21}$ are each independently H; $C_1$-$C_4$ alkyl; $C_3$-$C_6$ cycloalkyl; $C_1$-$C_4$ alkoxy-$C_1$-$C_4$ alkyl; ($C_0$-$C_4$ alkyl)-aryl optionally substituted by one or more groups selected from $C_1$-$C_4$ alkyl, $C_1$-$C_4$ alkoxy and halogen; ($C_0$-$C_4$ alkyl)- 4- to 6-membered heterocyclyl, the heterocyclyl including one or more heteroatoms selected from N, O and S, optionally substituted by one or more groups selected from halogen, oxo, $C_1$-$C_4$ alkyl and C(O)$C_1$-$C_4$ alkyl; ($C_0$-$C_4$ alkyl)-O-aryl optionally substituted by one or more groups selected from $C_1$-$C_6$ alkyl, $C_1$-$C_6$ alkoxy and halogen; and ($C_0$-$C_4$ alkyl)-O-3- to 14-membered heterocyclyl, the heterocyclyl including one or more heteroatoms selected from N, O and S, optionally substituted by one or more groups selected from halogen, $C_1$-$C_6$ alkyl or C(O)$C_1$-$C_6$ alkyl; wherein the alkyl groups are optionally substituted by one or more halogen atoms, $C_1$-$C_4$ alkoxy, $C(O)NH_2$, $C(O)NHC_1$-$C_6$ alkyl or $C(O)N(C_1$-$C_6$ alkyl)$_2$; or
$R^{19}$ and $R^{21}$ together with the nitrogen atom to which they attached form a 5- to 6-membered heterocyclyl, the heterocyclyl including one or more further heteroatoms selected from N, O and S, the heterocyclyl being optionally substituted by one or more substituents selected from OH; halogen; aryl; 5- to 6-membered heterocyclyl including one or more heteroatoms selected from N, O and S; $S(O)_2$-aryl; $S(O)_2$—$C_1$-$C_6$ alkyl; $C_1$-$C_6$ alkyl optionally substituted by one or more halogen atoms; $C_1$-$C_4$ alkoxy optionally substituted by one or more OH groups or $C_1$-$C_4$ alkoxy; and $C(O)OC_1$-$C_6$ alkyl, wherein the aryl and heterocyclyl substituent groups are themselves optionally substituted by $C_1$-$C_6$ alkyl, $C_1$-$C_6$ haloalkyl or $C_1$-$C_6$ alkoxy.

Embodiment 33

The compound according to any proceeding embodiment, wherein
Z is independently OH, $C_1$-$C_4$ alkyl optionally substituted by one or more OH groups or $NH_2$ groups, $C_1$-$C_4$ alkyl optionally substituted by one or more halogen atoms, $C_1$-$C_4$ alkoxy optionally substituted by one or more OH groups or $C_1$-$C_4$ alkoxy, $NR^{19}R^{21}$, $C(O)OR^{19}$, $C(O)R^{19}$, $SR^{19}$, $OR^{19}$, CN, $NO_2$, or halogen;
$R^{19}$ and $R^{21}$ are each independently H; $C_1$-$C_4$ alkyl; $C_3$-$C_6$ cycloalkyl; or $C_1$-$C_4$ alkoxy-$C_1$-$C_4$ alkyl, wherein all alkyls are optionally substituted with halogens.

Embodiment 34

The compound according to any proceeding embodiment, wherein
Z is independently OH, $C_1$-$C_4$ alkyl optionally substituted by one or more OH groups or $NH_2$ groups, $C_1$-$C_4$ alkyl optionally substituted by one or more halogen atoms, $C_1$-$C_4$ alkoxy optionally substituted by one or more OH groups or $C_1$-$C_4$ alkoxy, $C(O)OR^{19}$, $C(O)R^{19}$, $OR^{19}$, CN, or halogen;
$R^{19}$ is H; $C_1$-$C_4$ alkyl; $C_3$-$C_6$ cycloalkyl; or $C_1$-$C_4$ alkoxy-$C_1$-$C_4$ alkyl, wherein all alkyl are optionally substituted with halogens.

Embodiment 35

The compound according to any proceeding embodiment, wherein

Z is independently, $C_1$-$C_4$ alkyl optionally substituted by one or more halogen atoms, $C_1$-$C_4$ alkoxy or halogen;

Embodiment 36

The compound according to embodiment 2 to 35, wherein formula Ia has the following stereochemistry:

Ia'
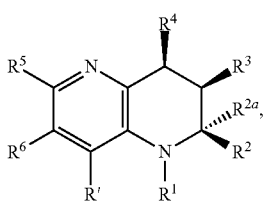

Ia''
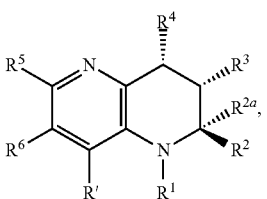

Ia'''
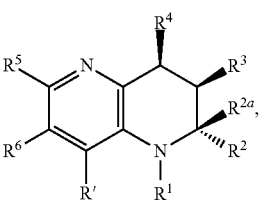

Ia''''
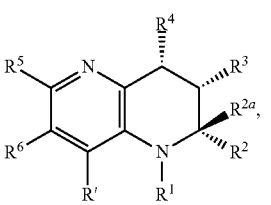

IIa'
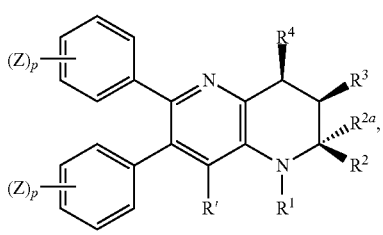

IIa''
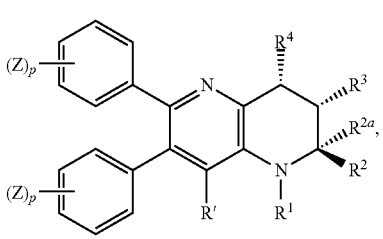

IIa'''
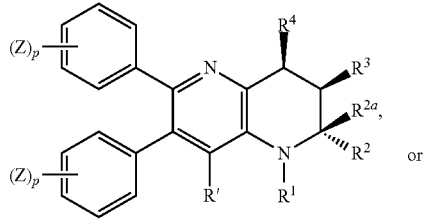

or

IIa''''
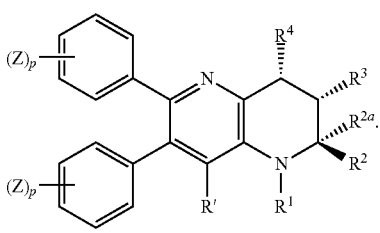

Embodiment 37

The compound according to any one of embodiments 1 to 36, or a pharmaceutically acceptable salt thereof, for use as a medicament for the treatment of a disorder or disease in a subject mediated by activating IP receptor.

Embodiment 38

Use of a compound according to any one of embodiments 1 to 36, or a pharmaceutically acceptable salt thereof for the treatment of a disorder or disease in a subject by activating the IP receptor.

Embodiment 39

The use according to embodiment 37, wherein the disease or disorder is PAH, disorders in need of antiplatlet therapy, atherosclerosis, asthma, COPD, hyperglycemia, inflammatory disease, or fibrotic diseases.

Embodiment 40

The use according to embodiment 37, wherein the disease or disorder is PAH, atherosclerosis, asthma, COPD, hyperglycemia, or fibrotic diseases.

Embodiment 41

The use according to embodiment 37, wherein the disease or disorder is PAH, asthma, COPD, or cystic fibrosis.

Embodiment 42

The use according to embodiment 37, wherein the disease or disorder is PAH or COPD.

Embodiment 43

The use according to embodiment 37, wherein the disease or disorder is PAH or COPD.

Embodiment 44

The use according to embodiment 37, wherein the disease or disorder is PAH.

Embodiment 45

A compound represented by Formula I

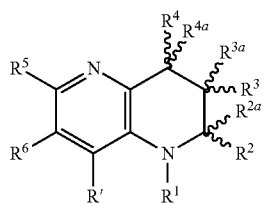

(I)

or a pharmaceutically acceptable salt thereof, wherein

R' is H, $C_1$-$C_8$ alkyl optionally substituted by one or more halogen atoms;

$R^1$ is selected from H; $C_1$-$C_8$ alkyl optionally substituted by one or more halogen atoms, OH, $C_1$-$C_4$ alkoxy, $C_3$-$C_7$ cycloalkyl or $C_3$-$C_7$ cycloalkyloxy; —($C_2$-$C_4$ alkyl)-$NR^{19}R^{21}$ and $C_3$-$C_7$ cycloalkyl; or $R^1$ is —X—Y; or $R^1$ is —W—$R^7$—X—Y; or $R^1$ is —S(O)$_2$—X—Y; or $R^1$ is —S(O)$_2$—W—$R^7$—X—Y;

$R^2$ is selected from H; $C_1$-$C_8$ alkyl optionally substituted by one or more halogen atoms, OH, $C_1$-$C_4$ alkoxy, $C_3$-$C_7$ cycloalkyl or $C_3$-$C_7$ cycloalkyloxy; —($C_1$-$C_4$ alkyl)-$NR^{19}R^{21}$ and $C_3$-$C_7$ cycloalkyl; or $R^2$ is —X—Y; or $R^2$ is —W—$R^7$—X—Y; or $R^2$ is —S(O)$_2$—X—Y;

$R^2$ is —S(O)$_2$—W—$R^7$—X—Y;

$R^{2a}$ is selected from H; $C_1$-$C_8$ alkyl optionally substituted by one or more halogen atoms, OH, $C_1$-$C_4$ alkoxy, $C_3$-$C_7$ cycloalkyl or $C_3$-$C_7$ cycloalkyloxy; and $C_3$-$C_7$ cycloalkyl; or $R^2$ and $R^{2a}$ taken together are oxo;

wherein either $R^1$ or $R^2$ is —X—Y, —W—$R^7$—X—Y, —S(O)$_2$—W—X—Y; or —S(O)$_2$—W—$R^7$—X—Y;

$R^3$ is selected from H; OH; $C_1$-$C_8$ alkyl optionally substituted by one or more halogen atoms, OH, $C_1$-$C_4$ alkoxy, $C_3$-$C_7$ cycloalkyl or $C_3$-$C_7$ cycloalkyloxy; $C_1$-$C_4$ alkoxy; OR'; —($C_0$-$C_4$alkyl)-$NR^{19}R^{21}$; CN; halogen and $C_3$-$C_7$ cycloalkyl;

$R^{3a}$ is selected from H; $C_1$-$C_8$ alkyl optionally substituted by one or more halogen atoms, OH, $C_1$-$C_4$ alkoxy, $C_3$-$C_7$ cycloalkyl or $C_3$-$C_7$ cycloalkyloxy; and $C_3$-$C_7$ cycloalkyl; or $R^3$ and $R^{3a}$ taken together are oxo;

$R^4$ is selected from H; OH; $C_1$-$C_8$ alkyl optionally substituted by one or more halogen atoms, OH, $C_1$-$C_4$ alkoxy, $C_3$-$C_7$ cycloalkyl or $C_3$-$C_7$ cycloalkyloxy; $C_1$-$C_4$ alkoxy; OR'; —($C_0$-$C_4$alkyl)-$NR^{19}R^{21}$; CN; halogen and $C_3$-$C_7$ cycloalkyl;

$R^{4a}$ is selected from H; $C_1$-$C_8$ alkyl optionally substituted by one or more halogen atoms, OH, $C_1$-$C_4$ alkoxy, $C_3$-$C_7$ cycloalkyl or $C_3$-$C_7$ cycloalkyloxy; and $C_3$-$C_7$ cycloalkyl; or $R^4$ and $R^{4a}$ taken together are oxo;

$R^5$ and $R^6$ are independently selected from $C_6$-$C_{14}$ aryl and —($C_0$-$C_4$ alkyl)-4 to 14 membered heteroaryl, wherein the aryl and heteroaryl are each optionally substituted by one or more Z substituents;

W is $C_1$-$C_8$ alkylene optionally substituted by hydroxy, halogens or $C_1$-$C_4$ alkyl;

X is $C_1$-$C_8$ alkylene optionally substituted by hydroxy, halogens or $C_1$-$C_4$ alkyl;

Y is selected from

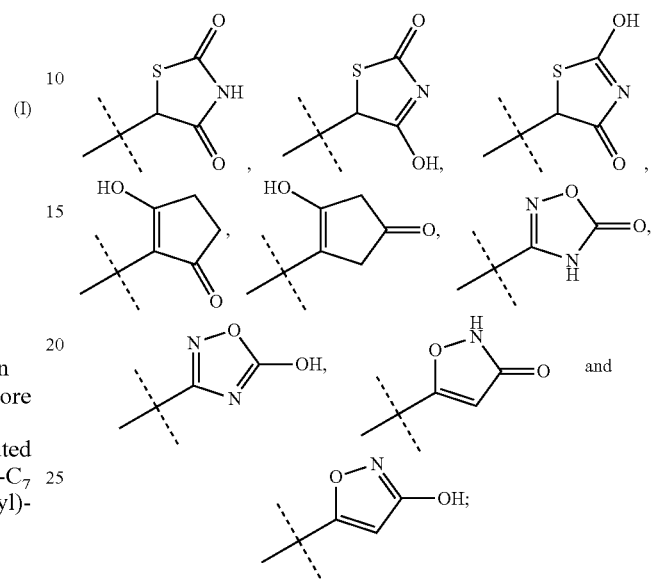

$R^7$ is a divalent moiety represented by —O—, —NHC(O)—, —CH$_2$=CH$_2$—, —$C_6$-$C_{14}$ aryl-D-; -3 to 14 membered heterocyclyl-D-, wherein the heterocyclyl contains at least one heteroatom selected from N, O and S, wherein D is O, S, NH or not present;

Z is independently OH, aryl, O-aryl, benzyl, O-benzyl, $C_1$-$C_6$ alkyl optionally substituted by one or more OH groups or NH$_2$ groups, $C_1$-$C_6$ alkyl optionally substituted by one or more halogen atoms, $C_1$-$C_6$ alkoxy optionally substituted by one or more OH groups, $C_1$-$C_6$ alkoxy optionally substituted by one or more halogen, $C_1$-$C_6$ alkoxy optionally substituted by $C_1$-$C_4$ alkoxy, $NR^{18}(SO_2)R^{21}$, $(SO_2)NR^{19}R^{21}$, $(SO_2)R^{21}$, $NR^{18}C(O)R^{21}$, $C(O)NR^{19}R^{21}$, $NR^{18}C(O)NR^{19}R^{21}$, $NR^{18}C(O)OR^{19}$, $NR^{19}R^{21}$, $C(O)OR^{19}$, $C(O)R^{19}$, $SR^{19}$, $OR^{19}$, oxo, CN, NO$_2$, halogen or a 3 to 14 membered heterocyclyl, wherein the heterocyclyl contains at least one heteroatom selected from N, O and S;

$R^{18}$ is independently H or $C_1$-$C_6$ alkyl;

$R^{19}$ and $R^{21}$ are each independently H; $C_1$-$C_8$ alkyl; $C_3$-$C_8$ cycloalkyl; $C_1$-$C_4$ alkoxy-$C_1$-$C_4$ alkyl; ($C_0$-$C_4$ alkyl)-aryl optionally substituted by one or more groups selected from $C_1$-$C_6$ alkyl, $C_1$-$C_6$ alkoxy and halogen; ($C_0$-$C_4$ alkyl)- 3- to 14-membered heterocyclyl, the heterocyclyl including one or more heteroatoms selected from N, O and S, optionally substituted by one or more groups selected from halogen, oxo, $C_1$-$C_6$ alkyl and C(O)$C_1$-$C_6$ alkyl; ($C_0$-$C_4$ alkyl)-O-aryl optionally substituted by one or more groups selected from $C_1$-$C_6$ alkyl, $C_1$-$C_6$ alkoxy and halogen; and ($C_0$-$C_4$ alkyl)-O-3- to 14-membered heterocyclyl, the heterocyclyl including one or more heteroatoms selected from N, O and S, optionally substituted by one or more groups selected from halogen, $C_1$-$C_6$ alkyl or C(O)$C_1$-$C_6$ alkyl; wherein the alkyl groups are optionally substituted by one or more halogen atoms, $C_1$-$C_4$ alkoxy, C(O)NH$_2$, C(O)NHC$_1$-$C_6$ alkyl or C(O)N($C_1$-$C_6$ alkyl)$_2$; or $R^{19}$ and $R^{21}$ together with the nitrogen atom to which they attached form a 5- to 10-membered heterocyclyl, the heterocyclyl including one or more further heteroatoms selected from N, O and S, the heterocyclyl being optionally substituted by one or more substituents selected from OH; halogen; aryl; 5- to 10-membered heterocyclyl including one or more heteroatoms selected from N, O and S; $S(O)_2$-aryl; $S(O)_2$—$C_1$-$C_6$ alkyl; $C_1$-$C_6$ alkyl optionally substituted by one or more halogen atoms; $C_1$-$C_6$ alkoxy optionally substituted by one or more OH groups or $C_1$-$C_4$ alkoxy; and $C(O)OC_1$-$C_6$ alkyl, wherein the aryl and heterocyclyl substituent groups are themselves optionally substituted by $C_1$-$C_6$ alkyl, $C_1$-$C_6$ haloalkyl or $C_1$-$C_6$ alkoxy.

Embodiment 46

The compound according to embodiment 45, wherein
either $R^1$ or $R^2$ is —X—Y or —W—$R^7$—X—Y;
W is $C_1$-$C_6$ alkylene optionally substituted by hydroxy, halogens or $C_1$-$C_4$ alkyl;
X is $C_1$-$C_6$ alkylene optionally substituted by hydroxy, halogens or $C_1$-$C_4$ alkyl;
R' is H, $C_1$-$C_4$ alkyl optionally substituted by one or more halogen atoms;
$R^7$ is a divalent moiety represented by —$C_6$-$C_{14}$ aryl-D-; -3 to 14 membered heterocyclyl-D-, wherein the heterocyclyl contains at least one heteroatom selected from N, O and S, wherein D is O.

Embodiment 47

The compound according to embodiment 45 or 47, wherein
either $R^1$ or $R^2$ is —X—Y;
X is $C_1$-$C_6$ alkylene optionally substituted by hydroxy, halogens or $C_1$-$C_4$ alkyl.

Embodiment 48

The compound according to an one of embodiments 45 to 47, wherein
either $R^1$ or $R^2$ is

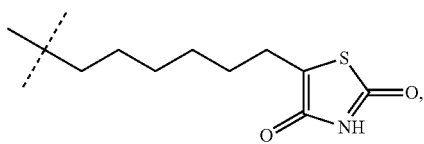

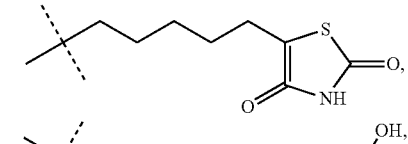

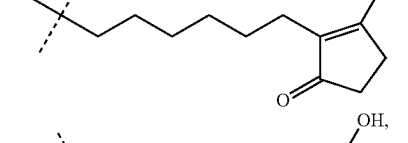

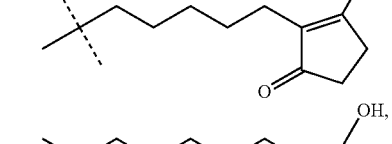

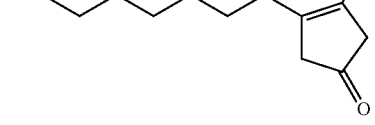

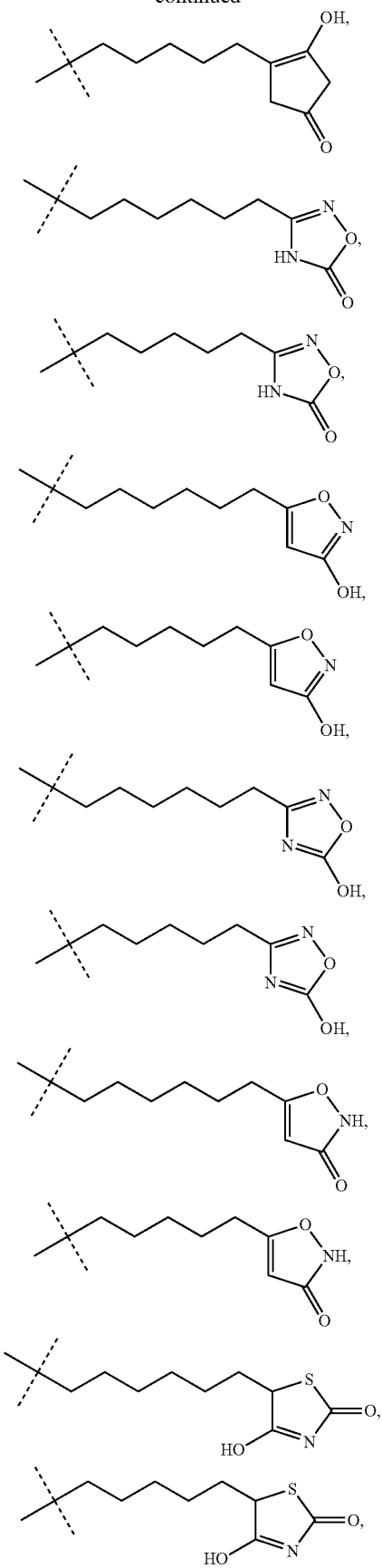

-continued

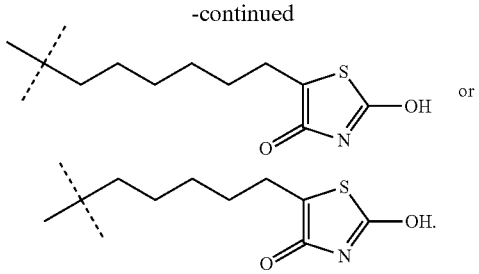

or

Embodiment 49

The compound according to any one of embodiments 45 to 48, wherein
$R^2$ and $R^{2a}$ are independently selected from H; $C_1$-$C_4$ alkyl optionally substituted by one or more halogen atoms or OH; and OH; or $R^2$ and $R^{2a}$ taken together are oxo;
$R^3$ and $R^{3a}$ are independently selected from H; $C_1$-$C_4$ alkyl optionally substituted by one or more halogen atoms or OH; and OH; or $R^3$ and $R^{3a}$ taken together are oxo;
$R^4$ and $R^{4a}$ are independently selected from H, $C_1$-$C_4$ alkyl optionally substituted by one or more halogen atoms or OH; and OH; or $R^4$ and $R^{4a}$ taken together are oxo.

Embodiment 50

The compound according to any one of embodiments 45 to 49, wherein
$R^2$ and $R^{2a}$ are H; or
$R^2$ and $R^{2a}$ taken together are oxo;
$R^3$ and $R^{3a}$ are independently selected from H and OH;
$R^4$ and $R^{4a}$ are independently selected from H and OH.

Embodiment 51

The compound according to any one of embodiments 45-50, wherein
$R^5$ and $R^6$ are independently selected from $C_6$-$C_{14}$ aryl and 5 to 6 membered heteroaryl, wherein the heteroaryl contains at least one heteroatom selected from N, O and S, wherein the aryl and heteroaryl are each optionally substituted by one or more Z substituents.

Embodiment 52

The compound according to any one of embodiments 45 to 51, wherein
$R^5$ and $R^6$ are independently selected from phenyl; 2-pyridyl, 3-pyridyl, or 4-pyridyl, wherein the phenyl, 2-pyridyl, 3-pyridyl, and 4-pyridyl are each optionally substituted by one or more Z substituents.

Embodiment 53

The compound according to any one of the embodiments 45-52, wherein
$R^5$ and $R^6$ are independently selected from phenyl optionally substituted by OH, $C_1$-$C_4$ alkyl optionally substituted by one or more OH groups or $NH_2$ groups; $C_1$-$C_4$ alkyl optionally substituted by one or more halogen atoms; $C_1$-$C_4$ alkoxy optionally substituted by one or more OH groups or $C_1$-$C_4$ alkoxy; $NR^{19}R^{21}$; $C(O)OR^{19}$; $C(O)R^{19}$; $SR^{19}$; $OR^{19}$; CN; $NO_2$; and halogen.

Embodiment 54

The compound according to any one of embodiments 45 to 53, wherein
$R^5$ and $R^6$ are independently selected from phenyl optionally substituted by $C_1$-$C_4$ alkyl optionally substituted by one or more OH groups or $NH_2$ groups; $C_1$-$C_4$ alkyl optionally substituted by one or more halogen atoms; $C_1$-$C_4$ alkoxy optionally substituted by one or more OH groups or $C_1$-$C_4$ alkoxy; and halogen.

Embodiment 55

The compound according to any one of embodiments 45 to 54, wherein
$R^5$ and $R^8$ are independently selected from phenyl optionally substituted by $C_1$-$C_4$ alkoxy or halogen, and $C_1$-$C_4$ alkyl optionally substituted by one or more halogen atoms.

Embodiment 56

The compound according to any one of embodiments 45 to 55, wherein
$R^5$ and $R^8$ are independently selected from phenyl optionally substituted by methyl, ethyl, trifluoromethyl, methoxy or halogen.

Embodiment 57

The compound according to any one of embodiments 45 to 56, wherein
$R^5$ is

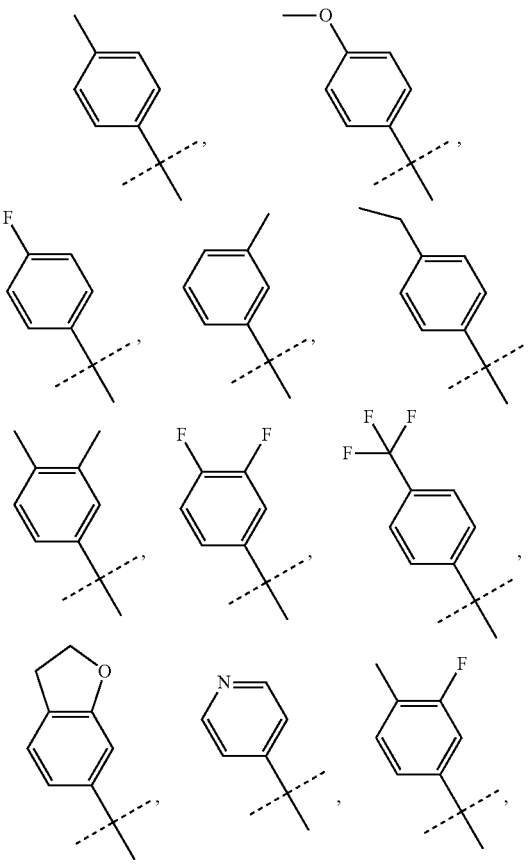

-continued

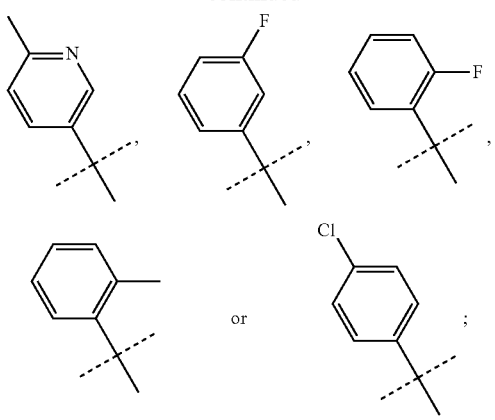

and
R⁶ is

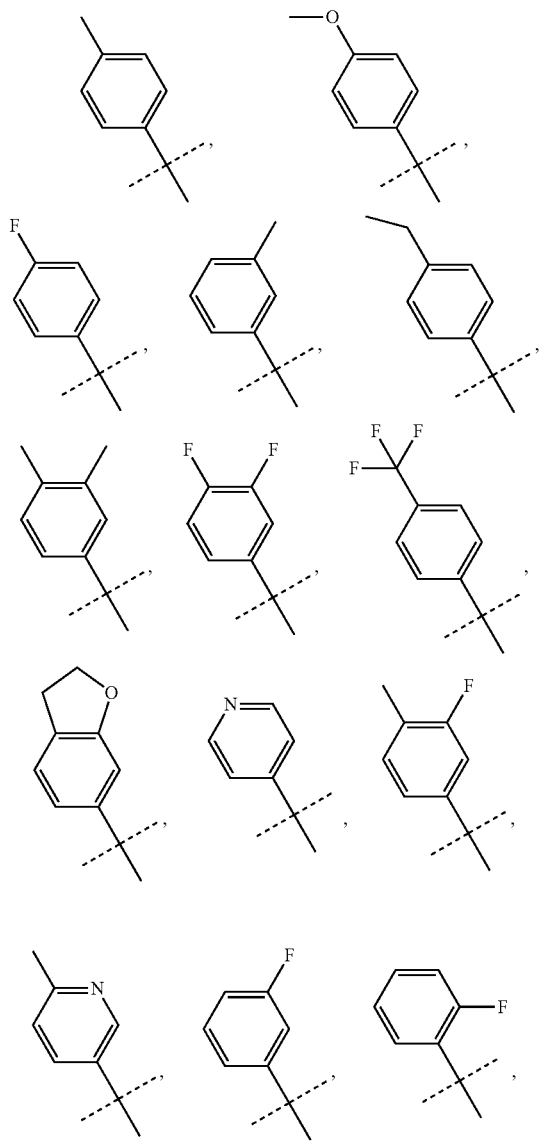

-continued

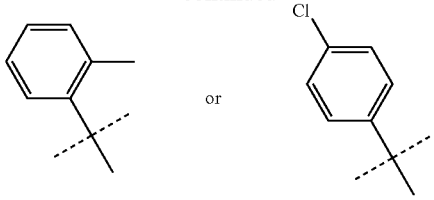

Embodiment 58

The compound according to any one of embodiments 45 to 57, wherein
$R^3$, $R^{3a}$, $R^4$ and $R^{4a}$ are independently selected from H, OH, $C_1$-$C_4$ alkyl, $C_1$-$C_4$ alkoxy, $C_3$-$C_6$ cycloalky, cyano and halogen.

Embodiment 59

The compound according to any one of embodiments 45 to 58, wherein
$R^3$, $R^{3a}$, $R^4$ and $R^{4a}$ are independently H, OH, $C_1$-$C_4$ alkyl, $C_1$-$C_4$ alkoxy, $C_3$-$C_5$ cycloalkyl and halogen.

Embodiment 60

The compound according to any one of embodiments 45 to 59, wherein
$R^3$, $R^{3a}$, $R^4$ and $R^{4a}$ are independently selected from H, OH, methyl, ethyl, isopropyl, tert-butyl, methoxy, ethoxy, propoxy, butoxy, cyclopropyl, fluorine, bromine and chlorine.

Embodiment 61

The compound according to any one of embodiments 45 to 60, wherein
Z is independently selected from OH, $C_6$-aryl, O—$C_6$-aryl, benzyl, O-benzyl, $C_1$-$C_4$ alkyl optionally substituted by one or more OH groups or $NH_2$ groups, $C_1$-$C_4$ alkyl optionally substituted by one or more halogen atoms, $C_1$-$C_4$ alkoxy optionally substituted by one or more OH groups or $C_1$-$C_4$ alkoxy, $NR^{18}(SO_2)R^{21}$, $(SO_2)NR^{19}R^{21}$, $(SO_2)R^{21}$, $NR^{18}C(O)R^{21}$, $C(O)NR^{19}R^{21}$, $—NR^{18}C(O)NR^{19}R^{21}$, $NR^{18}C(O)OR^{18}$, $NR^{19}R^{21}$, $C(O)OR^{19}$, $C(O)R^{19}$, $SR^{19}$, $OR^{19}$, oxo, CN, $NO_2$, halogen and a 4 to 6 membered heterocyclyl, wherein the heterocyclyl contains at least one heteroatom selected from N, O and S;
$R^{18}$ is H or $C_1$-$C_4$ alkyl;
$R^{19}$ and $R^{21}$ are each independently selected from H; $C_1$-$C_4$ alkyl; $C_3$-$C_8$ cycloalkyl; $C_1$-$C_4$ alkoxy-$C_1$-$C_4$ alkyl; ($C_0$-$C_4$ alkyl)-aryl optionally substituted by one or more groups selected from $C_1$-$C_4$ alkyl, $C_1$-$C_4$ alkoxy and halogen; ($C_0$-$C_4$ alkyl)- 4- to 6-membered heterocyclyl, the heterocyclyl including one or more heteroatoms selected from N, O and S, optionally substituted by one or more groups selected from halogen, oxo, $C_1$-$C_4$ alkyl and C(O)$C_1$-$C_4$ alkyl; ($C_0$-$C_4$ alkyl)-O-aryl optionally substituted by one or more groups selected from $C_1$-$C_6$ alkyl, $C_1$-$C_6$ alkoxy and halogen; and ($C_0$-$C_4$ alkyl)- O-3- to 14-membered heterocyclyl, the heterocyclyl including one or more heteroatoms selected from N, O and S, optionally substituted by one or more groups selected from halogen, $C_1$-$C_6$ alkyl or C(O)$C_1$-$C_6$ alkyl; wherein the alkyl groups are optionally substituted by one or more halogen atoms, $C_1$-$C_4$ alkoxy, $C(O)NH_2$, $C(O)NHC_1$-$C_6$ alkyl or $C(O)N(C_1$-$C_6$ alkyl$)_2$; or $R^{19}$ and $R^{21}$ together with the nitrogen atom to which they are attached form a 5- to 6-membered heterocyclyl, the heterocyclyl including one or more further heteroatoms selected from N, O and S, the heterocyclyl being optionally substituted by one or more substituents selected from OH; halogen; aryl; 5- to 6-membered heterocyclyl including one or more heteroatoms selected from N, O and S; $S(O)_2$-aryl; $S(O)_2$—$C_1$-$C_6$ alkyl; $C_1$-$C_6$ alkyl optionally substituted by one or more halogen atoms; $C_1$-$C_4$ alkoxy optionally substituted by one or more OH groups or $C_1$-$C_4$ alkoxy; and $C(O)OC_1$-$C_6$ alkyl, wherein the aryl and heterocyclyl substituent groups are themselves optionally substituted by $C_1$-$C_6$ alkyl, $C_1$-$C_6$ haloalkyl or $C_1$-$C_6$ alkoxy.

Embodiment 62

The compound according to any one of embodiments 45 to 54, wherein

Z is independently OH, $C_1$-$C_4$ alkyl optionally substituted by one or more OH groups or $NH_2$ groups, $C_1$-$C_4$ alkyl optionally substituted by one or more halogen atoms, $C_1$-$C_4$ alkoxy optionally substituted by one or more OH groups or $C_1$-$C_4$ alkoxy, $NR^{19}R^{21}$, $C(O)OR^{19}$, $C(O)R^{19}$, $SR^{19}$, $OR^{19}$, CN, $NO_2$, or halogen;

$R^{19}$ and $R^{21}$ are each independently H; $C_1$-$C_4$ alkyl; $C_3$-$C_6$ cycloalkyl; or $C_1$-$C_4$ alkoxy-$C_1$-$C_4$ alkyl, wherein all alkyls are optionally substituted with halogens.

Embodiment 63

The compound according to any one of embodiments 45 to 54, wherein

Z is independently OH, $C_1$-$C_4$ alkyl optionally substituted by one or more OH groups or $NH_2$ groups, $C_1$-$C_4$ alkyl optionally substituted by one or more halogen atoms, $C_1$-$C_4$ alkoxy optionally substituted by one or more OH groups or $C_1$-$C_4$ alkoxy, $C(O)OR^{19}$, $C(O)R^{19}$, $OR^{19}$, CN, or halogen;

$R^{19}$ is H; $C_1$-$C_4$ alkyl; $C_3$-$C_6$ cycloalkyl; or $C_1$-$C_4$ alkoxy-$C_1$-$C_4$ alkyl, wherein all alkyl are optionally substituted with halogens.

Embodiment 64

The compound according to any one of embodiments 45 to 54, wherein

Z is independently, $C_1$-$C_4$ alkyl optionally substituted by one or more halogen atoms, $C_1$-$C_4$ alkoxy or halogen;

Embodiment 65

The compound according to embodiment 45 to 64, wherein formula (I) has the following stereochemistry:

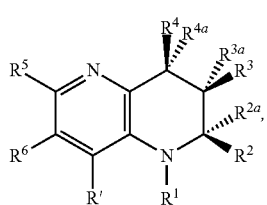

(I)′

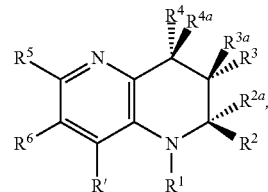

(I)″

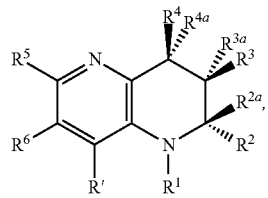

(I)‴

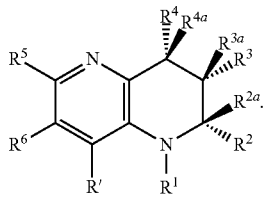

(I)″″

Embodiment 66

The compound according to any one of embodiments 45 to 65, or a pharmaceutically acceptable salt thereof, for use as a medicament.

Embodiment 67

The compound according to any one of embodiments 45 to 65, or a pharmaceutically acceptable salt thereof, for use in the treatment of a disorder or disease mediated by the IP receptor.

Embodiment 68

The compound according to any one of embodiments 45 to 65, or a pharmaceutically acceptable salt thereof, for use in the treatment of a disorder or disease selected from PAH, disorders in need of antiplatelet therapy, atherosclerosis, asthma, COPD, hyperglycemia, inflammatory disease and fibrotic diseases.

Embodiment 69

The compound according to any one of embodiments 45 to 65, or a pharmaceutically acceptable salt thereof, for use in the treatment of a disorder or disease selected from PAH, atherosclerosis, asthma, COPD, hyperglycemia and fibrotic diseases.

Embodiment 70

The compound according to any one of embodiments 45 to 65, or a pharmaceutically acceptable salt thereof, for use in the treatment of a disorder or disease selected from PAH, asthma, COPD and cystic fibrosis.

Embodiment 71

The compound according to any one of embodiments 45 to 65, or a pharmaceutically acceptable salt thereof, for use in the treatment of a disorder or disease selected from PAH or COPD.

Embodiment 72

The compound according to any one of embodiments 45 to 65, or a pharmaceutically acceptable salt thereof, for use in the treatment of PAH.

Embodiment 73

A pharmaceutical composition, comprising:
a therapeutically effective amount of the compound according to any one of embodiments 45 to 65, or a pharmaceutically acceptable salt thereof, and one or more pharmaceutically acceptable carriers.

Embodiment 74

A pharmaceutical combination, comprising:
a therapeutically effective amount of the compound according to any one of embodiments 45 to 65, or a pharmaceutically acceptable salt thereof, and a second active agent.

Embodiment 75

A method of treating pulmonary arterial hypertension in a patient in need thereof, comprising:
administering to the subject in need thereof a therapeutically effective amount of the compound according to any one of embodiments 45 to 65, or a pharmaceutically acceptable salt thereof.

Embodiment 76

Use of a compound according to any one of embodiments 45 to 65, or a pharmaceutically acceptable salt thereof, in the manufacture of a medicament for the treatment of a disorder or disease mediated by the IP receptor.

Embodiment 77

Use of a compound according to any one of embodiments 45 to 65, or a pharmaceutically acceptable salt thereof, in the manufacture of a medicament for the treatment of a disorder or disease selected from PAH, atherosclerosis, asthma, COPD, hyperglycemia and fibrotic diseases.

Embodiment 78

Use of a compound according to any one of embodiments 45 to 65, or a pharmaceutically acceptable salt thereof, in the manufacture of a medicament for the treatment of a disorder or disease selected from PAH, asthma, COPD and cystic fibrosis.

Embodiment 79

Use of a compound according to any one of embodiments 45 to 65, or a pharmaceutically acceptable salt thereof, in the manufacture of a medicament for the treatment of a disorder or disease selected from PAH or COPD.

Embodiment 80

Use of a compound according to any one of embodiments 45 to 65, or a pharmaceutically acceptable salt thereof, in the manufacture of a medicament for the treatment of PAH.

Embodiment 81

Use of a compound according to any one of embodiments 45 to 65, or a pharmaceutically acceptable salt thereof, for the treatment of pulmonary arterial hypertension.

Embodiment 82

A method for the prevention or treatment of a condition affected by activation of the IP receptor, comprising:
administering an effective amount to activate the IP receptor of at least one compound according to any of embodiments 45 to 65 to a subject in need of such treatment.

Embodiment 90

A compound represented by formula

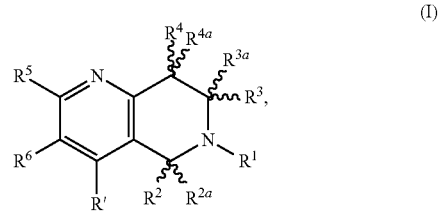

(I)

or a pharmaceutically acceptable salt thereof, wherein
R' is H, $C_1$-$C_8$ alkyl optionally substituted by one or more halogen atoms;
$R^1$ is selected from H; $C_1$-$C_8$ alkyl optionally substituted by one or more halogen atoms, OH, $C_1$-$C_4$ alkoxy, $C_3$-$C_7$ cycloalkyl or $C_3$-$C_7$ cycloalkyloxy; —($C_2$-$C_4$ alkyl)-$NR^{19}R^{21}$ and $C_3$-$C_7$ cycloalkyl; or
$R^1$ is —X—Y; or
$R^1$ is —W—$R^7$—X—Y; or
$R^1$ is —S(O)$_2$—X—Y; or
$R^1$ is —S(O)$_2$—W—$R^7$—X—Y; or
$R^1$ is —C(O)—X—Y; or
$R^1$ is —C(O)—W—$R^7$—X—Y
$R^2$ is selected from H; $C_1$-$C_8$ alkyl optionally substituted by one or more halogen atoms, OH, $C_1$-$C_4$ alkoxy, $C_3$-$C_7$ cycloalkyl or $C_3$-$C_7$ cycloalkyloxy; —($C_1$-$C_4$ alkyl)-$NR^{19}R^{21}$ and $C_3$-$C_7$ cycloalkyl; or
$R^2$ is —X—Y; or
$R^2$ is —W—$R^7$—X—Y; or
$R^2$ is —S(O)$_2$—X—Y; or
$R^2$ is —S(O)$_2$—W—$R^7$—X—Y;
$R^{2a}$ is selected from H; $C_1$-$C_8$ alkyl optionally substituted by one or more halogen atoms, OH, $C_1$-$C_4$ alkoxy, $C_3$-$C_7$ cycloalkyl or $C_3$-$C_7$ cycloalkyloxy; and $C_3$-$C_7$ cycloalkyl; or
$R^2$ and $R^{2a}$ taken together are oxo;
wherein either $R^1$ or $R^2$ is —X—Y, —W—$R^7$—X—Y, —S(O)$_2$—X—Y; or —S(O)$_2$—W—$R^7$—X—Y;
$R^3$ is selected from H; $C_1$-$C_8$ alkyl optionally substituted by one or more halogen atoms, OH, $C_1$-$C_4$ alkoxy, $C_3$-$C_7$ cycloalkyl or $C_3$-$C_7$ cycloalkyloxy; $C_1$-$C_4$ alkoxy; —($C_1$-$C_4$alkyl)-$NR^{19}R^{21}$; CN; halogen and $C_3$-$C_7$ cycloalkyl;

$R^{3a}$ is selected from H; $C_1$-$C_8$ alkyl optionally substituted by one or more halogen atoms, OH, $C_1$-$C_4$ alkoxy, $C_3$-$C_7$ cycloalkyl or $C_3$-$C_7$ cycloalkyloxy; and $C_3$-$C_7$ cycloalkyl; or $R^3$ and $R^{3a}$ taken together are oxo;

$R^4$ is selected from H; OH; $C_1$-$C_8$ alkyl optionally substituted by one or more halogen atoms, OH, $C_1$-$C_4$ alkoxy, $C_3$-$C_7$ cycloalkyl or $C_3$-$C_7$ cycloalkyloxy; $C_1$-$C_4$ alkoxy; OR'; —($C_0$-$C_4$alkyl)-$NR^{19}R^{21}$; CN; halogen; —($C_0$-$C_4$alkyl)-$C_6$-$C_{14}$aryl; —($C_0$-$C_4$alkyl)-4 to 14 membered heteroaryl; —C(=O)H; —C(=O)OH; —C(=O)$NR^{19}R^{21}$ and $C_3$-$C_7$ cycloalkyl;

$R^{4a}$ is selected from H; $C_1$-$C_8$ alkyl optionally substituted by one or more halogen atoms, OH, $C_1$-$C_4$ alkoxy, $C_3$-$C_7$ cycloalkyl or $C_3$-$C_7$ cycloalkyloxy; and $C_3$-$C_7$ cycloalkyl; or $R^4$ and $R^{4a}$ taken together are oxo;

$R^5$ and $R^6$ are independently selected from $C_6$-$C_{14}$ aryl and —($C_0$-$C_4$ alkyl)-4 to 14 membered heteroaryl, wherein the aryl and heteroaryl are each optionally substituted by one or more Z substituents;

W is $C_1$-$C_8$ alkylene optionally substituted by hydroxy, halogens or $C_1$-$C_4$ alkyl;

X is $C_1$-$C_8$ alkylene optionally substituted by hydroxy, halogens or $C_1$-$C_4$ alkyl;

Y is carboxy, alkoxycarbonyl, tetrazolyl, —C(=O)$NR^{19}R^{21}$ or —CONH—S(O)$_q$—$R^x$, wherein $R^x$ is phenyl, benzyl or —$NR^{19}R^{21}$;

q is 0, 1 or 2;

$R^7$ is a divalent moiety represented by —O—, —S—, —NHC(O)—, —$CH_2$=$CH_2$—, —$C_6$-$C_{14}$ aryl-D-; -3 to 14 membered heterocyclyl-D-, wherein the heterocyclyl contains at least one heteroatom selected from N, O and S, wherein D is O, S, NH or not present;

Z is independently OH, aryl, O-aryl, benzyl, O-benzyl, $C_1$-$C_6$ alkyl optionally substituted by one or more OH groups or $NH_2$ groups, $C_1$-$C_6$ alkyl optionally substituted by one or more halogen atoms, $C_1$-$C_6$ alkoxy optionally substituted by one or more OH groups, $C_1$-$C_6$ alkoxy optionally substituted by one or more halogen, $C_1$-$C_6$ alkoxy optionally substituted by $C_1$-$C_4$ alkoxy, $NR^{18}(SO_2)R^{21}$, $(SO_2)NR^{19}R^{21}$, $(SO_2)R^{21}$, $NR^{18}C(O)R^{21}$, $C(O)NR^{19}R^{21}$, $NR^{18}C(O)NR^{19}R^{21}$, $NR^{18}C(O)OR^{19}$, $NR^{19}R^{21}$, $C(O)OR^{19}$, $C(O)R^{19}$, $SR^{19}$, $OR^{19}$, oxo, CN, $NO_2$, halogen or a 3 to 14 membered heterocyclyl, wherein the heterocyclyl contains at least one heteroatom selected from N, O and S;

$R^{18}$ is independently H or $C_1$-$C_6$ alkyl;

$R^{19}$ and $R^{21}$ are each independently H; $C_1$-$C_8$ alkyl; $C_3$-$C_8$ cycloalkyl; $C_1$-$C_4$ alkoxy-$C_1$-$C_4$ alkyl; ($C_0$-$C_4$ alkyl)-aryl optionally substituted by one or more groups selected from $C_1$-$C_6$ alkyl, $C_1$-$C_6$ alkoxy and halogen; ($C_0$-$C_4$ alkyl)- 3- to 14-membered heterocyclyl, the heterocyclyl including one or more heteroatoms selected from N, O and S, optionally substituted by one or more groups selected from halogen, oxo, $C_1$-$C_6$ alkyl and C(O)$C_1$-$C_6$ alkyl; ($C_0$-$C_4$ alkyl)-O-aryl optionally substituted by one or more groups selected from $C_1$-$C_6$ alkyl, $C_1$-$C_6$ alkoxy and halogen; and ($C_0$-$C_4$ alkyl)-O-3- to 14-membered heterocyclyl, the heterocyclyl including one or more heteroatoms selected from N, O and S, optionally substituted by one or more groups selected from halogen, $C_1$-$C_6$ alkyl or C(O)$C_1$-$C_6$ alkyl; wherein the alkyl groups are optionally substituted by one or more halogen atoms, OH, $C_1$-$C_4$ alkoxy, C(O)$NH_2$, C(O)NH$C_1$-$C_6$ alkyl or C(O)N($C_1$-$C_6$ alkyl)$_2$; or $R^{19}$ and $R^{21}$ together with the nitrogen atom to which they attached form a 5- to 10-membered heterocyclyl, the heterocyclyl including one or more further heteroatoms selected from N, O and S, the heterocyclyl being optionally substituted by one or more substituents selected from OH; halogen; aryl; 5- to 10-membered heterocyclyl including one or more heteroatoms selected from N, O and S; $S(O)_2$-aryl; $S(O)_2$—$C_1$-$C_6$ alkyl; $C_1$-$C_6$ alkyl optionally substituted by one or more halogen atoms; $C_1$-$C_6$ alkoxy optionally substituted by one or more OH groups or $C_1$-$C_4$ alkoxy; and C(O)O$C_1$-$C_6$ alkyl, wherein the aryl and heterocyclyl substituent groups are themselves optionally substituted by $C_1$-$C_6$ alkyl, $C_1$-$C_6$ haloalkyl or $C_1$-$C_6$ alkoxy.

Embodiment 91

The compound according to embodiment 90, wherein wherein either $R^1$ or $R^2$ is —X—Y, —W—$R^7$—X—Y, —$S(O)_2$—X—Y; or —$S(O)_2$—W—$R^7$—X—Y;

W is $C_1$-$C_6$ alkylene optionally substituted by hydroxy, halogens or $C_1$-$C_4$ alkyl;

X is $C_1$-$C_6$ alkylene optionally substituted by hydroxy, halogens or $C_1$-$C_4$ alkyl;

Y is carboxy, alkoxycarbonyl, tetrazolyl, —C(=O)$NR^{19}R^{21}$ or —CONH—S(O)$_q$—$R^x$, wherein $R^x$ is phenyl, benzyl or —$NR^{19}R^{21}$;

q is 2;

$R^7$ is a divalent moiety represented by —$C_6$-$C_{14}$ aryl-D-; -3 to 14 membered heterocyclyl-D-, wherein the heterocyclyl contains at least one heteroatom selected from N, O and S, wherein D is O; and $R^{19}$ and $R^{21}$ are each independently H; $C_1$-$C_8$ alkyl.

Embodiment 92

The compound according to embodiment 90 or 91, wherein either $R^1$ or $R^2$ is —X—Y; or —W—$R^7$—X—Y;

W is $C_1$-$C_6$ alkylene optionally substituted by hydroxy, halogens or $C_1$-$C_4$ alkyl;

X is $C_1$-$C_6$ alkylene optionally substituted by hydroxy, halogens or $C_1$-$C_4$ alkyl;

Y is carboxy, alkoxycarbonyl, tetrazolyl, —C(=O)$NR^{19}R^{21}$ or —CONH—S(O)$_q$—$R^x$, wherein $R^x$ is phenyl, benzyl or —$NR^{19}R^{21}$;

q is 2;

$R^7$ is a divalent moiety represented by —$C_6$-$C_{14}$ aryl-D-; -3 to 14 membered heterocyclyl-D-, wherein the heterocyclyl contains at least one heteroatom selected from N, O and S, wherein D is O; and $R^{19}$ and $R^{21}$ are each independently H; $C_1$-$C_8$ alkyl.

Embodiment 93

The compound according to any one of embodiments 90 to 92, wherein either $R^1$ or $R^2$ is —X—Y; or —W—$R^7$—X—Y;

W is $C_1$-$C_6$ alkylene optionally substituted by hydroxy, halogens or $C_1$-$C_4$ alkyl;

X is $C_1$-$C_6$ alkylene optionally substituted by hydroxy, halogens or $C_1$-$C_4$ alkyl;

Y is carboxy; and $R^7$ is a divalent moiety represented by —$C_6$-$C_{14}$ aryl-D-; -3 to 14 membered heterocyclyl-D-, wherein the heterocyclyl contains at least one heteroatom selected from N, O and S, wherein D is O.

Embodiment 94

The compound according to embodiment 90, wherein either $R^1$ or $R^2$ is —$(CH_2)_m$—C(O)OR", or —$(CH_2)_m$—$R^7$—$(CH_2)_n$—C(O)OR";
m is 1, 2, 3, 4, 5, 6, 7 or 8;
n is 0, 1, 2 or 3;
R" is H or $C_1$-$C_4$ alkyl optionally substituted by one or more halogen atoms; and
$R^7$ is a divalent moiety represented by —$C_6$-$C_{14}$ aryl-D-; -3 to 14 membered heterocyclyl-D-, wherein the heterocyclyl contains at least one heteroatom selected from N, O and S, wherein D is O.

Embodiment 95

The compound according to embodiments 94, wherein either $R^1$ or $R^2$ is —$(CH_2)_m$—C(O)OR";
m is 3, 4, 5, 6, 7 or 8; and
R" is H or $C_1$-$C_4$ alkyl optionally substituted by one or more halogen atoms.

Embodiment 96

The compound according to any of embodiments 94 or 95, wherein
either $R^1$ or $R^2$ is —$(CH_2)_m$—C(O)OR";
R" is H; and
m is 4, 5 or 6.

Embodiment 97

The compound according to embodiment 90, wherein either $R^1$ or $R^2$ is

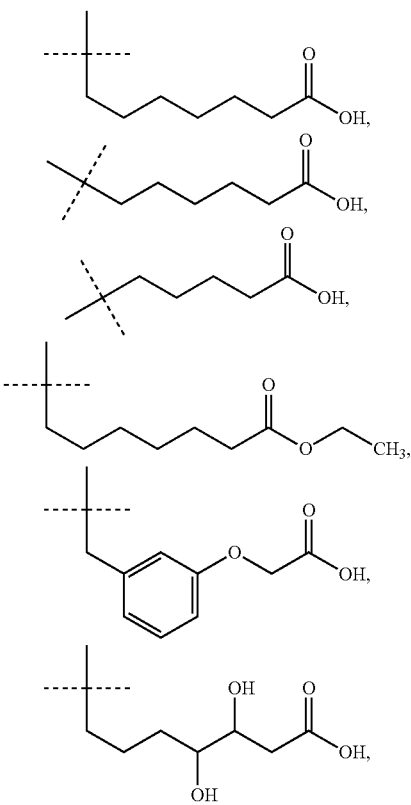

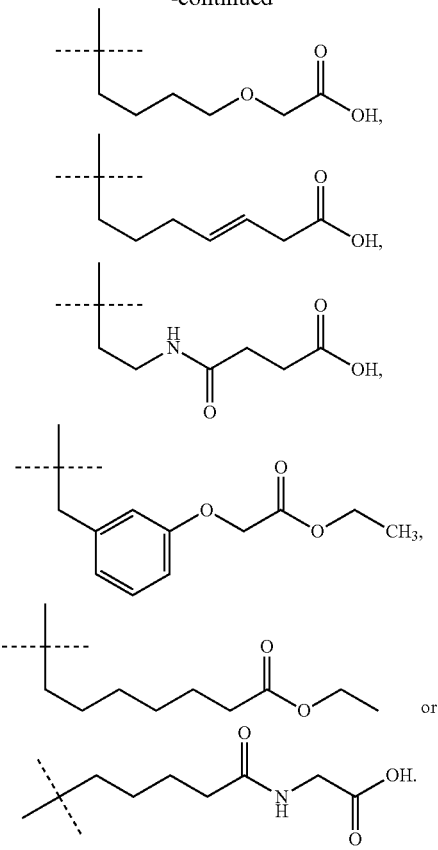

Embodiment 99

The compound according to any one of embodiments 90 to 97, wherein
$R^2$ is selected from H, $C_1$-$C_8$ alkyl optionally substituted by one or more halogen atoms, and $C_3$-$C_7$cycloalkyl;
$R^{2a}$ is H; or
$R^2$ and $R^{2a}$ together are oxo;
R' is H, $C_1$-$C_4$ alkyl.

Embodiment 100

The compound according to embodiment 98, wherein
$R^2$ is selected from H, $C_1$-$C_8$ alkyl optionally substituted by one or more halogen atoms, and $C_3$-$C_7$cycloalkyl.

Embodiment 101

The compound according to embodiment 99, wherein
$R^2$ is selected from H, $C_1$-$C_4$ alkyl optionally substituted by one or more halogen atoms, and $C_3$-$C_7$cycloalkyl.

Embodiment 102

The compound according to embodiment 100, wherein $R^2$ is H.

Embodiment 103

The compound according to any of embodiments 90-102, wherein
R$^3$ is independently selected from H; C$_1$-C$_8$ alkyl optionally substituted by one or more halogen atoms or OH; —(C$_1$-C$_4$ alkyl)-NR$^{19}$R$^{21}$; and C$_3$-C$_7$ cycloalkyl; or R$^3$ and R$^{3a}$ taken together are oxo.

Embodiment 104

The compound according to any of embodiments 90-103, wherein
R$^3$ and R$^{3a}$ are independently selected from H; C$_1$-C$_4$ alkyl optionally substituted by one or more halogen atoms or OH; or R$^3$ and R$^{3a}$ taken together are oxo.

Embodiment 105

The compound according to any of embodiments 90-104, wherein
R$^4$ and R$^{4a}$ are independently selected from H; C$_1$-C$_8$ alkyl optionally substituted by one or more halogen atoms or OH; C$_1$-C$_4$ alkoxy; OR'; —(C$_0$-C$_4$alkyl)-NR$^{19}$R$^{21}$; CN; halogen; —(C$_0$-C$_4$alkyl)-C$_6$-C$_{14}$aryl; —(C$_0$-C$_4$alkyl)-4 to 14 membered heteroaryl; —C(=O)H; —C(=O)OH; —C(=O)NR$^{19}$R$^{21}$ and C$_3$-C$_7$ cycloalkyl.

Embodiment 106

The compound according to any one of embodiments 90-105, wherein
R$^5$ and R$^6$ are independently selected from C$_6$-C$_{14}$ aryl and 5 to 6 membered heteroaryl, wherein the heteroaryl contains at least one heteroatom selected from N, O and S, wherein the aryl and heteroaryl are each optionally substituted by one or more Z substituents.

Embodiment 107

The compound according to any one of embodiments 90 to 105, wherein
R$^5$ and R$^6$ are independently selected from phenyl; 2-pyridyl, 3-pyridyl, or 4-pyridyl, wherein the phenyl, 2-pyridyl, 3-pyridyl, and 4-pyridyl are each optionally substituted by one or more Z substituents.

Embodiment 108

The compound according to any one of the embodiments 90 to 107, wherein
R$^5$ and R$^6$ are independently selected from phenyl optionally substituted by OH, C$_1$-C$_4$ alkyl optionally substituted by one or more OH groups or NH$_2$ groups; C$_1$-C$_4$ alkyl optionally substituted by one or more halogen atoms; C$_1$-C$_4$ alkoxy optionally substituted by one or more OH groups or C$_1$-C$_4$ alkoxy; NR$^{19}$R$^{21}$; C(O)OR$^{19}$; C(O)R$^{19}$; SR$^{19}$; OR$^{19}$; CN; NO$_2$; and halogen.

Embodiment 109

The compound according to any one of embodiments 90 to 108, wherein
R$^5$ and R$^6$ are independently selected from phenyl optionally substituted by C$_1$-C$_4$ alkyl optionally substituted by one or more OH groups or NH$_2$ groups; C$_1$-C$_4$ alkyl optionally substituted by one or more halogen atoms; C$_1$-C$_4$ alkoxy optionally substituted by one or more OH groups or C$_1$-C$_4$ alkoxy; and halogen.

Embodiment 110

The compound according to any one of embodiments 90 to 109, wherein
R$^5$ and R$^6$ are independently selected from phenyl optionally substituted by C$_1$-C$_4$ alkoxy or halogen, and C$_1$-C$_4$ alkyl optionally substituted by one or more halogen atoms.

Embodiment 111

The compound according to any one of embodiments 90 to 110, wherein
R$^5$ and R$^6$ are independently selected from phenyl optionally substituted by methyl, ethyl, trifluoromethyl, methoxy or halogen.

Embodiment 112

The compound according to any one of embodiments 90 to 111, wherein
R$^5$ is

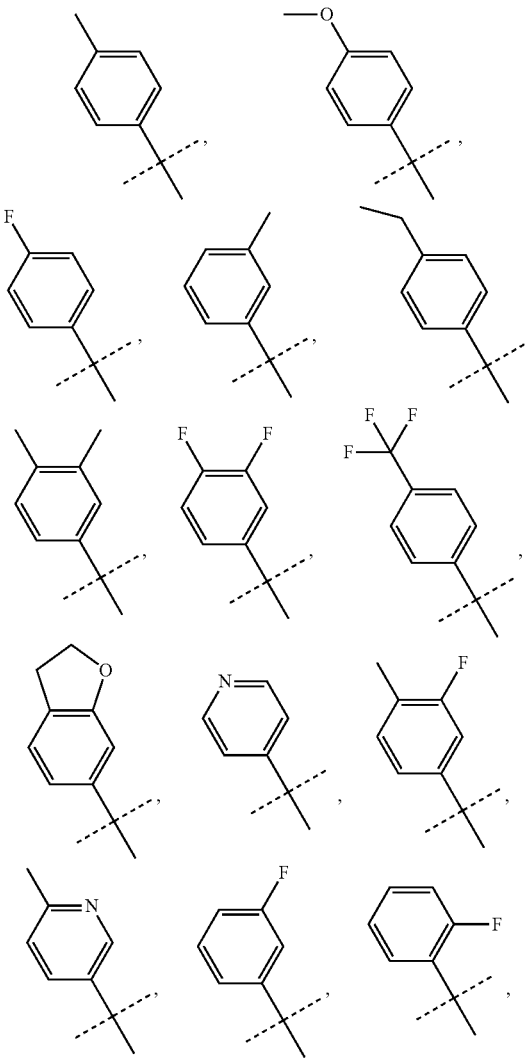

41
-continued

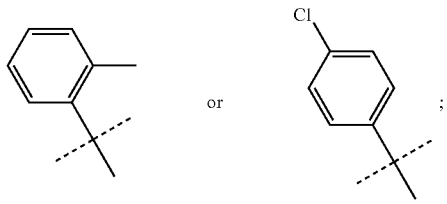

and
R⁶ is

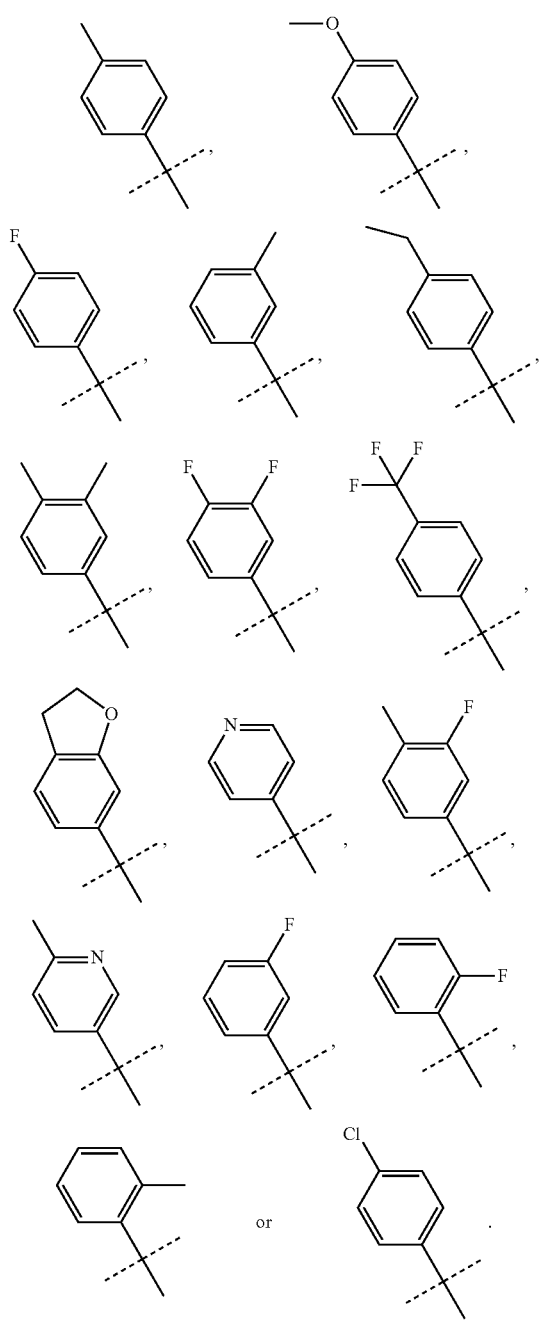

42

Embodiment 113

The compound according to any one of embodiments 90 to 112, wherein formula Ib has the following stereochemistry:

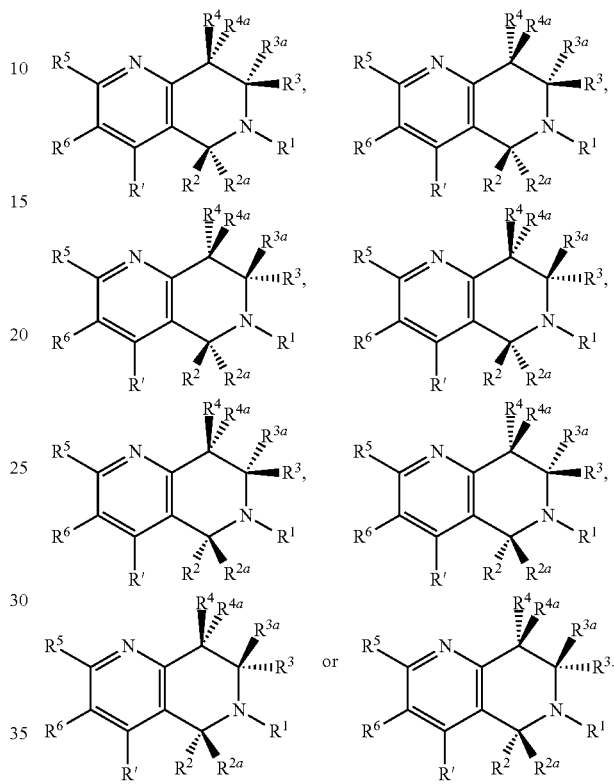

Embodiment 114

The compound according to any one of embodiments 90 to 113, or a pharmaceutically acceptable salt thereof, for use as a medicament.

Embodiment 115

The compound according to any one of embodiments 90 to 113, or a pharmaceutically acceptable salt thereof, for use in the treatment of a disorder or disease mediated by the IP receptor.

Embodiment 116

The compound according to any one of embodiments 90 to 113, or a pharmaceutically acceptable salt thereof, for use in the treatment of a disorder or disease selected from PAH, disorders in need of antiplatelet therapy, atherosclerosis, asthma, COPD, hyperglycemia, inflammatory disease and fibrotic diseases.

Embodiment 117

The compound according to any one of embodiments 90 to 113, or a pharmaceutically acceptable salt thereof, for use in the treatment of a disorder or disease selected from PAH, atherosclerosis, asthma, COPD, hyperglycemia and fibrotic diseases.

Embodiment 118

The compound according to any one of embodiments 90 to 113, or a pharmaceutically acceptable salt thereof, for use in the treatment of a disorder or disease selected from PAH, asthma, COPD and cystic fibrosis.

Embodiment 119

The compound according to any one of embodiments 90 to 113, or a pharmaceutically acceptable salt thereof, for use in the treatment of a disorder or disease selected from PAH or COPD.

Embodiment 120

The compound according to any one of embodiments 90 to 113, or a pharmaceutically acceptable salt thereof, for use in the treatment of PAH.

Embodiment 121

A pharmaceutical composition, comprising:
a therapeutically effective amount of the compound according to any one of embodiments 90 to 113, or a pharmaceutically acceptable salt thereof, and one or more pharmaceutically acceptable carriers.

Embodiment 122

A pharmaceutical combination, comprising:
a therapeutically effective amount of the compound according to any one of embodiments 90 to 113, or a pharmaceutically acceptable salt thereof, and a second active agent.

Embodiment 123

A method of treating pulmonary arterial hypertension in a patient in need thereof, comprising:
administering to the subject in need thereof a therapeutically effective amount of the compound according to any one of embodiments 90 to 113, or a pharmaceutically acceptable salt thereof.

Embodiment 124

Use of a compound according to any one of embodiments 90 to 113, or a pharmaceutically acceptable salt thereof, in the manufacture of a medicament for the treatment of a disorder or disease mediated by the IP receptor.

Embodiment 125

The compound according to any one of embodiments 90 to 113, or a pharmaceutically acceptable salt thereof, for use in the treatment of a disorder or disease selected from PAH, disorders in need of antiplatelet therapy, atherosclerosis, asthma, COPD, hyperglycemia, inflammatory disease and fibrotic diseases.

Embodiment 126

Use of a compound according to any one of embodiments 90 to 113, or a pharmaceutically acceptable salt thereof, in the manufacture of a medicament for the treatment of a disorder or disease selected from PAH, atherosclerosis, asthma, COPD, hyperglycemia and fibrotic diseases.

Embodiment 127

Use of a compound according to any one of embodiments 90 to 113, or a pharmaceutically acceptable salt thereof, in the manufacture of a medicament for the treatment of a disorder or disease selected from PAH, asthma, COPD and cystic fibrosis.

Embodiment 128

Use of a compound according to any one of embodiments 90 to 113, or a pharmaceutically acceptable salt thereof, in the manufacture of a medicament for the treatment of a disorder or disease selected from PAH or COPD.

Embodiment 129

Use of a compound according to any one of embodiments 90 to 113, or a pharmaceutically acceptable salt thereof, in the manufacture of a medicament for the treatment of PAH.

Embodiment 130

Use of a compound according to any one of embodiments 90 to 113, or a pharmaceutically acceptable salt thereof, for the treatment of pulmonary arterial hypertension.

Embodiment 131

A method for the prevention or treatment of a condition affected by activation of the IP receptor, comprising:
administering an effective amount to activate the IP receptor of at least one compound according to any of embodiments 90 to 113 to a subject in need of such treatment.

Embodiment 140

A compound represented by formula

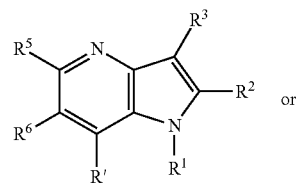

(Ia)

or

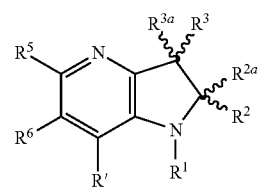

(Ib)

or a pharmaceutically acceptable salt thereof, wherein
R' is H, $C_1$-$C_8$ alkyl optionally substituted by one or more halogen atoms;
$R^1$ is selected from H; $C_1$-$C_8$ alkyl optionally substituted by one or more halogen atoms, OH, $C_1$-$C_4$ alkoxy, $C_3$-$C_7$ cycloalkyl or $C_3$-$C_7$ cycloalkyloxy; —($C_2$-$C_4$ alkyl)-$NR^{19}R^{21}$ and $C_3$-$C_7$ cycloalkyl; or $R^1$ is —X—Y; or
$R^1$ is —W—$R^7$—X—Y; or
$R^1$ is —S(O)$_2$—X—Y; or
$R^1$ is —S(O)$_2$—W—$R^7$—X—Y;

$R^2$ is selected from H; $C_1$-$C_8$ alkyl optionally substituted by one or more halogen atoms, OH, $C_1$-$C_4$ alkoxy, $C_3$-$C_7$ cycloalkyl or $C_3$-$C_7$ cycloalkyloxy; $C_1$-$C_4$ alkoxy; —($C_0$-$C_4$ alkyl)-$NR^{19}R^{21}$ and $C_3$-$C_7$ cycloalkyl; or $R^2$ is —X—Y; or
$R^2$ is —W—$R^7$—X—Y; or
$R^2$ is —S(O)$_2$—X—Y; or
$R^2$ is —S(O)$_2$—W—$R^7$—X—Y;

$R^{2a}$ is selected from H; $C_1$-$C_8$ alkyl optionally substituted by one or more halogen atoms, OH, $C_1$-$C_4$ alkoxy, $C_3$-$C_7$ cycloalkyl or $C_3$-$C_7$ cycloalkyloxy; and $C_3$-$C_7$ cycloalkyl; or $R^2$ and $R^{2a}$ taken together are oxo;

wherein either $R^1$ or $R^2$ is —X—Y, —W—$R^7$—X—Y, —S(O)$_2$—X—Y; or —S(O)$_2$—W—$R^7$—X—Y;

$R^3$ is independently selected from H; $C_1$-$C_8$ alkyl optionally substituted by one or more halogen atoms, OH, $C_1$-$C_4$ alkoxy, $C_3$-$C_7$ cycloalkyl or $C_3$-$C_7$ cycloalkyloxy; —OH; OR'; —($C_0$-$C_4$alkyl)-$NR^{19}R^{21}$; CN; halogen; —($C_0$-$C_4$alkyl)-$C_6$-$C_{14}$aryl; —($C_0$-$C_4$alkyl)-4 to 14 membered heteroaryl; —C(=O)H; —C(=O)OH; —C(=O)$NR^{19}R^{21}$ and $C_3$-$C_7$ cycloalky, wherein the aryl and heteroaryl are optionally substituted by one or more substituents independently selected from OH, $C_1$-$C_4$ alkyl, $C_1$-$C_4$ alkoxy, halogens and $C_1$-$C_4$ haloalkyl;

$R^{3a}$ is selected from H; $C_1$-$C_8$ alkyl optionally substituted by one or more halogen atoms, OH, $C_1$-$C_4$ alkoxy, $C_3$-$C_7$ cycloalkyl or $C_3$-$C_7$ cycloalkyloxy; and $C_3$-$C_7$ cycloalkyl; or $R^3$ and $R^{3a}$ taken together are oxo;

$R^5$ and $R^6$ are independently selected from —($C_0$-$C_4$ alkyl)-$C_6$-$C_{14}$ aryl and —($C_0$-$C_4$ alkyl)-4 to 14 membered heteroaryl, wherein the aryl and heteroaryl are each optionally substituted by one or more Z substituents;

W is $C_1$-$C_8$ alkylene optionally substituted by hydroxy, halogens or $C_1$-$C_4$ alkyl;

X is $C_1$-$C_8$ alkylene optionally substituted by hydroxy, halogens or $C_1$-$C_4$ alkyl;

Y is carboxy, $C_1$-$C_4$-alkoxycarbonyl, tetrazolyl, —C(=O)$NR^{19}R^{21}$ or —CONH—S(O)$_q$—$R^x$, wherein $R^x$ is phenyl, benzyl or —$NR^{19}R^{21}$;

q is 0, 1 or 2;

$R^7$ is a divalent moiety represented by —O—, —S—, —NHC(O)—, —CH$_2$=CH$_2$—, —$C_6$-$C_{14}$ aryl-D-; -3 to 14 membered heterocyclyl-D-, wherein the heterocyclyl contains at least one heteroatom selected from N, O and S, wherein D is O, S, NH or not present;

Z is independently OH, aryl, O-aryl, benzyl, O-benzyl, $C_1$-$C_6$ alkyl optionally substituted by one or more OH groups or NH$_2$ groups, $C_1$-$C_6$ alkyl optionally substituted by one or more halogen atoms, $C_1$-$C_6$ alkoxy optionally substituted by one or more OH groups, $C_1$-$C_6$ alkoxy optionally substituted by one or more halogen, $C_1$-$C_6$ alkoxy optionally substituted by $C_1$-$C_4$ alkoxy, $NR^{18}(SO_2)R^{21}$, (SO$_2$)$NR^{19}R^{21}$, (SO$_2$)$R^{21}$, $NR^{18}C(O)R^{21}$, C(O)$NR^{19}R^{21}$, $NR^{18}C(O)NR^{19}R^{21}$, $NR^{18}C(O)OR^{19}$, $NR^{19}R^{21}$, C(O)$OR^{19}$, C(O)$R^{19}$, $SR^{19}$, $OR^{19}$, oxo, CN, NO$_2$, halogen or a 3 to 14 membered heterocyclyl, wherein the heterocyclyl contains at least one heteroatom selected from N, O and S;

$R^{18}$ is independently H or $C_1$-$C_6$ alkyl;

$R^{19}$ and $R^{21}$ are each independently H; $C_1$-$C_8$ alkyl; $C_3$-$C_8$ cycloalkyl; $C_1$-$C_4$ alkoxy-$C_1$-$C_4$ alkyl; —($C_1$-$C_4$ alkyl)-carboxy; ($C_0$-$C_4$ alkyl)-aryl optionally substituted by one or more groups selected from $C_1$-$C_6$ alkyl, $C_1$-$C_6$ alkoxy and halogen; ($C_0$-$C_4$ alkyl)- 3- to 14-membered heterocyclyl, the heterocyclyl including one or more heteroatoms selected from N, O and S, optionally substituted by one or more groups selected from halogen, oxo, $C_1$-$C_6$ alkyl and C(O) $C_1$-$C_6$ alkyl; ($C_0$-$C_4$ alkyl)-O-aryl optionally substituted by one or more groups selected from $C_1$-$C_6$ alkyl, $C_1$-$C_6$ alkoxy and halogen; and ($C_0$-$C_4$ alkyl)- O-3- to 14-membered heterocyclyl, the heterocyclyl including one or more heteroatoms selected from N, O and S, optionally substituted by one or more groups selected from halogen, $C_1$-$C_6$ alkyl or C(O)$C_1$-$C_6$ alkyl; wherein the alkyl groups are optionally substituted by one or more halogen atoms, OH, $C_1$-$C_4$ alkoxy, C(O)NH$_2$, C(O)NHC$_1$-$C_6$ alkyl or C(O)N($C_1$-$C_6$ alkyl)$_2$; or $R^{19}$ and $R^{21}$ together with the nitrogen atom to which they attached form a 5- to 10-membered heterocyclyl, the heterocyclyl including one or more further heteroatoms selected from N, O and S, the heterocyclyl being optionally substituted by one or more substituents selected from OH; halogen; aryl; 5- to 10-membered heterocyclyl including one or more heteroatoms selected from N, O and S; S(O)$_2$-aryl; S(O)$_2$—$C_1$-$C_6$ alkyl; $C_1$-$C_6$ alkyl optionally substituted by one or more halogen atoms; $C_1$-$C_6$ alkoxy optionally substituted by one or more OH groups or $C_1$-$C_4$ alkoxy; and C(O)O$C_1$-$C_6$ alkyl, wherein the aryl and heterocyclyl substituent groups are themselves optionally substituted by $C_1$-$C_6$ alkyl, $C_1$-$C_6$ haloalkyl or $C_1$-$C_6$ alkoxy.

Embodiment 141

The compound according to embodiment 140, wherein
wherein either $R^1$ or $R^2$ is —X—Y, —W—$R^7$—X—Y, —S(O)$_2$—X—Y; or —S(O)$_2$—W—$R^7$—X—Y;
W is $C_1$-$C_6$ alkylene optionally substituted by hydroxy, halogens or $C_1$-$C_4$ alkyl;
X is $C_1$-$C_6$ alkylene optionally substituted by hydroxy, halogens or $C_1$-$C_4$ alkyl;
Y is carboxy, $C_1$-$C_4$-alkoxycarbonyl, tetrazolyl, —C(=O)$NR^{19}R^{21}$ or —CONH—S(O)$_q$—$R^x$, wherein $R^x$ is phenyl, benzyl or —$NR^{19}R^{21}$;
q is 2;
$R^7$ is a divalent moiety represented by —$C_6$-$C_{14}$ aryl-D-; -3 to 14 membered heterocyclyl-D-, wherein the heterocyclyl contains at least one heteroatom selected from N, O and S, wherein D is O; and
$R^{19}$ and $R^{21}$ are each independently H; $C_1$-$C_8$ alkyl.

Embodiment 142

The compound according to embodiment 140 or 141, wherein
either $R^1$ or $R^2$ is —X—Y; or —W—$R^7$—X—Y;
W is $C_1$-$C_6$ alkylene optionally substituted by hydroxy, halogens or $C_1$-$C_4$ alkyl;
X is $C_1$-$C_6$ alkylene optionally substituted by hydroxy, halogens or $C_1$-$C_4$ alkyl;
Y is carboxy, $C_1$-$C_4$-alkoxycarbonyl, tetrazolyl, —C(=O)$NR^{19}R^{21}$ or —CONH—S(O)$_q$—$R^x$, wherein $R^x$ is phenyl, benzyl or —$NR^{19}R^{21}$;
q is 2;
$R^7$ is a divalent moiety represented by —$C_6$-$C_{14}$ aryl-D-; -3 to 14 membered heterocyclyl-D-, wherein the heterocyclyl contains at least one heteroatom selected from N, O and S, wherein D is O; and
$R^{19}$ and $R^{21}$ are each independently H; $C_1$-$C_8$ alkyl.

Embodiment 143

The compound according to any one of embodiments 140 to 142, wherein
either $R^1$ or $R^2$ is —X—Y; or —W—$R^7$—X—Y;
W is $C_1$-$C_6$ alkylene optionally substituted by hydroxy, halogens or $C_1$-$C_4$ alkyl;
X is $C_1$-$C_6$ alkylene optionally substituted by hydroxy, halogens or $C_1$-$C_4$ alkyl;
Y is —C(O)OH; and
$R^7$ is a divalent moiety represented by —$C_6$-$C_{14}$ aryl-D-; -3 to 14 membered heterocyclyl-D-, wherein the heterocyclyl contains at least one heteroatom selected from N, O and S, wherein D is O.

Embodiment 144

The compound according to embodiment 140, wherein
either $R^1$ or $R^2$ is —$(CH_2)_m$—C(O)OR", or —$(CH_2)_m$—$R^7$—$(CH_2)_n$—C(O)OR";
m is 1, 2, 3, 4, 5, 6, 7 or 8;
n is 0, 1, 2 or 3;
R" is H or $C_1$-$C_4$ alkyl optionally substituted by one or more halogen atoms; and
$R^7$ is a divalent moiety represented by —$C_6$-$C_{14}$ aryl-D-; -3 to 14 membered heterocyclyl-D-, wherein the heterocyclyl contains at least one heteroatom selected from N, O and S, wherein D is O.

Embodiment 145

The compound according to embodiments 144, wherein
either $R^1$ or $R^2$ is —$(CH_2)_m$—C(O)OR";
m is 3, 4, 5, 6, 7 or 8; and
R" is H or $C_1$-$C_4$ alkyl optionally substituted by one or more halogen atoms.

Embodiment 146

The compound according to any one of embodiments 144 or 145, wherein
either $R^1$ or $R^2$ is —$(CH_2)_m$—C(O)OR";
R" is H; and
m is 4, 5 or 6.

Embodiment 147

The compound according to embodiment 140, wherein either $R^1$ or $R^2$ is

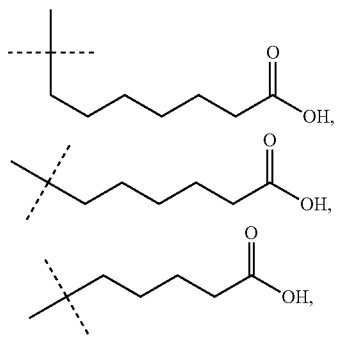

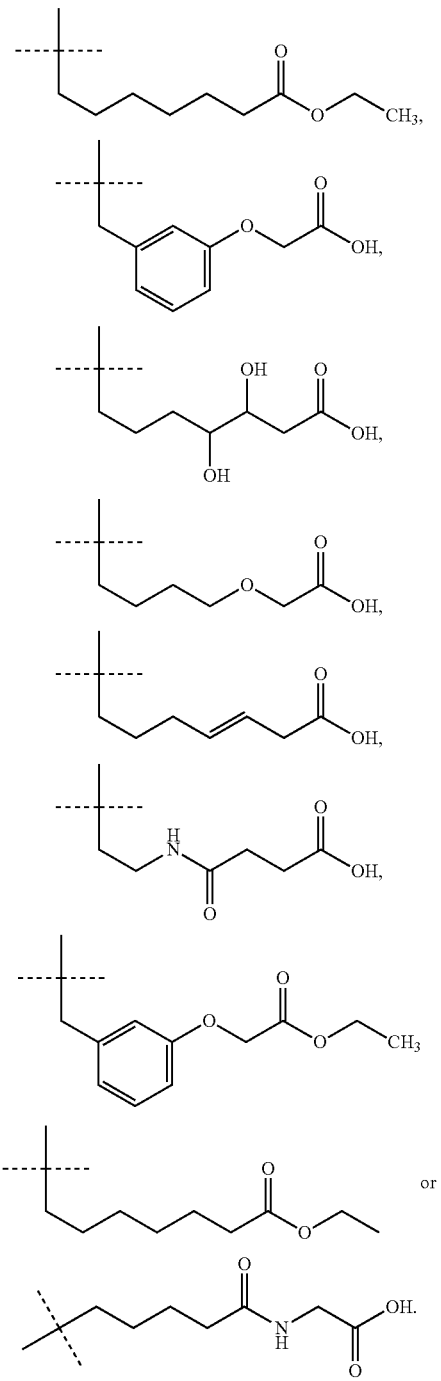

Embodiment 148

The compound according to any one of embodiments 140 to 147, wherein
$R^2$ is H, $C_1$-$C_8$ alkyl optionally substituted by one or more halogen atoms, $C_1$-$C_4$ alkoxy, $C_3$-$C_7$ cycloalkyl;
$R^{2a}$ is H; or
$R^2$ and $R^{2a}$ together are oxo;
R' is H, $C_1$-$C_4$ alkyl.

Embodiment 149

The compound according to embodiment 148, wherein $R^2$ is H, $C_1$-$C_8$ alkyl optionally substituted by one or more halogen atoms, $C_1$-$C_4$ alkoxy, $C_3$-$C_7$ cycloalkyl.

Embodiment 150

The compound according to embodiment 149, wherein $R^2$ is H.

Embodiment 151

The compound according to any one of embodiments 140-150, wherein
$R^3$ and $R^{3a}$ are independently selected from H; $C_1$-$C_4$ alkyl optionally substituted by one or more halogen atoms or OH; —C(=O)H; —C(=O)H; —($C_0$-$C_4$alkyl)-$NR^{19}R^{21}$ and OH; or $R^3$ and $R^{3a}$ taken together are oxo.

Embodiment 152

The compound according to any one of embodiments 140-151, wherein
$R^3$ and $R^{3a}$ are independently selected from H; $C_1$-$C_4$ alkyl optionally substituted by one or more halogen atoms or OH; —C(=O)H and OH; or $R^3$ and $R^{3a}$ taken together are oxo.

Embodiment 153

The compound according to any one of embodiments 140-152, wherein
$R^5$ and $R^6$ are independently selected from $C_6$-$C_{14}$ aryl and 5 to 6 membered heteroaryl, wherein the heteroaryl contains at least one heteroatom selected from N, O and S, wherein the aryl and heteroaryl are each optionally substituted by one or more Z substituents.

Embodiment 154

The compound according to any one of embodiments 140 to 153, wherein
$R^5$ and $R^6$ are independently selected from phenyl; 2-pyridyl, 3-pyridyl, or 4-pyridyl, wherein the phenyl, 2-pyridyl, 3-pyridyl, and 4-pyridyl are each optionally substituted by one or more Z substituents.

Embodiment 155

The compound according to any one of the embodiments 140 to 154, wherein
$R^5$ and $R^6$ are independently selected from phenyl optionally substituted by OH, $C_1$-$C_4$ alkyl optionally substituted by one or more OH groups or $NH_2$ groups; $C_1$-$C_4$ alkyl optionally substituted by one or more halogen atoms; $C_1$-$C_4$ alkoxy optionally substituted by one or more OH groups or $C_1$-$C_4$ alkoxy; $NR^{19}R^{21}$; C(O)$OR^{19}$; C(O)$R^{19}$; $SR^{19}$; $OR^{19}$; CN; $NO_2$; and halogen.

Embodiment 156

The compound according to any one of embodiments 140 to 155, wherein
$R^5$ and $R^6$ are independently selected from phenyl optionally substituted by $C_1$-$C_4$ alkyl optionally substituted by one or more OH groups or $NH_2$ groups; $C_1$-$C_4$ alkyl optionally substituted by one or more halogen atoms; $C_1$-$C_4$ alkoxy optionally substituted by one or more OH groups or $C_1$-$C_4$ alkoxy; and halogen.

Embodiment 157

The compound according to any one of embodiments 140 to 156, wherein
$R^5$ and $R^6$ are independently selected from phenyl optionally substituted by $C_1$-$C_4$ alkoxy or halogen, and $C_1$-$C_4$ alkyl optionally substituted by one or more halogen atoms.

Embodiment 158

The compound according to any one of embodiments 140 to 157, wherein
$R^5$ and $R^6$ are independently selected from phenyl optionally substituted by methyl, ethyl, trifluoromethyl, methoxy or halogen.

Embodiment 159

The compound according to any one of embodiments 140 to 158, wherein
$R^5$ is

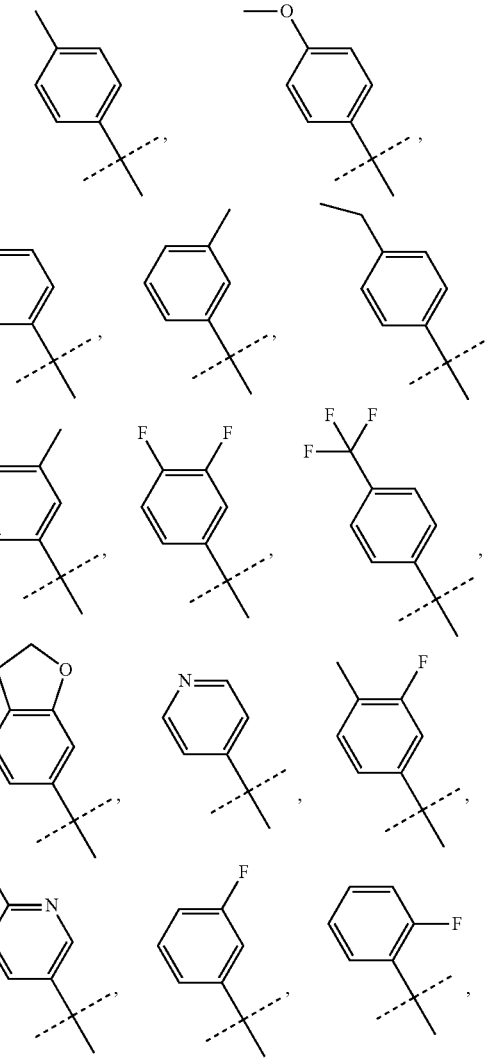

-continued

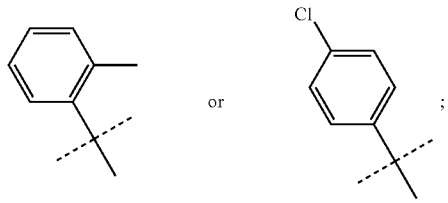

and

R⁶ is

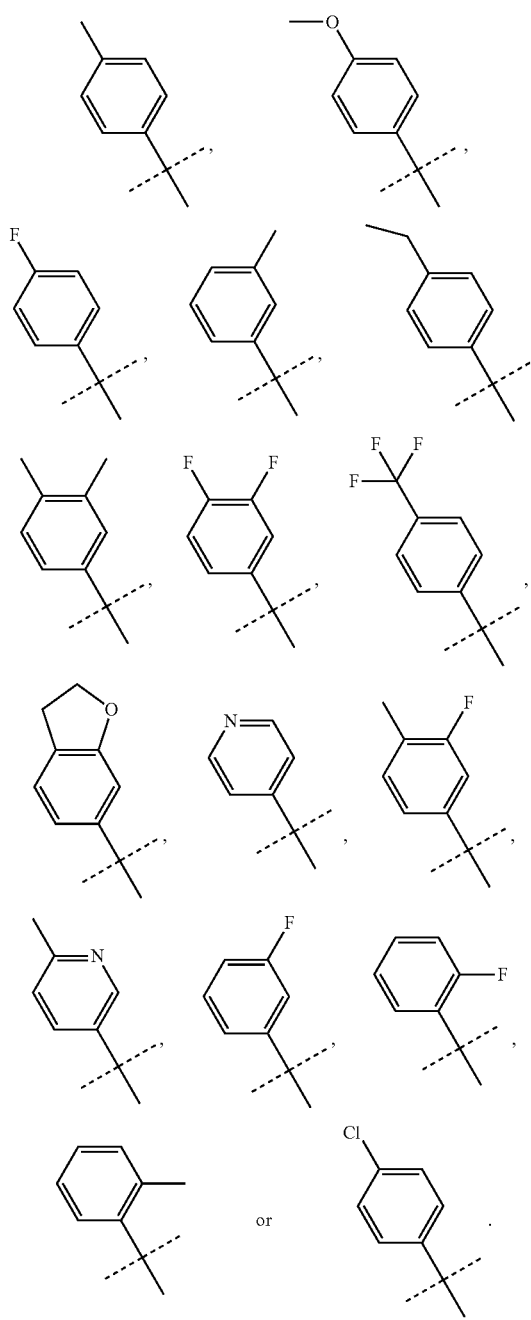

Embodiment 160

The compound according to any one of embodiments 140 to 159, wherein formula Ib has the following stereochemistry:

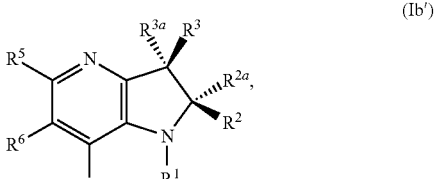
(Ib′)

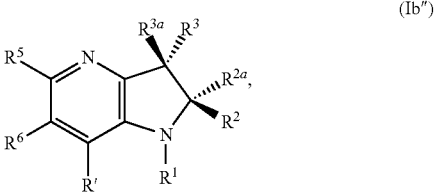
(Ib″)

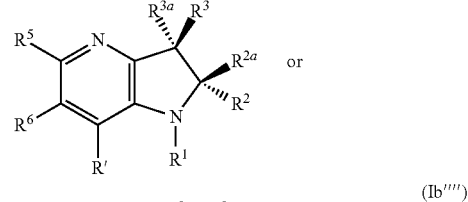
(Ib‴) or

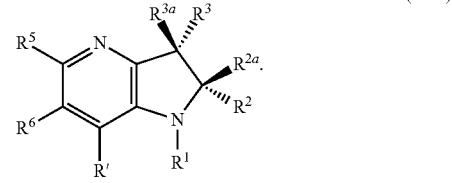
(Ib⁗).

Embodiment 161

The compound according to any one of embodiments 140 to 160, or a pharmaceutically acceptable salt thereof, for use as a medicament.

Embodiment 162

The compound according to any one of embodiments 140 to 160, or a pharmaceutically acceptable salt thereof, for use in the treatment of a disorder or disease mediated by the IP receptor.

Embodiment 163

The compound according to any one of embodiments 140 to 160, or a pharmaceutically acceptable salt thereof, for use in the treatment of a disorder or disease selected from PAH, disorders in need of antiplatelet therapy, atherosclerosis, asthma, COPD, hyperglycemia, inflammatory disease and fibrotic diseases.

Embodiment 164

The compound according to any one of embodiments 140 to 160, or a pharmaceutically acceptable salt thereof, for use in the treatment of a disorder or disease selected from PAH, atherosclerosis, asthma, COPD, hyperglycemia and fibrotic diseases.

Embodiment 165

The compound according to any one of embodiments 140 to 160, or a pharmaceutically acceptable salt thereof, for use in the treatment of a disorder or disease selected from PAH, asthma, COPD and cystic fibrosis.

Embodiment 166

The compound according to any one of embodiments 140 to 160, or a pharmaceutically acceptable salt thereof, for use in the treatment of a disorder or disease selected from PAH or COPD.

Embodiment 167

The compound according to any one of embodiments 140 to 160, or a pharmaceutically acceptable salt thereof, for use in the treatment of PAH.

Embodiment 168

A pharmaceutical composition, comprising:
a therapeutically effective amount of the compound according to any one of embodiments 140 to 160, or a pharmaceutically acceptable salt thereof, and one or more pharmaceutically acceptable carriers.

Embodiment 169

A pharmaceutical combination, comprising:
a therapeutically effective amount of the compound according to any one of embodiments 140 to 160, or a pharmaceutically acceptable salt thereof, and a second active agent.

Embodiment 170

Use of a compound according to any one of embodiments 140 to 160, or a pharmaceutically acceptable salt thereof, in the manufacture of a medicament for the treatment of a disorder or disease mediated by the IP receptor.

Embodiment 171

Use of a compound according to any one of embodiments 140 to 160, or a pharmaceutically acceptable salt thereof, in the manufacture of a medicament for the treatment of a disorder or disease selected from PAH, atherosclerosis, asthma, COPD, hyperglycemia and fibrotic diseases.

Embodiment 172

Use of a compound according to any one of embodiments 140 to 160, or a pharmaceutically acceptable salt thereof, in the manufacture of a medicament for the treatment of a disorder or disease selected from PAH, asthma, COPD and cystic fibrosis.

Embodiment 173

Use of a compound according to any one of embodiments 140 to 160, or a pharmaceutically acceptable salt thereof, in the manufacture of a medicament for the treatment of a disorder or disease selected from PAH or COPD.

Embodiment 174

Use of a compound according to any one of embodiments 140 to 160, or a pharmaceutically acceptable salt thereof, in the manufacture of a medicament for the treatment of PAH.

Embodiment 175

Use of a compound according to any one of embodiments 140 to 160, or a pharmaceutically acceptable salt thereof, for the treatment of pulmonary arterial hypertension.

Embodiment 176

A method for the prevention or treatment of a condition affected by activation of the IP receptor, comprising:
administering an effective amount to activate the IP receptor of at least one compound according to any of embodiments 140 to 160 to a subject in need of such treatment.

Embodiment 177

A method of treating a disorder or disease selected from PAH, disorders in need of antiplatelet therapy, atherosclerosis, asthma, COPD, hyperglycemia, inflammatory disease and fibrotic diseases in a patient in need thereof, comprising:
administering to the subject in need thereof a therapeutically effective amount of the compound according to any one of embodiments 140 to 160, or a pharmaceutically acceptable salt thereof.

DEFINITIONS

Terms used in the specification have the following meanings:

"Optionally substituted" means the group referred to can be substituted at one or more positions by any one or any combination of the radicals listed thereafter.

"Optionally substituted by one or more Z groups" denotes that the relevant group may include one or more substituents, each independently selected from the groups included within the definition of Z. Thus, where there are two or more Z group substituents, these may be the same or different.

"Halo" or "halogen", as used herein, may be fluorine, chlorine, bromine or iodine.

"$C_1$-$C_8$-Alkyl", as used herein, denotes straight chain or branched alkyl having 1-8 carbon atoms. If a different number of carbon atoms is specified, such as $C_6$ or $C_3$, then the definition is to be amended accordingly, such as "$C_1$-$C_4$-Alkyl" will represent methyl, ethyl, propyl, isopropyl, butyl, isobutyl, sec-butyl and tert-butyl.

"$C_1$-$C_8$-Alkoxy", as used herein, denotes straight chain or branched alkoxy having 1-8 carbon atoms. If a different number of carbon atoms is specified, such as $C_6$ or $C_3$, then the definition is to be amended accordingly, such as "$C_1$-$C_4$-Alkoxy" will represent methoxy, ethoxy, propoxy, isopropoxy, butoxy, isobutoxy, sec-butoxy and tert-butoxy.

"$C_1$-$C_4$-Haloalkyl", as used herein, denotes straight chain or branched alkyl having 1-4 carbon atoms with at least one hydrogen substituted with a halogen. If a different number of carbon atoms is specified, such as $C_6$ or $C_3$, then the definition is to be amended accordingly, such as "$C_1$-$C_4$-Haloalkyl" will represent methyl, ethyl, propyl, isopropyl, butyl, isobutyl, sec-butyl and tert-butyl that have at least one hydrogen substituted with halogen, such as where the halogen is fluorine: $CF_3CF_2—$, $(CF_3)_2CH—$, $CH_3—CF_2—$, $CF_3CF_2—$, $CF_3$, $CF_2H—$, $CF_3CF_2CHCF_3$ or $CF_3CF_2CF_2CF_2—$.

The term "alkylene" is a straight or branched alkylene (divalent alkyl chain) having 1 to 8 carbon atoms, for example, methylene, ethylene, 1-methylethylene, 2-methylethylene, trimethylene, tetramethylene, pentamethylene, hexamethylene, heptamethylene, and octamethylene.

"$C_3$-$C_{15}$ Cycloalkyl", as used herein, denotes a carbocyclic group having 3- to 15-ring carbon atoms that is saturated or partially saturated, such as a $C_3$-$C_8$-cycloalkyl. Examples of $C_3$-$C_{15}$-carbocyclic groups include but are not limited to cyclopropyl, cyclobutyl, cyclopentyl, cyclohexyl, cycloheptyl or cyclooctyl or a bicyclic group, such as bicyclooctyl, bicyclononyl including indanyl and indenyl and bicyclodecyl. If a different number of carbon atoms is specified, such as $C_6$, then the definition is to be amended accordingly.

"aryl" or "$C_6$-$C_{15}$-Aromatic carbocyclic group", as used herein, denotes an aromatic group having 6- to 15-ring carbon atoms. Examples of $C_6$-$C_{15}$-aromatic carbocyclic groups include, but are not limited to, phenyl, phenylene, benzenetriyl, naphthyl, naphthylene, naphthalenetriyl or anthrylene. If a different number of carbon atoms is specified, such as $C_{10}$, then the definition is to be amended accordingly.

"4- to 8-Membered heterocyclyl", "5- to 6-membered heterocyclyl", "3- to 10-membered heterocyclyl", "3- to 14-membered heterocyclyl", "4- to 14-membered heterocyclyl" and "5- to 14-membered heterocyclyl", refers, respectively, to 4- to 8-membered, 5- to 6-membered, 3- to 10-membered, 3- to 14-membered, 4- to 14-membered and 5- to 14-membered heterocyclic rings containing at least one ring heteroatom selected from the group consisting of nitrogen, oxygen and sulphur, which may be saturated, partially saturated or unsaturated (aromatic). The heterocyclyl includes single ring groups, fused ring groups and bridged groups. Examples of such heterocyclyl include, but are not limited to, furan, pyrrole, pyrrolidine, pyrazole, imidazole, triazole, isotriazole, tetrazole, thiadiazole, isothiazole, oxadiazole, pyridine, piperidine, pyrazine, oxazole, isoxazole, pyrazine, pyridazine, pyrimidine, piperazine, pyrrolidine, pyrrolidinone, morpholine, triazine, oxazine, tetrahydrofuran, tetrahydrothiophene, tetrahydrothiopyran, tetrahydropyran, 1,4-dioxane, 1,4-oxathiane, indazole, quinoline, indazole, indole, 8-aza-bicyclo[3.2.1]octane, 2,3-dihydrobenzofuran or thiazole.

"Heteroaryl" is a subset of heterocyclyl, wherein the completely unsaturated (aromatic). Examples of such groups are pyridine and pyrazine.

The term "hydroxy" or "hydroxyl" includes groups with an —OH.

The term "heteroatom" includes atoms of any element other than carbon or hydrogen. Preferred heteroatoms are nitrogen, oxygen, sulfur and phosphorus. In one embodiment, "heteroatom" includes nitrogen, sulfur and oxygen.

The term "carboxy" refers to carboxylic acid.

The term "alkoxycarboxy" refers to an ester.

The term "carbamoyl" is —C(O)NH$_2$. The terms "monoalkylcarbamoyl" and "dialkylcarbamoyl" are carbamoyl, wherein the hydrogen or hydrogens on the nitrogen are substituted with $C_1$-$C_8$ alkyl as described above.

A second aspect of the invention provides a compound of Formula I, Ia, II or IIa or pharaceutical salts thereof as defined anywhere herein for use as a pharmaceutical.

Activating the IP receptor has been shown to have a beneficial effect or treat the following diseases or disorders:

PAH selected from: idiopathic PAH; familial PAH; PAH associated with a collagen vascular disease selected from: scleroderma, CREST syndrome, systemic lupus erythematosus (SLE), rheumatoid arthritis, Takayasu's arteritis, polymyositis, and dermatomyositis; PAH associated with a congenital heart disease selected from: atrial septic defect (ASD), ventricular septic defect (VSD) and patent ductus arteriosus in an individual; PAH associated with portal hypertension; PAH associated with HIV infection; PAH associated with ingestion of a drug or toxin; PAH associated with hereditary hemorrhagic telangiectasia; PAH associated with splenectomy; PAH associated with significant venous or capillary involvement; PAH associated with pulmonary veno-occlusive disease (PVOD); and PAH associated with pulmonary capillary hemangiomatosis (PCH); Raynaud's phenomenon, including Raynaud's disease and Raynaud's syndrome; fibrotic diseases, including pulmonary fibrosis, systemic sclerosis/scleroderma, hepatic fibrosis/cirrhosis, renal fibrosis; thrombotic diseases associated with excessive platelet aggregation, coronary artery disease, myocardial infarction, transient ischemic attack, angina, stroke, ischemia-reperfusion injury, restenosis, atrial fibrillation, blood clot formation, atherosclerosis, atherothrombosis, asthma, a symptom of asthma, a diabetic-related disorder, diabetic peripheral neuropathy, diabetic nephropathy, diabetic retinopathy, glaucoma or other disease of the eye with abnormal intraocular pressure, hypertension, preeclampsia, inflammation, prophylaxis against unwanted side effects of COX-1, COX-2 and non-selective COX inhibitors, psoriasis, psoriatic arthritis, rheumatoid arthritis, Crohn's disease, transplant rejection, multiple sclerosis, systemic lupus erythematosus (SLE), ulcerative colitis, ischemia-reperfusion injury, restenosis, atherosclerosis, acne, type 1 diabetes, type 2 diabetes, sepsis and chronic obstructive pulmonary disorder (COPD).

A further aspect of the invention provides a compound of Formula I, Ia, II or IIa or pharaceutical salts thereof for use in the treatment of PAH as described above.

A further aspect of the invention provides a compound of Formula I, Ia, II or IIa or pharaceutical salts thereof for use in the treatment of a disorder selected from the aforementioned diseases and disorders.

A still further aspect of the present invention provides for the use of a compound of formula I, Ia, II or IIa, as defined in any of the aforementioned embodiments, in free or pharmaceutically acceptable salt form, for the manufacture of a medicament for the treatment of pulmonary arterial hypertension.

An embodiment of the present invention provides for the use of a compound of formula I, Ia, II or IIa, as defined in any of the aforementioned embodiments, in free or pharmaceutically acceptable salt form, for the manufacture of a medicament for the treatment of PAH selected from: idiopathic PAH; familial PAH; PAH associated with a collagen vascular disease selected from: scleroderma, CREST syndrome, systemic lupus erythematosus (SLE), rheumatoid arthritis, Takayasu's arteritis, polymyositis, and dermatomyositis; PAH associated with a congenital heart disease selected from: atrial septic defect (ASD), ventricular septic defect (VSD) and patent ductus arteriosus in an individual; PAH associated with portal hypertension; PAH associated with HIV infection; PAH associated with ingestion of a drug or toxin; PAH associated with hereditary hemorrhagic telangiectasia; PAH associated with splenectomy; PAH associated with significant venous or capillary involvement;

PAH associated with pulmonary veno-occlusive disease (PVOD); and PAH associated with pulmonary capillary hemangiomatosis (PCH).

An embodiment of the present invention provides method for the prevention or treatment of an IP receptor mediated condition or disease comprising administering an effective amount of at least one compound as described herein to a subject in need of such treatment. Such IP receptor mediated condition or disease are selected from PAH selected from: idiopathic PAH; familial PAH; PAH associated with a collagen vascular disease selected from: scleroderma, CREST syndrome, systemic lupus erythematosus (SLE), rheumatoid arthritis, Takayasu's arteritis, polymyositis, and dermatomyositis; PAH associated with a congenital heart disease selected from: atrial septic defect (ASD), ventricular septic defect (VSD) and patent ductus arteriosus in an individual; PAH associated with portal hypertension; PAH associated with HIV infection; PAH associated with ingestion of a drug or toxin; PAH associated with hereditary hemorrhagic telangiectasia; PAH associated with splenectomy; PAH associated with significant venous or capillary involvement; PAH associated with pulmonary veno-occlusive disease (PVOD); and PAH associated with pulmonary capillary hemangiomatosis (PCH).

Other IP receptor mediated condition or disease are selected from platelet aggregation, coronary artery disease, myocardial infarction, transient ischemic attack, angina, stroke, ischemia-reperfusion injury, restenosis, atrial fibrillation, blood clot formation, atherosclerosis, atherothrombosis, asthma, a symptom of asthma, a diabetic-related disorder, diabetic peripheral neuropathy, diabetic nephropathy, diabetic retinopathy, glaucoma or other disease of the eye with abnormal intraocular pressure, hypertension, inflammation, psoriasis, psoriatic arthritis, rheumatoid arthritis, Crohn's disease, transplant rejection, multiple sclerosis, systemic lupus erythematosus (SLE), ulcerative colitis, ischemia-reperfusion injury, restenosis, atherosclerosis, acne, type 1 diabetes, type 2 diabetes, sepsis and chronic obstructive pulmonary disorder (COPD).

An embodiment of the present invention provides method for the prevention or treatment of an IP receptor mediated condition or disease comprising administering an effective amount of at least one compound as described herein to a subject in need of such treatment. Such IP receptor mediated condition or disease is PAH.

Throughout this specification and in the claims that follow, unless the context requires otherwise, the word "comprise", or variations such as "comprises" or "comprising", should be understood to imply the inclusion of a stated integer or step or group of integers or steps but not the exclusion of any other integer or step or group of integers or steps.

As used herein, the term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethanedisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate trifluoroacetate and xinafoate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, 1-hydroxy-2-naphtoic acid and sulfosalicylic acid.

Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, acetone or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Furthermore, the compounds of the present invention, including their salts, can also be obtained in the form of their hydrates, or include other solvents used for their crystallization.

Compounds of the invention, i.e. compounds of formula I, Ia, II or IIa that contain groups capable of acting as donors and/or acceptors for hydrogen bonds may be capable of forming co-crystals with suitable co-crystal formers. These co-crystals may be prepared from compounds of formula I, Ia, II or IIa by known co-crystal forming procedures. Such procedures include grinding, heating, co-subliming, co-melting, or contacting in solution compounds of formula I, Ia, II or IIa with the co-crystal former under crystallization conditions and isolating co-crystals thereby formed. Suitable co-crystal formers include those described in WO 2004/078163. Hence the invention further provides co-crystals comprising a compound of formula I, Ia, II or IIa.

As used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers or axes and may thus give rise to enantiomers, diastereomers, and other stereoisomeric forms that may be defined, in terms of absolute stereochemistry, as (R)- or (S)-. The present invention is meant to include all such possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Since the compounds of the invention are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions; these less pure preparations of the compounds should contain at least 1%, more suitably at least 5% and preferably from 10 to 59% of a compound of the invention.

Compounds of the present invention are either obtained in the free form, as a salt thereof, or as prodrug derivatives thereof.

When both a basic group and an acid group are present in the same molecule, the compounds of the present invention may also form internal salts, e.g., zwitterionic molecules.

The present invention also provides pro-drugs of the compounds of the present invention that converts in vivo to the compounds of the present invention. A pro-drug is an active or inactive compound that is modified chemically through in vivo physiological action, such as hydrolysis, metabolism and the like, into a compound of this invention following administration of the prodrug to a subject. The suitability and techniques involved in making and using pro-drugs are well known by those skilled in the art. Prodrugs can be conceptually divided into two non-exclusive categories, bioprecursor prodrugs and carrier prodrugs. See *The Practice of Medicinal Chemistry*, Ch. 31-32 (Ed. Wermuth, Academic Press, San Diego, Calif., 2001). Generally, bioprecursor prodrugs are compounds, which are inactive or have low activity compared to the corresponding active drug compound that contain one or more protective groups and are converted to an active form by metabolism or solvolysis. Both the active drug form and any released metabolic products should have acceptably low toxicity.

Carrier prodrugs are drug compounds that contain a transport moiety, e.g., that improve uptake and/or localized delivery to a site(s) of action. Desirably for such a carrier prodrug, the linkage between the drug moiety and the transport moiety is a covalent bond, the prodrug is inactive or less active than the drug compound, and any released transport moiety is acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g., stability, water solubility, suppression of an undesirable organoleptic or physiochemical property). For example, lipophilicity can be increased by esterification of (a) hydroxyl groups with lipophilic carboxylic acids (e.g., a carboxylic acid having at least one lipophilic moiety), or (b) carboxylic acid groups with lipophilic alcohols (e.g., an alcohol having at least one lipophilic moiety, for example aliphatic alcohols).

Exemplary prodrugs are, e.g., esters of free carboxylic acids and S-acyl derivatives of thiols and O-acyl derivatives of alcohols or phenols, wherein acyl has a meaning as defined herein. Suitable prodrugs are often pharmaceutically acceptable ester derivatives convertible by solvolysis under physiological conditions to the parent carboxylic acid, e.g., lower alkyl esters, cycloalkyl esters, lower alkenyl esters, benzyl esters, mono- or di-substituted lower alkyl esters, such as the ω-(amino, mono- or di-lower alkylamino, carboxy, lower alkoxycarbonyl)-lower alkyl esters, the α-(lower alkanoyloxy, lower alkoxycarbonyl or di-lower alkylaminocarbonyl)-lower alkyl esters, such as the pivaloyloxymethyl ester and the like conventionally used in the art. In addition, amines have been masked as arylcarbonyloxymethyl substituted derivatives which are cleaved by esterases in vivo releasing the free drug and formaldehyde (Bundgaard, *J. Med. Chem.* 2503 (1989)). Moreover, drugs containing an acidic NH group, such as imidazole, imide, indole and the like, have been masked with N-acyloxymethyl groups (Bundgaard, *Design of Prodrugs*, Elsevier (1985)). Hydroxy groups have been masked as esters and ethers. EP 039,051 (Sloan and Little) discloses Mannich-base hydroxamic acid prodrugs, their preparation and use.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2$H, $^3$H, $^{11}$C, $^{13}$C, $^{14}$C, $^{15}$N, $^{18}$F $^{31}$P, $^{32}$P, $^{35}$S, $^{36}$Cl, $^{125}$I respectively. The invention includes various isotopically labeled compounds as defined herein, for example those into which radioactive isotopes, such as $^3$H, $^{13}$C, and $^{14}$C, are present. Such isotopically labeled compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, an $^{18}$F or labeled compound may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

Further, substitution with heavier isotopes, particularly deuterium (i.e., $^2$H or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula I, Ia, II or IIa. The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Isotopically-labeled compounds of formula I, Ia, II or IIa can generally be prepared by conventional techniques known to those skilled in the art or by processes analogous to those described in the accompanying Examples and Preparations using an appropriate isotopically-labeled reagents in place of the non-labeled reagent previously employed.

Pharmaceutically acceptable solvates in accordance with the invention include those wherein the solvent of crystallization may be isotopically substituted, e.g. D$_2$O, d$_6$-acetone, d$_6$-DMSO.

Synthesis

The Intermediate

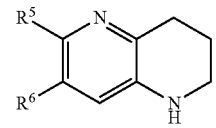

may be prepared according to *Tetrahedron Letters*, Vol. 38, No. 43, pp. 7499-7502, or in the Example section.

Furthermore, the compounds of the invention may be prepared according to the following Schemes:

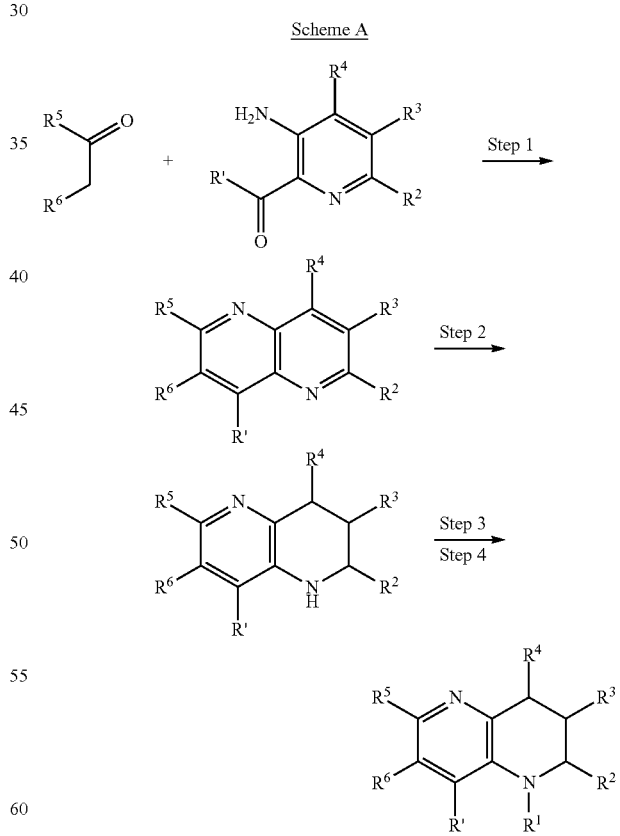

Scheme A begins with a Step 1 reaction taking commercially available starting material or starting material that one skilled in the art can synthesize and condensing the material as shown. Step 2 is a hydrogenation. Step 3 is either an alkylation or reductive amination depending on the desired product. Step 4 of Scheme A is a hydrolysis to form a free acid, if an ester is present. $R^1$, $R^2$, $R^3$, $R^4$, $R^5$ and $R^6$ are as defined herein.

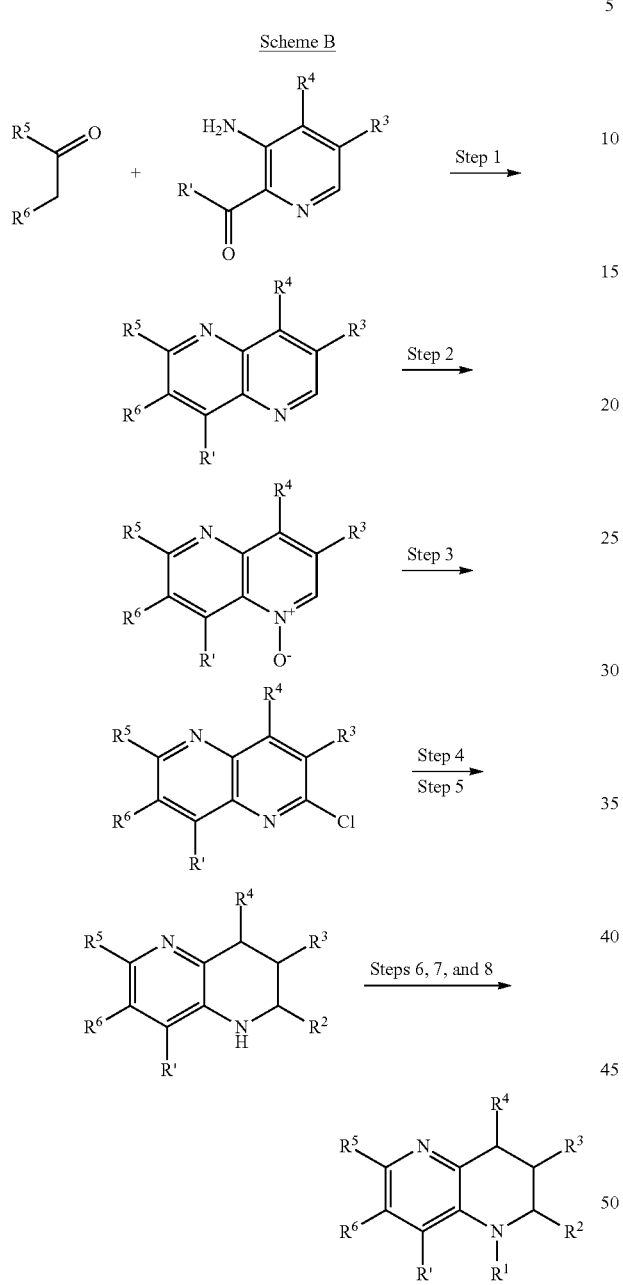

Scheme B

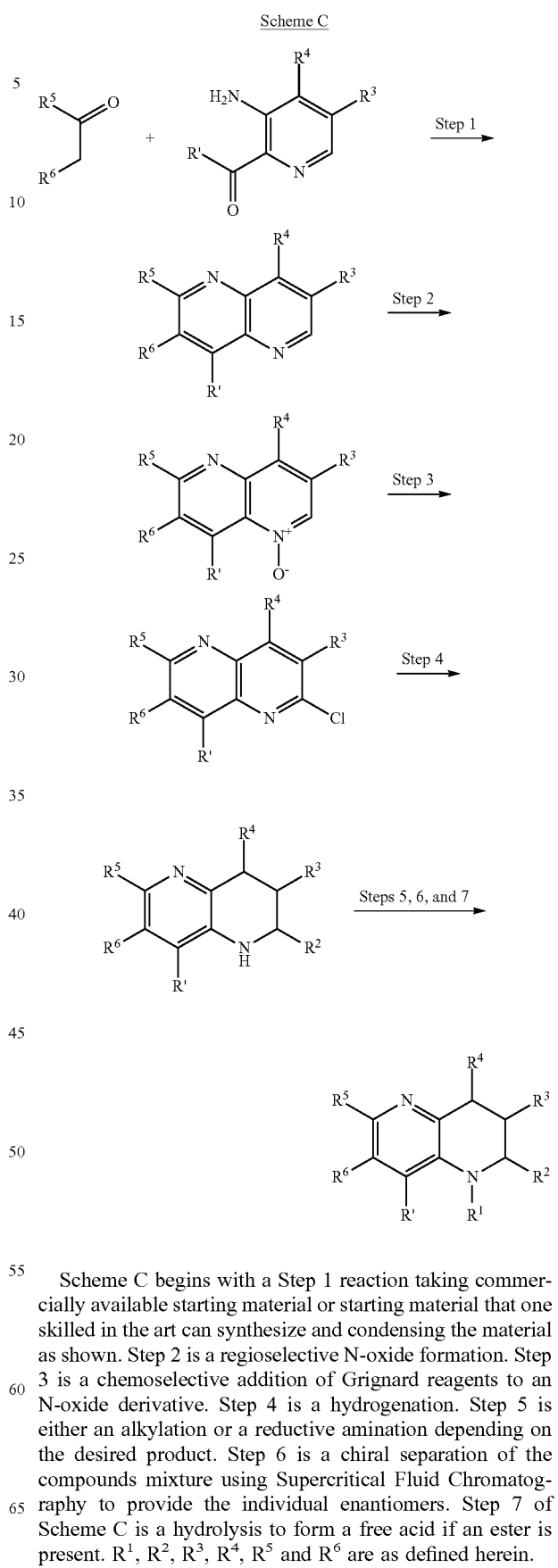

Scheme C

Scheme B begins with a Step 1 reaction taking commercially available starting material or starting material that one skilled in the art can synthesize and condensing the material as shown. Step 2 is a regioselective N-oxide formation. Step 3 selectively inserts a chlorine. Step 4 is a Negishi cross-coupling at the chlorine on the ring. Step 5 is a hydrogenation. Step 6 is either an alkylation or a reductive amination depending on the desired product. Step 7 is a chiral separation of the compounds mixture using Supercritical Fluid Chromatography to provide the individual enantiomers. Step 8 of Scheme B is a hydrolysis to form a free acid if an ester is present. $R^1$, $R^2$, $R^3$, $R^4$, $R^5$ and $R^6$ are as defined herein.

Scheme C begins with a Step 1 reaction taking commercially available starting material or starting material that one skilled in the art can synthesize and condensing the material as shown. Step 2 is a regioselective N-oxide formation. Step 3 is a chemoselective addition of Grignard reagents to an N-oxide derivative. Step 4 is a hydrogenation. Step 5 is either an alkylation or a reductive amination depending on the desired product. Step 6 is a chiral separation of the compounds mixture using Supercritical Fluid Chromatography to provide the individual enantiomers. Step 7 of Scheme C is a hydrolysis to form a free acid if an ester is present. $R^1$, $R^2$, $R^3$, $R^4$, $R^5$ and $R^6$ are as defined herein.

Scheme D

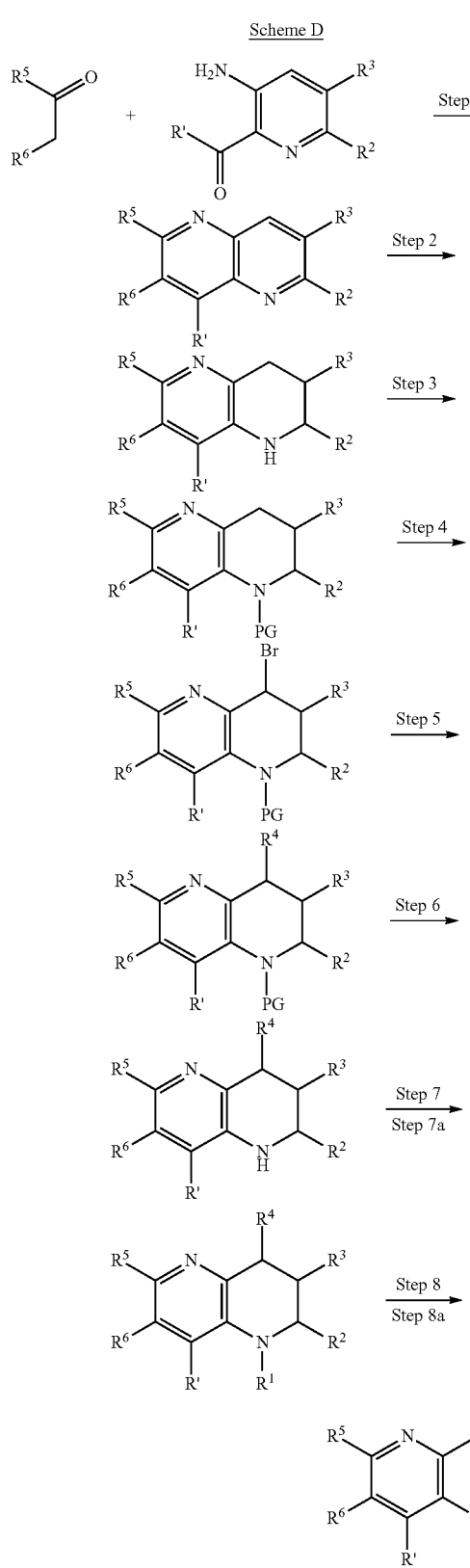

Scheme D begins with a Step 1 reaction taking commercially available starting material or starting material that one skilled in the art can synthesize and condensing the material as shown. Step 2 is a hydrogenation. Step 3 is the introduction of a protecting group (PG). Step 4 is a bromination. Step 5 is either an organometallic reaction or a nucleophilic substitution of a halide derivative depending on the desired product. Step 6 is an optional removal of a protecting group. Step 7 is either an alkylation or reductive amination depending on the desired product. Step 8 of Scheme D is an optional deprotection step and a hydrolysis to form a free acid, if an ester is present. Chiral separation can be done as Step 7a or Step 8a. $R^1$, $R^2$, $R^3$, $R^4$, $R^5$ and $R^6$ are as defined herein.

Scheme E

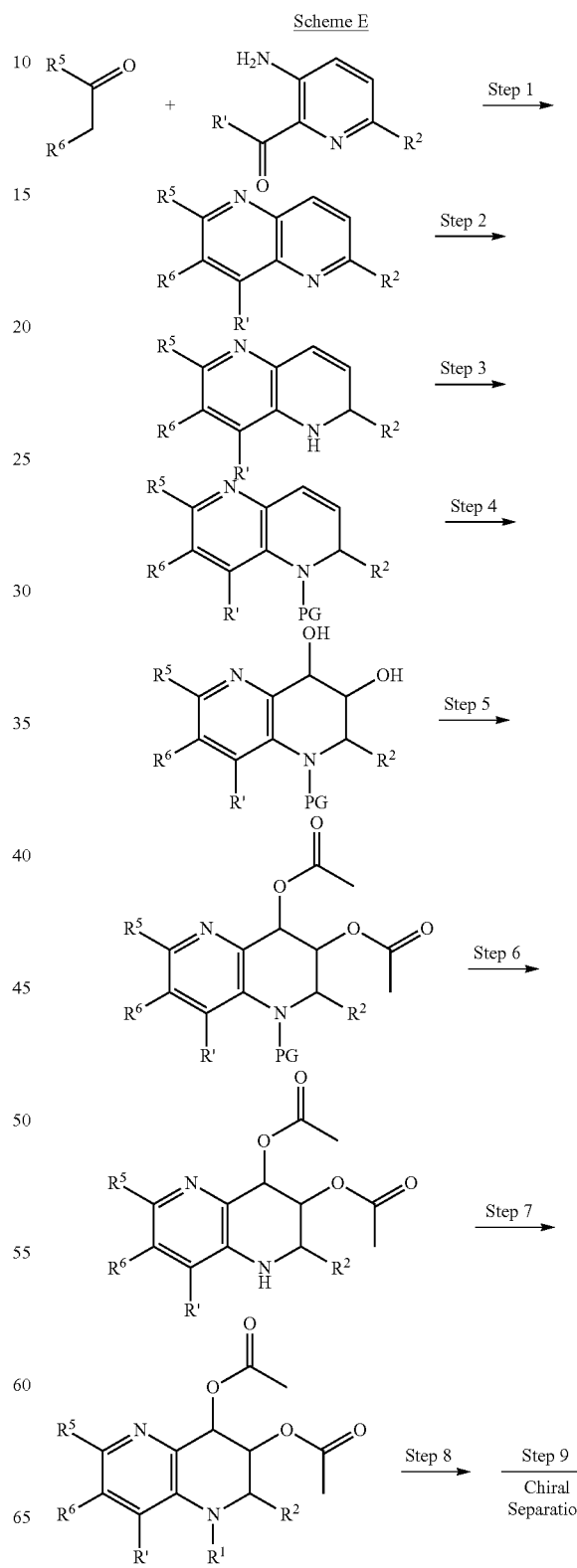

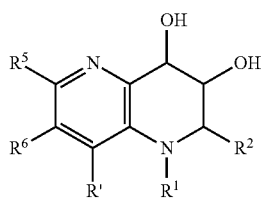

Scheme E begins with a Step 1 reaction taking commercially available starting material or starting material that one skilled in the art can synthesize and condensing the material as shown. Step 2 is a reduction. Step 3 is the introduction of a protecting group (PG). Step 4 is a hydroxylation of alkene. Step 5 is the introduction of hydroxyl protecting group. Step 6 is a selective removal of a protecting group. Step 7 is either an alkylation or reductive amination depending on the desired product. Step 8 is a deprotection step and a hydrolysis to form a free acid, if an ester is present. Step 9 of Scheme E is a chiral separation of the compounds mixture using Supercritical Fluid Chromatography to provide the individual enantiomers. $R^1$, $R^2$, $R^5$ and $R^6$ are as defined herein.

Scheme F

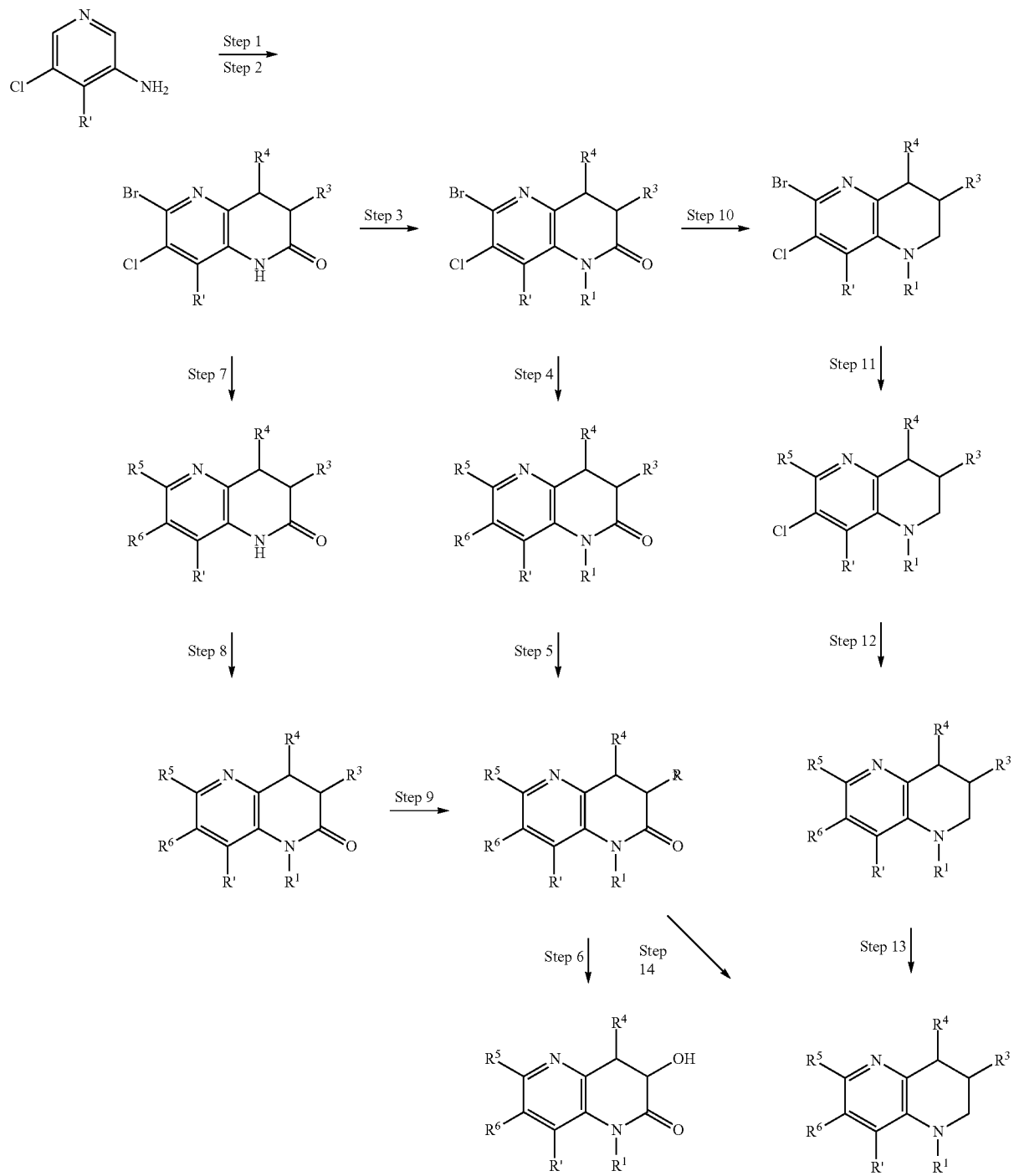

Scheme F begins with a Step 1 reaction taking commercially available starting material or starting material that one skilled in the art can synthesize and dibrominating the material. Step 2 is a Negishi cross-coupling reaction concomitant with an intramolecular cyclisation. Steps 3 and 8 are alkylations. Steps 4, 7, 11 and 12 are Suzuki cross-coupling reactions. Steps 5, 9 and 13 are a hydrolysis to form a free acid. Steps 10 and 14 are a reduction. Step 6 of Scheme F is a hydroxylation. $R^1$, $R^3$, $R^4$, $R^5$ and $R^6$ are as defined herein.

Scheme G

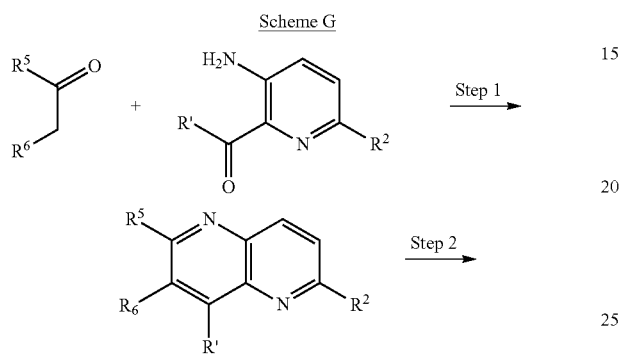

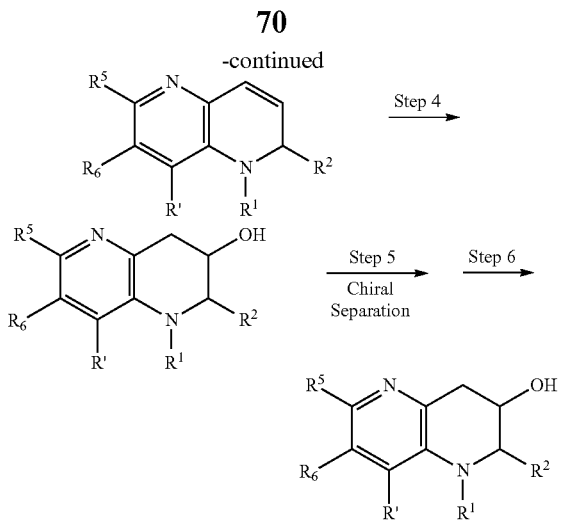

Scheme G begins with a Step 1 reaction taking commercially available starting material or starting material that one skilled in the art can synthesize and condensing the material as shown. Step 2 is a reduction. Step 3 is either an alkylation or reductive amination depending on the desired product. Step 4 is an hydroboration of alkene. Step 5 is a chiral separation of the compounds mixture using Supercritical Fluid Chromatography to provide the individual enantiomers. Step 6 of Scheme G is a hydrolysis to form a free acid if an ester is present. $R^1$, $R^2$, $R^5$ and $R^6$ are as defined herein.

Scheme H

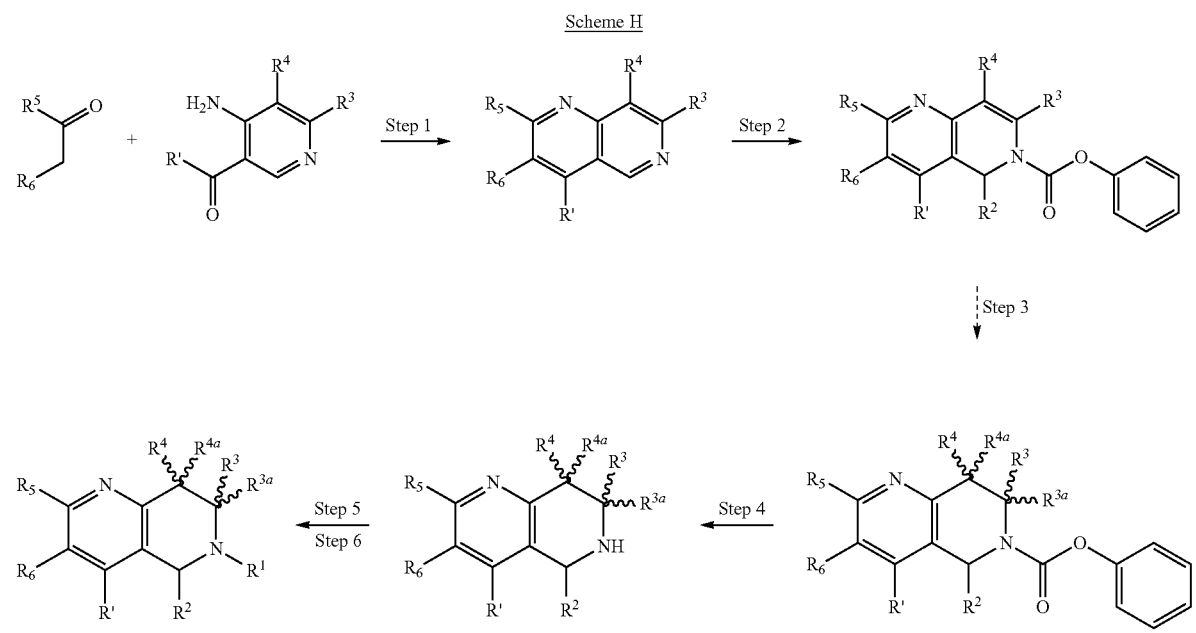

-continued

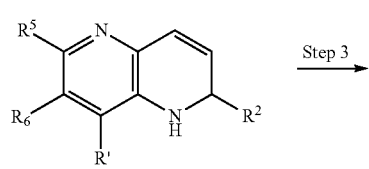

Scheme H begins with a Step 1 by reacting starting materials (commercially available or preparation known to a person skilled in the art) and condensing said materials as shown. Step 2 is an organometallic addition e.g. by using a suitable reagent such methylmagnesium bromide, and in-situ protection. Step 3 is a hydrogenation. Step 4 is a deprotection. Step 5 is either an alkylation or reductive amination depending on the desired product. Step 6 is an ester hydrolysis if required. $R^1$, $R^2$, $R^3$, $R^{3a}$, $R^4$, $R^{4a}$, $R^5$, and $R^6$ are as defined in embodiment 1 of the consistory clauses.

Scheme I:

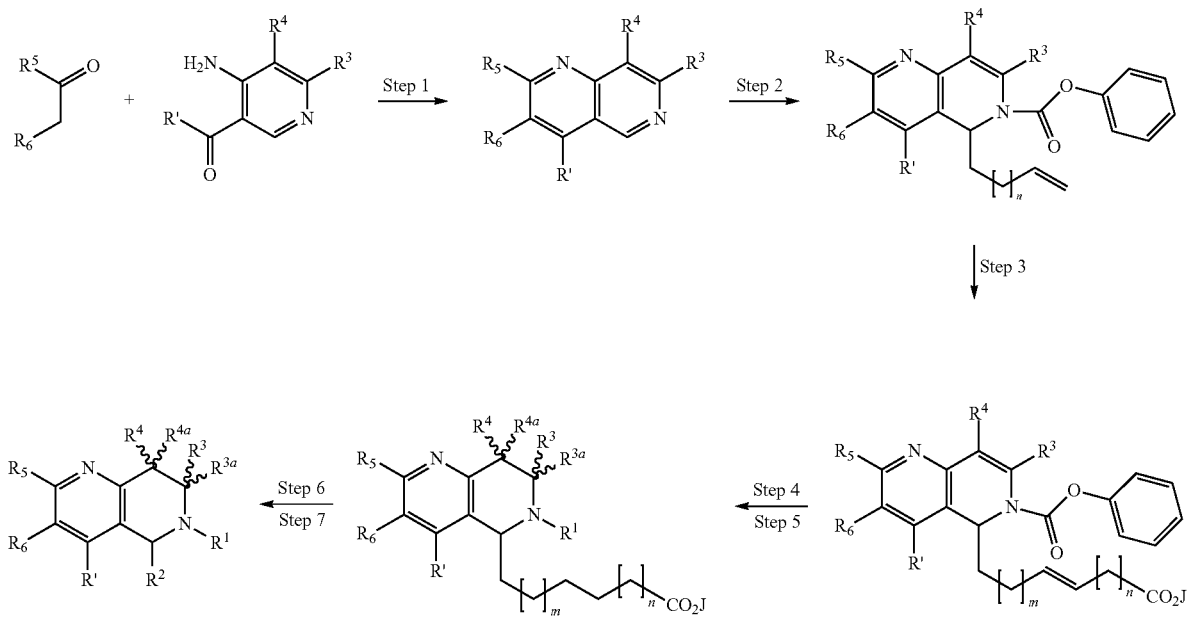

Scheme I begins with a Step 1 by reacting starting materials (commercially available or preparation known to a person skilled in the art) and condensing the material as shown. Step 2 is an organometallic addition and in-situ protection. Step 3 is an olefin metathesis reaction. Step 4 is a hydrogenation. Step 5 is a deprotection. Step 6, if required, is either an alkylation or reductive amination depending on the desired product. Step 7 is an ester hydrolysis if required. $R^1$, $R^2$, $R^3$, $R^{3a}$, $R^4$, $R^{4a}$, $R^5$ and $R^6$ are as defined in embodiment 1 of the consistory clauses. J is H or $C_1$-$C_4$ alkyl and m and n are as defined in embodiment 5 of the consistory clauses.

Scheme J

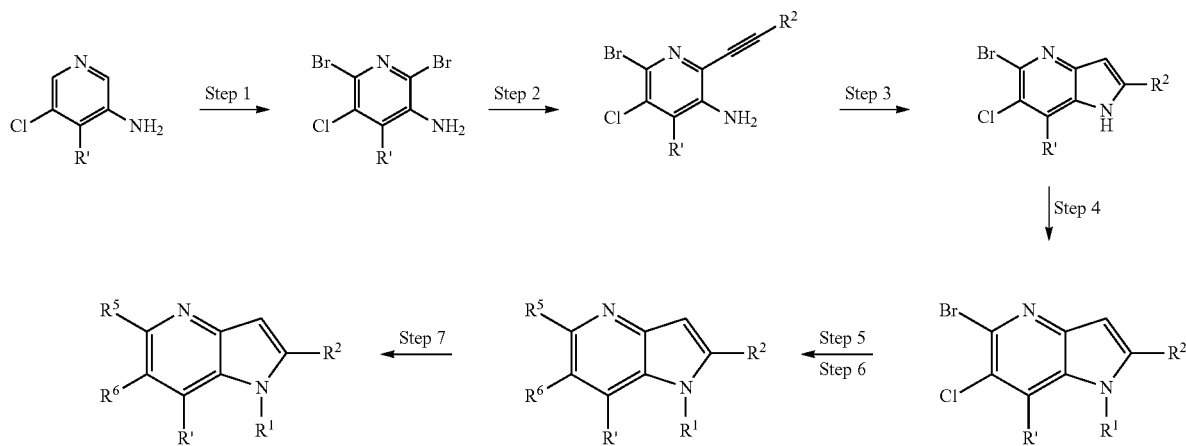

Scheme J begins with a Step 1 bromination. Step 2 is a Sonogashira coupling. Step 3 is a cyclisation. Step 4 is an alkylation. Steps 5 and 6 are subsequent Suzuki reactions. Step 7 is an ester hydrolysis if required. $R^1$, $R^2$, $R^5$ and $R^6$ are as defined in embodiment 1 of the consistory clauses.

Scheme K

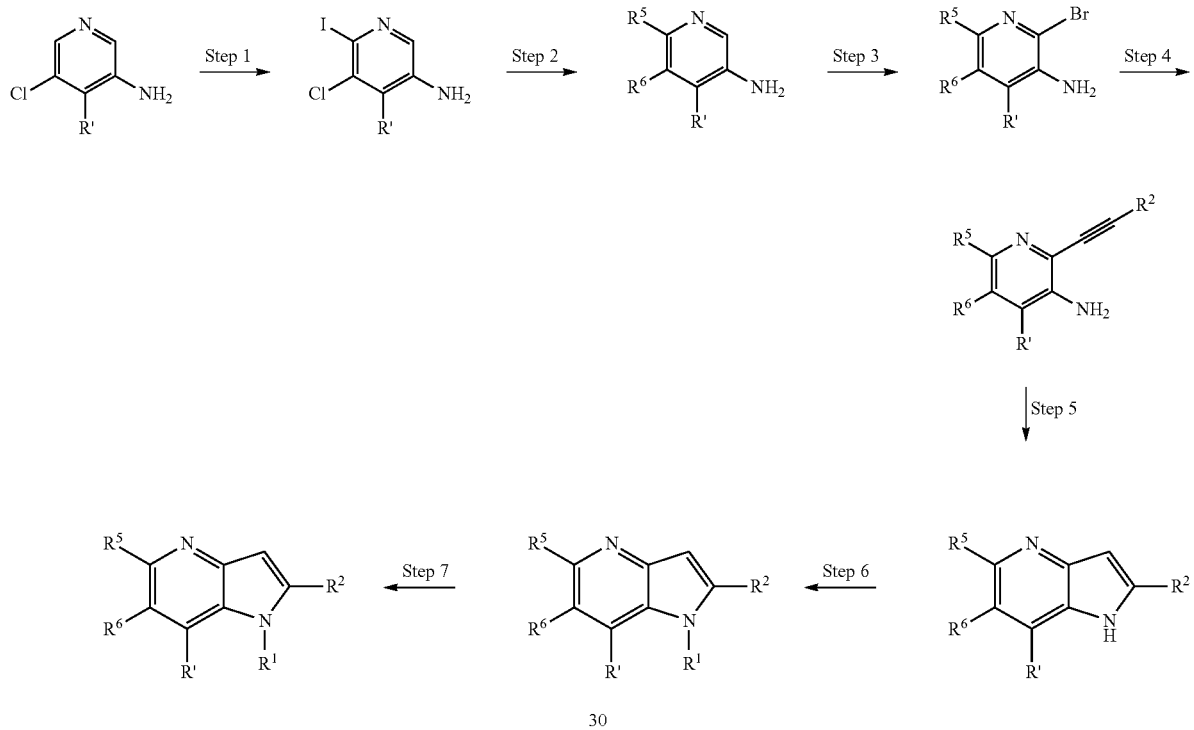

Scheme 2 begins with a Step 1 iodination. Step 2 is a Suzuki coupling. Step 3 is a bromination. Step 4 is a Sonogashira coupling. Step 5 is a cyclisation. Step 6 is an alkylation. Step 7 is an ester hydrolysis if required. $R^1$, $R^2$, $R^5$ and $R^6$ are as defined in embodiment 1 of the consistory clauses.

Scheme L

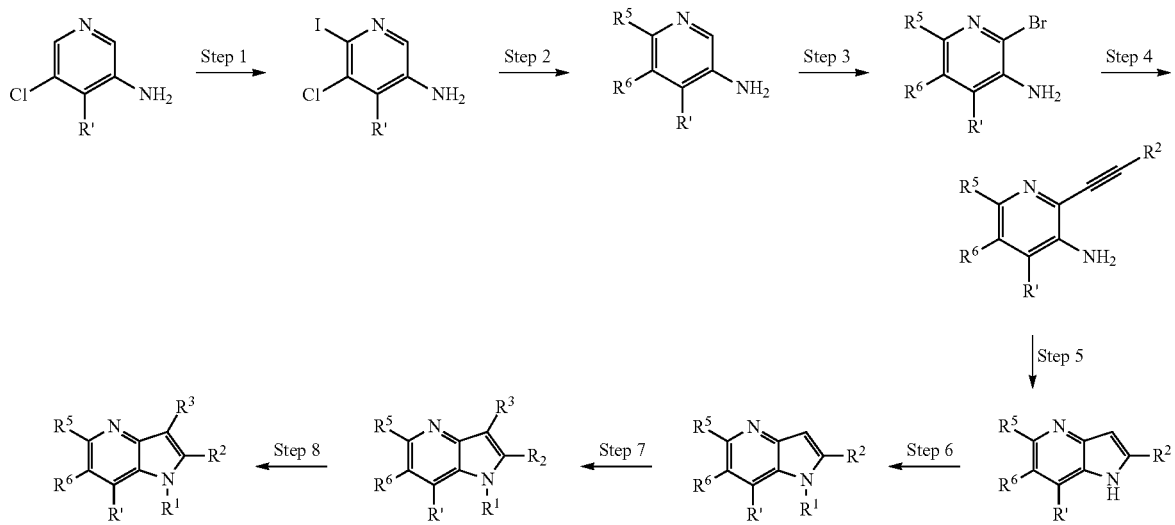

Scheme 3 begins with a Step 1 iodination. Step 2 is a Suzuki coupling. Step 3 is a bromination. Step 4 is a Sonogashira coupling. Step 5 is a cyclisation. Step 6 is an alkylation. Step 7 is either a Vilsmeyer formylation followed by reductive amination; or oxidation and then coupling; or reduction followed by an alkylation if required; or bromination followed by an alkylation, or suzuki coupling or Grignard, Step 8 is an ester hydrolysis if required. $R^1$, $R^2$, $R^3$, $R^5$ and $R^6$ are as defined in embodiment 1 of the consistory clauses.

Scheme M

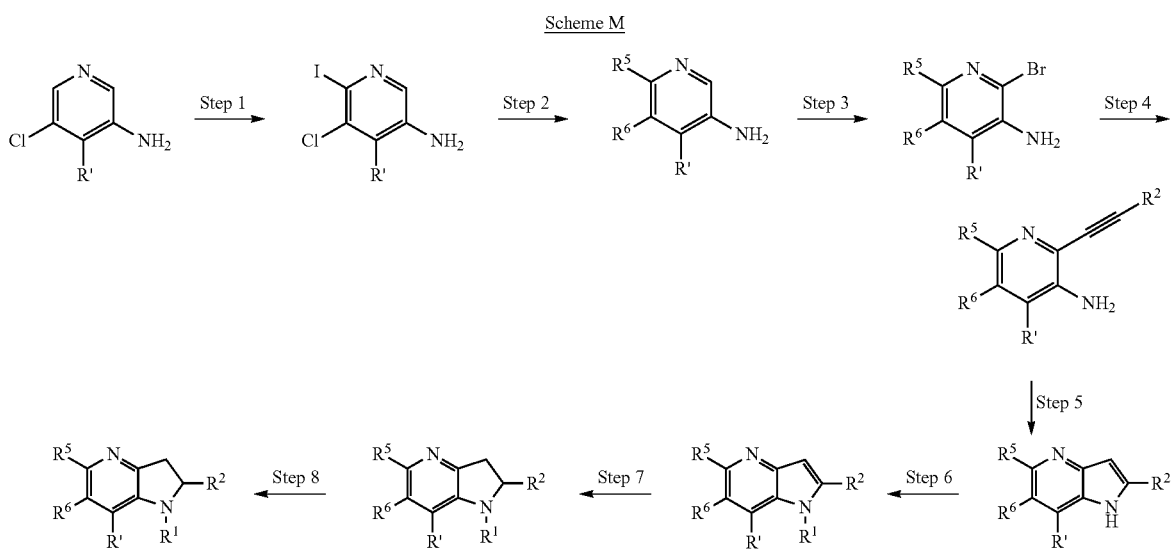

Scheme M begins with a Step 1 iodination. Step 2 is a Suzuki coupling. Step 3 is a bromination. Step 4 is a Sonogashira coupling. Step 5 is a cyclisation. Step 6 is an alkylation. Step 7 is a hydrogenation, Step 8 is an ester hydrolysis if required.

The skilled person will appreciate that the general synthetic routes detailed above show common reactions to transform the starting materials as required. The specific reaction conditions are not provided, but these are well known to those skilled in the art and appropriate conditions considered to be within the skilled person's common general knowledge.

The starting materials are either commercially available compounds or are known compounds and can be prepared from procedures described in the organic chemistry art.

Compounds of formula I, Ia, II or IIa, in free form, may be converted into salt form, and vice versa, in a conventional manner understood by those skilled in the art. The compounds in free or salt form can be obtained in the form of hydrates or solvates containing a solvent used for crystallisation. Compounds of formula I, Ia, II or IIa can be recovered from reaction mixtures and purified in a conventional manner. Isomers, such as stereoisomers, may be obtained in a conventional manner, e.g., by fractional crystallisation or asymmetric synthesis from correspondingly asymmetrically substituted, e.g., optically active, starting materials.

The compounds of Formula I, Ia, II or IIa or pharaceutical salts thereof can be prepared, e.g., using the reactions and techniques described below and in the Examples. The reactions may be performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

The various substituents on the synthetic intermediates and final products shown in the following reaction schemes can be present in their fully elaborated forms, with suitable protecting groups where required as understood by one skilled in the art, or in precursor forms which can later be elaborated into their final forms by methods familiar to one skilled in the art. The substituents can also be added at various stages throughout the synthetic sequence or after completion of the synthetic sequence. In many cases, commonly used functional group manipulations can be used to transform one intermediate into another intermediate, or one compound of formula I, Ia, II or IIa into another compound of formula I, Ia, II or IIa. Examples of such manipulations are conversion of an ester or a ketone to an alcohol; conversion of an ester to a ketone; interconversions of esters, acids and amides; alkylation, acylation and sulfonylation of alcohols and amines; and many others. Substituents can also be added using common reactions, such as alkylation, acylation, halogenation or oxidation. Such manipulations are well-known in the art, and many reference works summarize procedures and methods for such manipulations. Some reference works which gives examples and references to the primary literature of organic synthesis for many functional group manipulations, as well as other transformations commonly used in the art of organic synthesis are *March's Organic Chemistry*, 5$^{th}$ Edition, Wiley and Chichester, Eds. (2001); *Comprehensive Organic Transformations*, Larock, Ed., VCH (1989); *Comprehensive Organic Functional Group Transformations*, Katritzky et al. (series editors), Pergamon (1995); and *Comprehensive Organic Synthesis*, Trost and Fleming (series editors), Pergamon (1991). It will also be recognized that another major consideration in the planning of any synthetic route in this field is the judicious choice of the protecting group used for protection of the reactive functional groups present in the compounds described in this invention. Multiple protecting groups within the same molecule can be chosen such that each of these protecting groups can either be removed without removal of other protecting groups in the same molecule, or several protecting groups can be removed using the same reaction step, depending upon the outcome desired. An authoritative account describing many alternatives to the trained practitioner is Greene and Wuts, *Protective Groups in Organic Synthesis*, Wiley and Sons, 4$^{th}$ Edition (2006).

Pharmacological Activity

The compounds disclosed herein activate the IP receptor and are useful in the treatment of several diseases and disorders, and in the amelioration of symptoms thereof.

Without limitation, these include the following:

Pulmonary Arterial Hypertension (PAH)

PAH has a multifactorial pathobiology. Vasoconstriction, remodeling of the pulmonary vessel wall, and thrombosis contribute to increased pulmonary vascular resistance in PAH (Humbert et al, J. Am. Coll. Cardiol., 2004, 43:13S-24S.). The compounds of the present invention disclosed herein are useful in the treatment of pulmonary arterial hypertension (PAH) and symptoms thereof. PAH shall be understood to encompass the following forms of pulmonary arterial hypertension described in the 2003 World Health Organization (WHO) clinical classification of pulmonary arterial hypertension: idiopathic PAH (BPAH); familial PAH (FPAH); PAH associated with other conditions (APAH), such as PAH associated with collagen vascular disease, PAH associated with congenital systemic-to-pulmonary shunts, PAH associated with portal hypertension, PAH associated with HTV infection, PAH associated with drugs or toxins, or PAH associated with Other; and PAH associated with significant venous or capillary involvement. Idiopathic PAH refers to PAH of undetermined cause. Familial PAH refers to PAH for which hereditary transmission is suspected or documented. PAH associated with collagen vascular disease shall be understood to encompass PAH associated with scleroderma, PAH associated with CREST (calcinosis cutis, Raynaud's phenomenon, esophageal dysfunction, sclerodactyly, and telangiectasias) syndrome, PAH associated with systemic lupus erythematosus (SLE), PAH associated with rheumatoid arthritis, PAH associated with Takayasu's arteritis, PAH associated with polymyositis, and PAH associated with dermatomyositis. PAH associated with congenital systerruc-to-pulmonary shunts shall be understood to encompass PAH associated with atrial septic defect (ASD), PAH associated with ventricular septic defect (VSD) and PAH associated with patent ductus arteriosus.

PAH associated with drugs or toxins shall be understood to encompass PAH associated with ingestion of aminorex, PAH associated with ingestion of a fenfluramine compound (e.g., PAH associated with ingestion of fenfluramine or PAH associated with ingestion of dexfenfluramine), PAH associated with ingestion of certain toxic oils (e g, PAH associated with ingestion of rapeseed oil), PAH associated with ingestion of pyrrolizidine alkaloids (e.g, PAH associated with ingestion of bush tea) and PAH associated with ingestion of monocrotaline. PAH associated with Other shall be understood to encompass PAH associated with a thyroid disorder, PAH associated with glycogen storage disease, PAH associated with Gaucher disease, PAH associated with hereditary hemorrhagic telangiectasia, PAH associated with a hemoglobinopathy, PAH associated with a myeloproliferative disorder, and PAH associated with splenectomy. PAH associated with significant venous or capillary involvement shall be understood to encompass PAH associated with pulmonary veno-occlusive disease (PVOD) and PAH associated with pulmonary capillary hemangiomatosis (PCH). (See, e.g, Simonneau et al, J. Am. Coll. Cardiol., 2004, 43:5S-12S; McGoon et al., Chest, 2004, 126:14S-34S; Rabinovitch, Annu. Rev. Pathol. Mech. Dis., 2007, 2:369-399; McLaughlin et al, Circulation, 2006, 114:1417-1431; Strauss et al, Clin. Chest. Med., 2007, 28:127-142; Taichman et al., Clin. Chest. Med., 2007, 28:1-22.).

Evidence for the association of PAH with scleroderma and the beneficial effect of an agonist of the IP receptor on PAH is given by Badesch et al (Badesch et al, Ann. Intern. Med., 2000, 132:425-434). Evidence for the association of PAH with the collagen vascular diseases mixed connective tissue disease (MCTD), systemic lupus erythematosus (SLE), Sjogren's syndrome and CREST syndrome and the beneficial effect of an agonist of the IP receptor on PAH is given by Humbert et al. (Eur. Respir. J., 1999, 13:1351-1356). Evidence for the association of PAH with CREST syndrome and the beneficial effect of an agonist of the IP receptor on PAH is given by Miwa et al. (Int. Heart J., 2007, 48:417-422). Evidence for the association of PAH with SLE and the beneficial effect of an agonist of the IP receptor on PAH is given by Robbins et al (Chest, 2000, 117:14-18). Evidence for the association of PAH with HIV infection and the beneficial of an agonist of the IP receptor on PAH is given by Aguilar et al. (Am. J. Respir. Crit. Care Med., 2000, 162:1846-1850). Evidence for the association of PAH with congenital heart defects (including ASD, VSD and patent ductus arteriosus) and the beneficial effect of an agonist of the IP receptor on PAH is given by Rosenzweig et al. (Circulation, 1999, 99:1858-1865).

Evidence for the association of PAH with fenfluramine and with dexfenfluramine, anorexigens, is given by Archer et al. (Am. J. Respir. Crit. Care Med., 1998, 158: 1061-1067). Evidence for the association of PAH with hereditary hemorrhagic telangiectasia is given by McGoon et al. (Chest, 2004, 126:14-34). Evidence for the association of PAH with splenectomy is given by Hoeper et al. (Ann. Intern. Med., 1999, 130:506-509). Evidence for the association of PAH with portal hypertension and the beneficial effect of an agonist of the IP receptor on PAH is given by Hoeper et al. (Eur. Respir. J., 2005, 25:502-508).

Symptoms of PAH include dyspnea, angina, syncope and edema (McLaughlin et al., Circulation, 2006, 114:1417-1431). The compounds of the present invention disclosed herein are useful in the treatment of symptoms of PAH.

Antiplatelet Therapies (Conditions Related to Platelet Aggregation)

Antiplatelet agents (antiplatelets) are prescribed for a variety of conditions. For example, in coronary artery disease they are used to help prevent myocardial infarction or stroke in patients who are at risk of developing obstructive blood clots (e.g., coronary thrombosis).

In a myocardial infarction, the heart muscle does not receive enough oxygen-rich blood as a result of a blockage in the coronary blood vessels. If taken while an attack is in progress or immediately afterward (preferably within 30 min), antiplatelets can reduce the damage to the heart.

A transient ischemic attack ("TIA" or "mini-stroke") is a brief interruption of oxygen flow to the brain due to decreased blood flow through arteries, usually due to an obstructing blood clot. Antiplatelet drugs have been found to be effective in preventing TIAs. Angina is a temporary and often recurring chest pain, pressure or discomfort caused by inadequate oxygen-rich blood flow (ischemia) to some parts of the heart. In patients with angina, antiplatelet therapy can reduce the effects of angina and the risk of myocardial infarction.

Stroke is an event in which the brain does not receive enough oxygen-rich blood, usually due to blockage of a cerebral blood vessel by a blood clot. In high-risk patients, taking antiplatelets regularly has been found to prevent the formation of blood clots that cause first or second strokes. Angioplasty is a catheter based technique used to open arteries obstructed by a blood clot. Whether or not stenting is performed immediately after this procedure to keep the artery open, antiplatelets can reduce the risk of forming additional blood clots following the procedure(s).

Coronary bypass surgery is a surgical procedure in which an artery or vein is taken from elsewhere in the body and grafted to a blocked coronary artery, rerouting blood around the blockage and through the newly attached vessel. After the procedure, antiplatelets can reduce the risk of secondary blood clots.

Atrial fibrillation is the most common type of sustained irregular heart rhythm (arrhythmia). Atrial fibrillation affects about two million Americans every year. In atrial fibrillation, the atria (the heart's upper chambers) rapidly fire electrical signals that cause them to quiver rather than contract normally. The result is an abnormally fast and highly irregular heartbeat. When given after an episode of atrial fibrillation, antiplatelets can reduce the risk of blood clots forming in the heart and traveling to the brain (embolism).

There is evidence that an IP receptor agonist will inhibit platelet aggregation and thus be a potential treatment as an antiplatelet therapy (see, e.g., Moncada et al., Lancet, 1977, 1: 18-20). It has been shown that genetic deficiency of the IP receptor in mice leads to an increased propensity towards thrombosis (Murata et al, Nature, 1997, 388:678-682).

IP receptor agonists can be used to treat, for example, claudication or peripheral artery disease as well as cardiovascular complications, arterial thrombosis, atherosclerosis, vasoconstriction caused by serotonin, ischemia-reperfusion injury, and restenosis of arteries following angioplasty or stent placement. (See, e.g., Fetalvero et al, Prostaglandins Other Lipid Mediat., 2007, 82:109-118; Arehart et al, Curr. Med. Chem., 2007, 14:2161-2169; Davi et al, N. Engl. J. Med., 2007, 357:2482-2494; Fetalvero et al, Am. J. Physiol. Heart. Circ. Physiol., 2006, 290:H1337-H1346; Murata et al, Nature, 1997, 388:678-682; Wang et al, Proc. Natl. Acad. Sci. USA, 2006, 103:14507-14512; Xiao et al, Circulation, 2001, 104:2210-2215; McCormick et al, Biochem. Soc. Trans., 2007, 35:910-911; Arehart et al, Circ. Res., 2008, Mar. 6.).

IP receptor agonists can also be used alone or in combination with thrombolytic therapy, for example, tissue-type plasminogen activator (t-PA), to provide cardioprotection following MI or postischemic myocardial dysfunction or protection from ischemic injury during percutaneous coronary intervention, and the like, including complications resulting therefrom. IP receptor agonists can also be used in antiplatelet therapies in combination with, for example, alpha-tocopherol (vitamin E), echistatin (a disintegrin) or, in states of hypercoagulability, heparin. (See, e.g., Chan., J. Nutr., 1998, 128:1593-1596; Mardla et al, Platelets, 2004, 15:319-324; Bernabei et al, Ann. Thorac. Surg., 1995, 59:149-153; Gainza et al, J. Nephrol., 2006, 19:648-655.)

The IP receptor agonists disclosed herein provide beneficial improvement in microcirculation to patients in need of antiplatelet therapy by antagonizing the vasoconstrictive products of the aggregating platelets in, for example and not limited to the indications described above.

Accordingly, in some embodiments, the present invention provides methods for reducing platelet aggregation in a patient in need thereof, comprising administering to the patient a composition comprising an IP receptor agonist disclosed herein. In further embodiments, the present invention provides methods for treating coronary artery disease, myocardial infarction, transient ischemic attack, angina, stroke, atrial fibrillation, or a symptom of any of the foregoing in a patient in need of the treatment, comprising administering to the patient a composition comprising an IP receptor agonist disclosed herein.

In further embodiments, the present invention provides methods for reducing risk of blood clot formation in an angioplasty or coronary bypass surgery patient, or a patient suffering from atrial fibrillation, comprising administering to the patient a composition comprising an IP receptor agonist disclosed herein at a time where such risk exists.

Atherosclerosis

Atherosclerosis is a complex disease characterized by inflammation, lipid accumulation, cell death and fibrosis. It is the leading cause of mortality in many countries, including the United States. Atherosclerosis, as the term is used herein, shall be understood to encompass disorders of large and medium-sized arteries that result in the progressive accumulation within the intima of smooth muscle cells and lipids.

It has been shown that an agonist of the IP receptor can confer protection from atherosclerosis, such as from atherothrombosis (Arehart et al, Curr. Med. Chem., 2007, 14:2161-2169; Stitham et al, Prostaglandins Other Lipid Mediat., 2007, 82:95-108; Fries et al, Hematology Am. Soc. Hematol. Educ. Program, 2005:445-451; Egan et al, Science, 2004, 306:1954-1957; Kobayashi et al, J. Clin. Invest, 2004, 114:784-794; Arehart et al, Circ. Res., 2008, Mar. 6). It has been shown that defective IP receptor signaling appears to accelerate atherothrombosis in humans, i e that an agonist of the IP receptor can confer protection from atherothrombosis in humans (Arehart et al, Circ. Res., 2008, Mar. 6.)

The compounds of the present invention disclosed herein are useful in the treatment of atherosclerosis, and the treatment of the symptoms thereof. Accordingly, in some embodiments, the present invention provides methods for treating atherosclerosis in a patient in need of the treatment, comprising administering to the patient a composition comprising an IP receptor agonist disclosed herein. In further embodiments, methods are provided for treating a symptom of atherosclerosis in a patient in need of the treatment, comprising administering to the patient a composition comprising an IP receptor agonist disclosed herein.

Asthma

Asthma is a lymphocyte-mediated inflammatory airway disorder characterised by airway eosinophilia, increased mucus production by goblet cells, and structural remodeling of the airway wall. The prevalence of asthma has dramatically increased worldwide in recent decades. It has been shown that genetic deficiency of the IP receptor in mice augments allergic airway inflammation (Takahashi et al, Br J Pharmacol, 2002, 137:315-322). It has been shown that an agonist of the IP receptor can suppress not only the development of asthma when given during the sensitization phase, but also the cardinal features of experimental asthma when given during the challenge phase (Idzko et al, J. Clin. Invest., 2007, 117:464-72, Nagao et al, Am. J. Respir. Cell Mol. Biol., 2003, 29:314-320), at least in part through markedly interfering with the function of antigen-presenting dendnuc cells within the airways (Idzko et al., J. Clin. Invest., 2007, 117:464-472; Zhou et al, J. Immunol., 2007, 178:702-710; Jaffar et al., J. Immunol., 2007, 179:6193-6203; Jozefowski et al, Int. Immunopharmacol., 2003, 3:865-878). These cells are crucial for both the initiation and the maintenance phases of allergic asthma, as depletion of airway dendritic cells during secondary challenge in sensitized mice abolished all characteristic features of asthma, an effect that could be completely restored by adoptive transfer of wild-type dendritic cells (van Rijt et al., J. Exp. Med., 2005, 201:981-991). It has also been shown that an agonist of the IP receptor can inhibit proinflammatory cytokine secretion by human alveolar macrophages (Raychaudhuri et al., J. Biol. Chem., 2002, 277:33344-33348). The compounds of the present invention disclosed herein are useful in the treatment of asthma, and the treatment of the symptoms thereof. Accordingly, in some embodiments, the present invention provides methods for treating asthma in a patient in need of the treatment, comprising administering to the patient a composition comprising IP receptor agonist disclosed herein.

In further embodiments, methods are provided for treating a symptom of asthma in a patient in need of the treatment, comprising administering to the patient a composition comprising IP receptor agonist disclosed herein.

Chronic Obstructive Pulmonary Disease

Activation of the IP-receptor may also be beneficial in chronic obstructive pulmonary disease (COPD). Taprostene, an IP-receptor agonist, suppressed the generation of the $CD8^+$ T cell chemoattractants CXCL9 and CXCL10 from human airway epithelial cells in vitro. (Ayer, L. M., S. M. Wilson, S. L. Traves, D. Proud, M. A. Giembycz. 2008. J. Pharmacol. Exp. Ther. 324: 815-826.) Beraprost, an IP-receptor agonist, protected rats against the development of experimental cigarette smoke-induced emphysema, possibly by means of a concerted inhibitory action on alveolar epithelial cell apoptosis, oxidative burden, matrix metalloproteinase expression, and proinflammatory cytokine generation. (Chen, Y., M. Hanaoka, P. Chen, Y. Droma, N. F. Voelkel, K. Kubo. 2009. Am. J. Physiol. 296: L648-L656.)

In further embodiments, methods are provided for treating COPD in a patient in need of the treatment, comprising administering to the patient a composition comprising IP receptor agonist disclosed herein.

Hyperglycemia

Although hyperglycemia is the major cause for the pathogenesis of diabetic complications such as diabetic peripheral neuropathy (DPN), diabetic nephropathy (DN) and diabetic retinopathy (DR), enhanced vasoconstriction and platelet aggregation in diabetic patients has also been implicated to play a role in disease progression (Cameron et al., Naunyn Schmiedebergs Arch. Pharmacol., 2003, 367:607-614). Agonists of the IP receptor promote vasodilation and inhibit platelet aggregation. Improving microvascular blood flow is able to benefit diabetic complications (Cameron, Diabetologia, 2001, 44:1973-1988).

It has been shown that an agonist of the IP receptor can prevent and reverse motor and sensory peripheral nerve conduction abnormalities in streptozotocin-diabetic rats (Cotter et al., Naunyn Schmiedebergs Arch. Pharmacol., 1993, 347:534-540). Further evidence for the beneficial effect of an agonist of the IP receptor in the treatment of diabetic peripheral neuropathy is given by Hotta et al. (Diabetes, 1996, 45:361-366), Ueno et al. (Jpn. J. Pharmacol., 1996, 70:177-182), Ueno et al. (Life Sci., 1996, 59:PL1O5-PL110), Hotta et al. (Prostaglandins, 1995, 49:339-349), Shindo et al. (Prostaglandins, 1991, 41:85-96), Okuda et al. (Prostaglandins, 1996, 52:375-384), and Koike et al. (FASEB J., 2003, 17:779-781).

Evidence for the beneficial effect of an agonist of the IP receptor in the treatment of diabetic nephropathy is given by Owada et al. (Nephron, 2002, 92:788-796) and Yamashita et al. (Diabetes Res. Clin. Pract., 2002, 57:149-161). Evidence for the beneficial effect of an agonist of the IP receptor in the treatment of diabetic retinopathy is given by Yamagishi et al. (Mol. Med., 2002, 8:546-550), Burnette et al. (Exp. Eye Res., 2006, 83: 1359-1365), and Hotta et al. (Diabetes, 1996, 45:361-366). It has been shown that an agonist of the IP receptor can reduce increased tumor necrosis factor-[alpha] (TNF-[alpha]) levels in diabetic patients, implying that an agonist of the IP receptor may contribute to the prevention of progression in diabetic complications (Fujiwara et al, Exp. Clin. Endocrinol. Diabetes, 2004, 112:390-394).

Evidence that topical administration of an agonist of the IP receptor can result in a decrease in intraocular pressure (IOP) in rabbits and dogs and thereby have beneficial effect in the treatment of glaucoma is given by Hoyng et al (Hoyng et al, Invest. Ophthalmol. Vis. Sci., 1987, 28:470-476).

Agonists of the IP receptor have been shown to have activity for regulation of vascular tone, for vasodilation, and for amelioration of pulmonary hypertension (see, e.g., Strauss et al, Clin Chest Med, 2007, 28:127-142; Driscoll et al, Expert Opin. Pharmacother., 2008, 9:65-81). Evidence for a beneficial effect of an agonist of the IP receptor in the treatment of hypertension is given by Yamada et al. (Peptides, 2008, 29:412-418). Evidence that an agonist of the IP receptor can protect against cerebral ischemia is given by Dogan et al. (Gen. Pharmacol., 1996, 27:1163-1166) and Fang et al (J. Cereb. Blood Flow Metab., 2006, 26:491-501).

Anti-Inflammation

Anti-inflammation agents are prescribed for a variety of conditions. For example, in an inflammatory disease they are used to interfere with and thereby reduce an underlying deleterious.

There is evidence that an IP receptor agonist can inhibit inflammation and thus be a potential treatment as an anti-inflammation therapy. It has been shown that an agonist of the IP receptor can inhibit pro-inflammatory cytokine and chemokine (interleukin-12 (IL-12), tumor necrosis factor-[alpha] (TNF-[alpha]), DL-I[alpha], EL-6, macrophage inflammatory protein-1 alpha (MIP-I[alpha]), monocyte chemoattractant protein-1 (MCP-I)) production and T cell stimulatory function of dendritic cells (Jozefowski et al, Int. Immunopharmacol., 2003, 865-878; Zhou et al, J. Immunol., 2007, 178:702-710; Nagao et al, Am. J. Respir. Cell Mol. Biol., 2003, 29:314-320; Idzko et al, J. Clin. Invest., 2007, 117:464-472). It has been shown that an agonist of the IP receptor can inhibit pro-inflammatory cytokine (TNF-[alpha], IL-1/3, EL-6, granulocyte macrophage stimulating factor (GM-CSF)) production by macrophages (Raychaudhuri et al, J. Biol. Chem., 2002, 277:33344-33348; Czeslick et al, Eur. J. Clin. Invest., 2003, 33:1013-1017; Di Renzo et al, Prostaglandin Leukot. Essent. Fatty Acids, 2005, 73:405-410; Shinomiya et al, Biochem. Pharmacol., 2001, 61:1153-1160). It has been shown that an agonist of the IP receptor can stimulate anti-inflammatory cytokine (DL-IO) production by dendritic cells (Jozefowski et al, Int. Immunopharmacol., 2003, 865-878; Zhou et al, J. Immunol., 2007, 178:702-710). It has been shown that an agonist of the IP receptor can stimulate anti-inflammatory cytokine (DL-10) production by macrophages (Shinomiya et al, Biochem. Pharmacol., 2001, 61: 1153-1160). It has been shown that an agonist of the IP receptor can inhibit a chemokine (CCL 17)-induced chemotaxis of leukocytes (CD4<+>Th2 T cells) (Jaffar et al, J. Immunol., 2007, 179:6193-6203). It has been shown that an agonist of the IP receptor can confer protection from atherosclerosis, such as from atherothrombosis (Arehart et al, Curr. Med. Chem., 2007, 14:2161-2169; Stitham et al, Prostaglandins Other Lipid Mediat., 2007, 82:95-108; Fries et al, Hematology Am. Soc. Hematol. Educ. Program, 2005:445-451; Egan et al, Science, 2004, 306:1954-1957; Kobayashi et al, J. Clin. Invest., 2004, 114:784-794; Arehart et al, Circ. Res., 2008, Mar. 6). It has been shown that an agonist of the IP receptor can attenuate asthma (Idzko et al, J. Clin. Invest., 2007, 117:464-472; Jaffar et al, J. Immunol., 2007, 179:6193-6203; Nagao et al, Am. J. Respir. Cell. Mol. Biol., 2003, 29:314-320). It has been shown that an agonist of the IP receptor can decrease TNF-[alpha] production in type 2 diabetes patients (Fujiwara et al, Exp. Clin. Endocrinol. Diabetes, 2004, 112:390-

394; Goya et al, Metabolism, 2003, 52: 192-198). It has been shown that an agonist of the IP receptor can inhibit ischemia-reperfusion injury (Xiao et al, Circulation, 2001, 104: 2210-2215). It has been shown that an agonist of the IP receptor can inhibit restenosis (Cheng et al, Science, 2002, 296:539-541). It has been shown that an agonist of the IP receptor can attenuate pulmonary vascular injury and shock in a rat model of septic shock (Harada et al, Shock, 2008, Feb. 21). It has been shown that an agonist of the IP receptor can reduce the serum levels of TNF-[alpha] in vivo in patients with rheumatoid arthritis, and this is associated with improvement in the clinical course of the disease (Gao et al, Rheumatol. Int., 2002, 22:45-51; Boehme et al, Rheumatol. Int., 2006, 26:340-347).

The compounds of the present invention disclosed herein provide beneficial reduction of inflammation. The compounds of the present invention disclosed herein provide beneficial reduction of a deleterious inflammatory response associated with an inflammatory disease. Accordingly, in some embodiments, the present invention provides methods for reducing inflammation in a patient in need thereof, comprising administering to the patient a composition comprising an IP receptor agonist disclosed herein. In some embodiments, the present invention provides methods for decreasing IL-12, TNF-[alpha], IL-I[alpha], IL-IjS, BL-6, MIP-Ia or MCP-I production in a patient in need thereof, comprising administering to the patient a composition comprising an IP receptor agonist disclosed herein. In some embodiments, the present invention provides methods for decreasing TNF-[alpha] production in a patient in need thereof, comprising administering to the patient a composition comprising an IP receptor agonist disclosed herein. In some embodiments, the present invention provides methods for increasing EL-IO production in a patient in need thereof, comprising administering to the patient a composition comprising an IP receptor agonist disclosed herein. In some embodiments, the present invention provides methods for reducing a deleterious inflammatory response associated with an inflammatory disease in a patient in need thereof, comprising administering to the patient a composition comprising an IP receptor agonist disclosed herein. In some embodiments, the present invention provides methods for treating an inflammatory disease or a symptom thereof in a patient in need of the treatment comprising administering to the patient a composition comprising an IP receptor agonist disclosed herein. In some embodiments, the present invention provides methods for treating an inflammatory disease or a symptom thereof in a patient in need of the treatment comprising administering to the patient a composition comprising an IP receptor agonist disclosed herein. In some embodiments, the present invention provides methods for treating an inflammatory disease or a symptom thereof in a patient in need of the treatment comprising administering to the patient a composition comprising an IP receptor agonist disclosed herein, wherein the inflammatory disease is selected from the group consisting of psoriasis, psoriatic arthritis, rheumatoid arthritis, Crohn's disease, transplant rejection, multiple sclerosis, systemic lupus erythematosus (SLE), ulcerative colitis, ischemia-reperfusion injury, restenosis, atherosclerosis, acne, diabetes (including type 1 diabetes and type 2 diabetes), sepsis, chronic obstructive pulmonary disease (COPD), and asthma.

Fibrosis

PGI2 signaling has been shown to play a beneficial role in fibrotic diseases of various organs, including kidney, heart, lung, skin, pancreas and liver, as well as in systemic sclerosis and associated pathologies. It has been shown that an agonist of the IP receptor can ameliorate cardiac fibrosis (Chan E C et al (2010) *J Mol Cell Cardiol*. April 18; Hirata Y et al (2009) *Biomed Pharmacother.* 63(10):781-6; Kaneshige T et al (2007) *J Vet Med Sci.* 69(12):1271-6). It has been shown that an agonist of the IP receptor can attenuate renal fibrosis (Takenaka M et al (2009) Prostaglandins Leukot Essent Fatty Acids. 80(5-6):263-7). It has been shown that an agonist of the IP receptor can protect against pulmonary fibrosis in a bleomycin model (Zhu Y et al (2010) *Respir Res.* 20; 11(1):34). It has been shown that an agonist of the IP receptor can suppress the production of connective tissue growth factor, a key mediator of fibrosis, in scleroderma patients (Stratton R et al (2001) *J Clin Invest.* 108(2):241-50). It has been shown that an agonist of the IP receptor can reduce the incidence of digital ulcerations in patients with systemic sclerosis M. Vayssairat (1999) *J Rheumatol* 26:2173-2178. It has been shown that an agonist of the IP receptor can reduce fingertip necrosis in infants with refractory Renaud's phenomenon (Shouval D S et al (2008) *Clin Exp Rheumatol*. 26(3 Suppl 49):S105-7). It has been shown that an agonist of the IP receptor can reduce markers of endothelial activation in patients with systemic sclerosis (Rehberger P et al (2009) *Acta Derm Venereol.* 89(3):245-9.). It has been shown that an agonist of the IP receptor can reduce severity, frequency, and duration of Raynaud's attacks in patients with systemic sclerosis (Torlay et al (1991) *Ann Rheum Dis* 50, 800-804). It has been shown that an agonist of the IP receptor can improve portal hemodynamics in patients with systemic sclerosis and Raynaud's phenomenon (Zardi et al (2006) *In Vivo* 20(3):377-80). It has been shown that an agonist of the IP receptor can inhibit the progression of pancreatic fibrosis in obese Zucker rats (Sato et al (2010) *Diabetes* 59(4):1092-100).

The IP receptor agonists disclosed herein provide beneficial anti-fibrotic effects to patients suffering from fibrosis of the kidney, heart, lung, skin, pancreas and liver which can be idiopathic or secondary to chronic inflammation and systemic sclerosis, for example, and are not limited to the indications described above.

In addition, there is substantial evidence that an agonist of the IP receptor can improve kidney function in acute and chronic renal failure. It has been shown that an agonist of the IP receptor can restore kidney function in endotoxemia-related acute renal failure (Johannes T et al (2009) *Crit Care Med.* 37(4):1423-32). It has been shown that an agonist of the IP receptor can improve renal function in a model of renal ischemia/reperfusion injury Sahsivar M O et al (2009) *Shock* 32(5):498-502). It has been shown that an agonist of the IP receptor can prevent contrast agent-induced nephropathy in patients with renal dysfunction undergoing cardiac surgery (Spargias K et al (2009) *Circulation* 3; 120 (18):1793-9.) It has been shown that an agonist of the IP receptor can improve renal function, reduce inflammation and sclerotic changes of the kidney in a model for diabetic nephropathy Watanabe M et al (2009) Am J Nephrol. 2009; 30(1):1-11).

The IP receptor agonists disclosed herein provide beneficial improvement of renal function in patients with acute and chronic kidney injury and nephropathies secondary to dye-contrast agents, ischemia-reperfusion injury, systemic inflammation and diabetes for example, and are not limited to the indications described above.

There is considerable evidence for a causal role of Prostacyclin deficiency in the development of preeclampsia (Mills J L et al (1999) *JAMA* 282: 356-362; Walsh S W (2004) *Prostaglandins Leukot Essent Fatty Acids* 70: 223-232). The administration of an agonist of the IP receptor has been shown to lower blood pressure in a rat model of preeclampsia (Zlatnik M G et al (1999) *Am J Obstet Gynecol.* 180(5):1191-5).

The IP receptor agonists disclosed herein provide beneficial improvement of hemodynamics in patients with preeclampsia.

The IP receptor agonist disclosed herein may provide beneficial treatment of cystic fibrosis.

The IP receptor agonists disclosed herein may provide chemoprevention. Chemoprevention is the practice of using of drugs, vitamins, or nutritional supplements to reduce the risk of developing, or having a recurrence of cancer. Oral iloprost (Ventavis), an analogue of prostacyclin, shows promise as a chemopreventive agent for lung cancer. Data supporting IP receptor agonist chemoprevention was presented by Paul Bunn Jr. MD, who is the executive Director of the International Association for the Study of Lung Cancer at the American Association for Cancer Research 102nd Annual Meeting showed that it significantly improved endobronchial dysplasia in former smokers.

PGI2 agonist, including the compounds of formula I, Ia, II or IIa, are also useful as co-therapeutic agents for use in combination with second agents, such as organic nitrates and NO-donors, such as sodium nitroprusside, nitroglycerin, isosorbide mononitrate, isosorbide dinitrate, molsidomine or SIN-1, and inhalational NO; compounds that inhibit the degradation of cyclic guanosine monophosphate (cGMP) and/or cyclic adenosine monophosphate (cAMP), such as inhibitors of phosphodiesterases (PDE) 1, 2, 3, 4 and/or 5, especially PDE 5 inhibitors such as sildenafil, vardenafil and tadalafil; NO-independent, but haem-dependent stimulators of guanylate cyclase, such as in particular the compounds described in WO 00/06568, WO 00/06569, WO 02/42301 and WO 03/095451; NO- and haem-independent activators of guanylate cyclase, such as in particular the compounds described in WO 01/19355, WO 01/19776, WO 01/19778, WO 01/19780, WO 02/070462 and WO 02/070510; compounds which inhibit human neutrophilic elastase, such as sivelestat or DX-890 (Reltran); compounds inhibiting the signal transduction cascade, such as tyrosine kinase and/or serine/threonine kinase inhibitors, in particular imatinib, gefitinib, erlotinib, sorafenib and sunitinib; compounds influencing the energy metabolism of the heart, for example and preferably etomoxir, dichloroacetate, ranolazine or trimetazidine; antithrombotic agents, for example and preferably from the group comprising platelet aggregation inhibitors, anticoagulants or profibrinolytic substances; active substances for lowering blood pressure, for example and preferably from the group comprising calcium antagonists, angiotensin II antagonists, ACE inhibitors, endothelin antagonists, renin inhibitors, aldosterone synthase inhibitors, alpha receptor blockers, beta receptor blockers, mineralocorticoid receptor antagonists, Rho-kinase inhibitors and diuretics; and/or active substances that modify lipid metabolism, for example and preferably from the group comprising thyroid receptor agonists, inhibitors of cholesterol synthesis, for example and preferably HMG-CoA-reductase inhibitors or inhibitors of squalene synthesis, ACAT inhibitors, CETP inhibitors, MTP inhibitors, PPAR-alpha, PPAR-gamma and/or PPAR-delta agonists, cholesterol absorption inhibitors, lipase inhibitors, polymeric bile acid adsorbers, bile acid reabsorption inhibitors and lipoprotein(a) antagonists, particularly in the treatment of PAH or diseases and disorders such as those mentioned hereinbefore, e.g., as potentiators of therapeutic activity of such drugs or as a means of reducing required dosaging or potential side effects of such drugs.

In particular, an embodiment of this invention is a pharmaceutical combination comprising the compounds of Formula I, Ia, II or IIa or pharaceutical salts thereof and a second agent wherein the second agent is a PDEV inhibitor or neutral endopeptidase inhibitor.

The compounds of Formula I, Ia, II or IIa or pharaceutical salts thereof may be mixed with a second agent in a fixed pharmaceutical composition or it may be administered separately, before, simultaneously with or after the other drug substance.

Accordingly, the invention includes as a further aspect a combination of an IP receptor activity with osmotic agents (hypertonic saline, dextran, mannitol, Xylitol), ENaC blockers, an anti-inflammatory, bronchodilatory, antihistamine, anti-tussive, antibiotic and/or DNase drug substance, wherein the IP receptor agonist and the further drug substance may be in the same or different pharmaceutical composition.

Suitable antibiotics include macrolide antibiotics, e.g., tobramycin (TOBI™).

Suitable DNase drug substances include dornase alfa (Pulmozyme™), a highly-purified solution of recombinant human deoxyribonuclease I (rhDNase), which selectively cleaves DNA. Dornase alfa is used to treat cystic fibrosis.

Other useful combinations of IP receptor agonist with anti-inflammatory drugs are those with antagonists of chemokine receptors, e.g., CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists, such as Schering-Plough antagonists SC-351125, SCH-55700 and SCH-D; Takeda antagonists, such as N-[[4-[[[6,7-dihydro-2-(4-methyl-phenyl)-5H-benzo-cyclohepten-8-yl]carbonyl]amino]phenyl]-methyl] tetrahydro-N,N-dimethyl-2H-pyran-4-amin-ium chloride (TAK-770); and CCR-5 antagonists described in U.S. Pat. No. 6,166,037 (particularly claims 18 and 19), WO 00/66558 (particularly claim 8), WO 00/66559 (particularly claim 9), WO 04/018425 and WO 04/026873.

Suitable anti-inflammatory drugs include steroids, for example corticosteroids. Suitable steroids include budesonide, beclamethasone (e.g. dipropionate), butixocort (e.g. propionate), CHF5188, ciclesonide, dexamethasone, flunisolide, fluticasone (e.g. propionate or furoate), GSK-685698, GSK-870086, LAS40369, methyl prednisolone, mometasone (e.g. furoate), prednisolone, rofleponide, and triamcinolone (e.g. acetonide). In certain preferred embodiments the steroid is long-acting corticosteroids such as budesonide, ciclesonide, fluticasone or mometasone.

Suitable second active ingredients include $\beta_2$-agonists. Suitable $\beta_2$-agonists include arformoterol (e.g. tartrate), albuterol/salbutamol (e.g. racemate or single enantiomer such as the R-enantiomer, or salt thereof especially sulfate), AZD3199, bambuterol, BI-171800, bitolterol (e.g. mesylate), carmoterol, clenbuterol, etanterol, fenoterol (e.g. racemate or single enantiomer such as the R-enantiomer, or salt thereof especially hydrobromide), flerbuterol, formoterol (e.g. racemate or single diastereomer such as the R,R-diastereomer, or salt thereof especially fumarate or fumarate dihydrate), GSK-159802, GSK-597901, GSK-678007, indacaterol (e.g. racemate or single enantiomer such as the R-enantiomer, or salt thereof especially maleate, acetate or xinafoate), LAS100977, metaproterenol, milveterol (e.g. hydrochloride), naminterol, olodaterol (e.g. racemate or single enantiomer such as the R-enantiomer, or salt thereof especially hydrochloride), PF-610355, pirbuterol (e.g. acetate), procaterol, reproterol, salmefamol, salmeterol (e.g. racemate or single enantiomer such as the R-enantiomer, or salt thereof especially xinafoate), terbutaline (e.g. sulphate) and vilanterol (or a salt thereof especially trifenatate. In certain preferred embodiments the $\beta_2$-agonist is an ultra-long-acting $\beta_2$-agonist such as indacaterol, or potentially carmoterol, LAS-100977, milveterol, olodaterol, PF-610355 or vilanterol. A preferred embodiment one of the second active ingredients is indacaterol (i.e. (R)-5-[2-(5,6-diethyl-indan-2-ylamino)-1-hydroxyethyl]-8-hydroxy-1H-quinolin-2-one) or a salt thereof. This is a $\beta_2$-adrenoceptor agonist that has an especially long duration of action (i.e. over 24 hours) and a short onset of action (i.e. about 10 minutes). This compound is prepared by the processes described in international patent applications WO 2000/75114 and WO 2005/123684. It is capable of forming acid addition salts, particularly pharmaceutically acceptable acid addition salts. A preferred salt of (R)-5-[2-(5,6-diethyl-indan-2-ylamino)-1-hydroxyethyl]-8-hydroxy-1H-quinolin-2-one is the maleate salt. Another preferred salt is (R)-5-[2-(5,6-diethyl-indan-2-ylamino)-1-hydroxyethyl]-8-hydroxy-1H-quinolin-2-one acetate. Another preferred salt is (R)-5-[2-(5,6-diethyl-indan-2-ylamino)-1-hydroxyethyl]-8-hydroxy-1H-quinolin-2-one xinafoate.

Suitable bronchodilatory drugs include anticholinergic or antimuscarinic agents, such as aclidinium (e.g. bromide), BEA-2108 (e.g. bromide), BEA-2180 (e.g. bromide), CHF-5407, darifenacin (e.g. bromide), darotropium (e.g. bromide), glycopyrrolate (e.g. racemate or single enantiomer, or salt thereof especially bromide), dexpirronium (e.g. bromide), iGSK-202405, GSK-203423, GSK-573719, GSK-656398, ipratropium (e.g. bromide), LAS35201, LAS186368, otilonium (e.g. bromide), oxitropium (e.g. bromide), oxybutynin, PF-3715455, PF-3635659, pirenzepine, revatropate (e.g. hydrobromide), solifenacin (e.g. succinate), SVT-40776, TD-4208, terodiline, tiotropium (e.g. bromide), tolterodine (e.g. tartrate), and trospium (e.g. chloride). In certain preferred embodiments the muscarinic antagonists is long-acting muscarinic antagonist such as darotropium bromide, glycopyrrolate or tiotropium bromide.

Suitable dual anti-inflammatory and bronchodilatory drugs include dual beta-2 adrenoceptor agonist/muscarinic antagonists such as GSK-961081 (e.g. succinate), and those disclosed in USP 2004/0167167, WO 04/74246 and WO 04/74812.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine, as well as those disclosed in JP 2004107299, WO 03/099807 and WO 04/026841.

Accordingly, the invention includes as a further aspect a combination of IP receptor agonist with agents that inhibit ALK5 and/or ALK4 phosphorylation of Smad2 and Smad3.

Accordingly, the invention includes as a further aspect a combination of IP receptor agonist with second agents that are Rho-kinase inhibitors.

Accordingly, the invention includes as a further aspect a combination of IP receptor agonist with second agents that are tryptophan hydroylase 1 (TPH1) inhibitors.

Accordingly, the invention includes as a further aspect a combination of IP receptor agonist with second agents that are multi-kinase inhibitors, such as imatinib mysilate, Gleevec. Imatinib functions as a specific inhibitor of a number of tyrosine kinase enzymes. It occupies the TK active site, leading to a decrease in activity. TK enzymes in the body include the insulin receptor. Imatinib is specific for the TK domain in the Abelson proto-oncogene, c-kit and PDGF-R (platelet-derived growth factor receptor).

In an embodiment of this invention, the IP receptor agonist of this invention are dosed in combination with a second active agent selected from phosphodiesterase V inhibitors, neutral endopeptidase 1 inhibitors, THP1 inhibitors, multi-kinase inhibitors, endothelin antagonist, diuretic, aldosteron receptor blocker, and endothelin receptor blocker.

In an embodiment of this invention, the IP receptor agonist of this invention are dosed in combination with a second active agent selected from phosphodiesterase V inhibitors, neutral endopeptidase 1 inhibitors, THP1 inhibitors, and multi-kinase inhibitors, such as PDGFR or c-Kit.

In another aspect the invention provides a compound of formula I, Ia, II or IIa, in free form or in the form of a pharmaceutically acceptable salt, for use in the manufacture of a medicament for the treatment of a condition responsive to IP receptor agonist activity, particularly in PAH.

The agents of the invention may be administered by any appropriate route, e.g. orally, e.g., in the form of a tablet or capsule; parenterally, e.g., intravenously; by inhalation, e.g., in the treatment of an obstructive airways disease; intranasally, e.g., in the treatment of allergic rhinitis; topically to the skin; or rectally. In a further aspect, the invention also provides a pharmaceutical composition comprising a compound of formula I, Ia, II or IIa, in free form or in the form of a pharmaceutically acceptable salt, optionally together with a pharmaceutically acceptable diluent or carrier therefor. The composition may contain a co-therapeutic agent, such as an anti-inflammatory, broncho-dilatory, antihistamine or anti-tussive drug as hereinbefore described. Such compositions may be prepared using conventional diluents or excipients and techniques known in the galenic art. Thus oral dosage forms may include tablets and capsules. Formulations for topical administration may take the form of creams, ointments, gels or transdermal delivery systems, e.g., patches. Compositions for inhalation may comprise aerosol or other atomizable formulations or dry powder formulations.

When the composition comprises an aerosol formulation, it preferably contains, e.g., a hydro-fluoro-alkane (HFA) propellant, such as HFA134a or HFA227 or a mixture of these, and may contain one or more co-solvents known in the art, such as ethanol (up to 20% by weight), and/or one or more surfactants, such as oleic acid or sorbitan trioleate, and/or one or more bulking agents, such as lactose. When the composition comprises a dry powder formulation, it preferably contains, e.g., the compound of Formula I, Ia, II or IIa or pharaceutical salts thereof having a particle diameter up to 10 microns, optionally together with a diluent or carrier, such as lactose, of the desired particle size distribution and a compound that helps to protect against product performance deterioration due to moisture, e.g., magnesium stearate. When the composition comprises a nebulised formulation, it preferably contains, e.g., the compound of Formula I, Ia, II or IIa or pharaceutical salts thereof either dissolved, or suspended, in a vehicle containing water, a co-solvent, such as ethanol or propylene glycol and a stabilizer, which may be a surfactant.

Further aspects of the invention include:
  (a) a compound of Formula I, Ia, II or IIa or pharaceutical salts thereof in inhalable form, e.g., in an aerosol or other atomisable composition or in inhalable particulate, e.g., micronised form;
  (b) an inhalable medicament comprising a compound of Formula I, Ia, II or IIa or pharaceutical salts thereof in inhalable form;

(c) a pharmaceutical product comprising a compound of formula (I) in inhalable form in association with an inhalation device; and (d) an inhalation device containing a compound of Formula I, Ia, II or IIa or pharaceutical salts thereof in inhalable form.

Dosages of compounds of Formula I, Ia, II or IIa or pharaceutical salts thereof employed in practicing the present invention will of course vary depending, e.g., on the particular condition to be treated, the effect desired and the mode of administration. In general, suitable daily dosages for administration by inhalation are of the order of 0.005-10 mg, while for oral administration suitable daily doses are of the order of 0.05-100 mg.

Pharmaceutical Use and Assay

Compounds of and their pharmaceutically acceptable salts, hereinafter referred to alternatively as "agents of the invention", are useful as pharmaceuticals. In particular, the compounds are suitable IP receptor agonist and may be tested in the following assays.

Activity of compounds at the IP receptor (IP receptor) is assessed by measuring cAMP accumulation in CHO cells stably expressing the IP receptor (CHO-IP) using the PerkinElmer AlphaScreen assay. This technology measures the endogenous production of cAMP, in a non-radioactive luminescence proximity homogenous assay. A biological reaction occurs between streptavidin coated donor beads, biotinylated cAMP and anti-cAMP acceptor beads, bringing the donor and acceptor beads close enough together so that upon excitation a fluorescence signal is produced. On production of endogenous cAMP, competition between the biotinylated cAMP and cellular-derived cAMP causes a reduction in the fluorescent signal. The reduction in signal is proportional to the amount of cAMP being produced, thus it is possible to quantify the amount of cAMP being produced on stimulation with agonist.

Test and reference compounds are prepared at 100× [final] in 100% DMSO, and diluted 1:3 using a Biomek Fx (Beckman Coulter). This is followed by an intermediate dilution to give 5× [final] in assay buffer (HBSS containing 5 mM HEPES, 0.1% (w/v) BSA). 5 µL of 5× [final] test compounds, reference compounds and buffer/DMSO control are then transferred to a 384-well white OptiPlate, containing 20 µL CHO-IP cell suspension (15,000 cells/well, prepared from frozen), and plate is incubated at room temperature for 1 hour. A cAMP standard curve is constructed for each experiment (concentration range of 10000 nM to 0.001 nM, in assay buffer) and 25 µL of each concentration added to the last two columns of the assay plate. The incubation is terminated by the addition of lysis buffer (dH$_2$O; 0.3% (v v$^{-1}$) Tween-20) containing 20 units mL$^{-1}$ streptavidin coated donor beads and biotinylated cAMP (pre-incubated for 30 minutes) and 20 units mL$^{-1}$ anti-cAMP acceptor beads, which are added to the lysis buffer just before addition to the assay plate. The assay plate is then incubated at room temperature in the dark, for 60 minutes with gentle shaking, and read on the Envision plate reader (Perkin Elmer).

The raw data of the reference compounds, test compounds and controls are converted into cAMP concentrations, using the cAMP standard curve, in GraphPadPrism (GraphPad Software Inc). EC$_{50}$ as well as maximal values of the agonist curves are determined using a 4-parameter logistic equation. The % maximum response values of all test compounds are determined using the top of the treprostinil concentration-response curve.

Compounds of the Examples, herein below, generally have EC$_{50}$ values in the data measurements described above below 5 µM. Table 1 provides a list of representative compounds with their EC$_{50}$ value.

Table 1.

TABLE 1

| Example | EC$_{50}$/µM |
|---------|--------------|
| 1 | 0.000455 |

EXAMPLES

General Conditions

Mass spectra were acquired on LC-MS, SFC-MS, or GC-MS systems using electrospray, chemical and electron impact ionization methods from a range of instruments of the following configurations: Agilent 1100 HPLC systems with an Agilent 6110 Mass Spectrometer, or Micromass Platform Mass Spectrometer or Thermo LTQ Mass Spectrometer; a Waters Acquity UPLC system with SQD Mass Spectrometer, a Waters FractionLynx HPLC system with 3100 Mass Spectrometer, a Waters UPC2 system with TQD Mass Spectrometer or a Waters Prep100 SFC-MS system with SQD2 Mass Spectrometer. [M+H]+ refers to protonated molecular ion of the chemical species. NMR spectra were run on Bruker AVANCE 400 MHz or 500 MHz NMR spectrometers using ICON-NMR, under TopSpin program control. Spectra were measured at 298K, unless indicated otherwise, and were referenced relative to the solvent resonance.

The following examples are intended to illustrate the invention and are not to be construed as being limitations thereon. Temperatures are given in degrees centigrade. If not mentioned otherwise, all evaporations are performed under reduced pressure, preferably between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art. If not defined, the terms have their generally accepted meanings.

Abbreviations br broad
d doublet
dd doublet of doublets
DCM dichloromethane
DMF N,N-dimethylformamide
EtOAc ethyl acetate
h hour(s)
HPLC high pressure liquid chromatography
LCMS liquid chromatography and mass spectrometry
MeOH methanol
MS mass spectrometry
m multiplet
ml milliliter(s)
m/z mass to charge ratio
NMR nuclear magnetic resonance
Rt retention time
s singlet
SCX-2 strong cation exchange (e.g. Isolute® SCX-2 columns from Biotage)
t triplet
THF tetrahydrofuran Referring to the examples that follow, compounds of the preferred embodiments were synthesized using the methods described herein, or other methods, which are known in the art.

The various starting materials, intermediates, and compounds of the preferred embodiments may be isolated and purified, where appropriate, using conventional techniques such as precipitation, filtration, crystallization, evaporation, distillation, and chromatography. Unless otherwise stated, all starting materials are obtained from commercial suppliers and used without further purification. Salts may be prepared from compounds by known salt-forming procedures.

It should be understood that the organic compounds according to the preferred embodiments may exhibit the phenomenon of tautomerism. As the chemical structures within this specification can only represent one of the possible tautomeric forms, it should be understood that the preferred embodiments encompasses any tautomeric form of the drawn structure.

If not indicated otherwise, the analytical HPLC conditions are as follows:
Method 2minLowpHv01
Column: Waters Acquity CSH 1.7 μm, 2.1×50 mm
Temperature: 50° C.
Mobile Phase: A: Water+0.1% Formic Acid B: Acetonitrile+ 0.1% Formic Acid
Flow rate: 1.0 mL/min
Gradient: 0.0 min 5% B, 0.2-1.55 min 5-98% B, 1.55-1.75 min 98% B, 1.75-1.8 min 98-5% B Example 1

7-(6,7-Di-p-tolyl-3,4-dihydro-1,5-naphthyridin-1 (2H)-yl)heptanoic acid

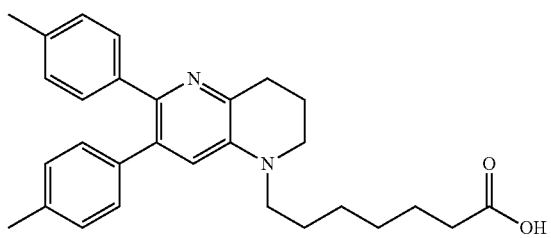 [SMILES: Cc1ccc(-c2cc3c(nc2-c2ccc(C)cc2)CCCN3CCCCCCC(=O)O)cc1]

Step 1: 4-(2-Phenyl-1H-imidazol-1-yl)butanenitrile

A cooled (0° C.) solution of 2-phenyl-1H-imidazole (commercially available) (2.88 g, 20 mmol) in DMF (100 ml) under an atmosphere of nitrogen was treated portionwise with sodium hydride (0.880 g, 22.00 mmol) and allowed to warm to room temperature. After 30 minutes, the mixture was re-cooled to 0° C. and 4-bromobutanenitrile (2.58 ml, 26.0 mmol) was added. After stirring at room temperature under nitrogen overnight, the reaction was quenched with water and extracted with EtOAc. The organic extracts were washed with water, sat. aq. NaHCO$_3$, brine, dried by passing through a phase separating column and concentrated under reduced pressure. The resulting orange/brown oil was purified by flash column chromatography on silica eluting with 0-100% EtOAc in iso-hexane and the product fractions were concentrated under reduced pressure to yield the title compound as a colourless oil.

$^1$H NMR (400 MHz, CDCl$_3$) δ 7.58 (2H, m), 7.47 (3H, m), 7.19 (1H, br s), 7.05 (1H, br s), 4.23 (2H, m), 2.25 (2H, m), 2.05 (2H, m).

Step 2: 4-(2-Phenyl-1H-imidazol-1-yl)butanimidhydrazide

Hydrazine in THF (10.89 ml, 10.89 mmol) was cooled in an ice/water bath and NaH (60%) in mineral oil (0.457 g, 11.43 mmol) was added in 3 portions over 10 minutes. After a further 10 minutes at 0° C., a solution of 4-(2-phenyl-1H-imidazol-1-yl)butanenitrile (step 1) (1.15 g, 5.44 mmol) in THF (10.89 ml) was added. The reaction mixture was allowed to warm slowly to room temperature and after stirring for 2 hours, the reaction was quenched with water (5 ml). The aqueous mixture was extracted with EtOAc (3×) and the combined organic extracts were dried by passing through a phase separating column and concentrated under reduced pressure to afford the title compound. The crude product was used in the next step without further purification.

Step 3: 3-(3-(2-Phenyl-1H-imidazol-1-yl)propyl)-5, 6-di-p-tolyl-1,2,4-triazine

A mixture comprising 4-(2-phenyl-1H-imidazol-1-yl)butanimidhydrazide (step 2)(1.324 g, 5.44 mmol) and 4,4-dimethylbenzil (1.296 g, 5.44 mmol) in EtOH (54 ml) under nitrogen was heated at reflux overnight. The resulting mixture was concentrated under reduced pressure. The crude residue was purified by chromatography on silica eluting with 0-100% EtOAc in iso-hexane and the product fractions were concentrated under reduced pressure to afford the title compound as a yellow oil.
LCMS: Rt=1.97 mins; MS m/z 446.6 [M+H]+; Method 2minLowpH_v01

Step 4: 6,7-Di-p-tolyl-1,2,3,4-tetrahydro-1,5-naphthyridine

A solution of 3-(3-(2-phenyl-1H-imidazol-1-yl)propyl)-5, 6-di-p-tolyl-1,2,4-triazine (step 3) (136 mg, 0.305 mmol) and 2,6-di-tert-butyl-4-methylphenol (67.3 mg, 0.305 mmol) in 1,3,5-triisopropylbenzene (0.75 ml) was heated at 250° C. under nitrogen. After 2 hours, the resulting mixture was allowed to cool to room temperature and loaded onto silica. Purification was carried out by column chromatography eluting with 0-100% EtOAc in iso-hexane. The product fractions were concentrated under reduced pressure and dried in a high vacuum oven to afford the title compound;
LCMS: Rt 0.9 mins; MS m/z 315.5 [M+H]+; Method 2minLowpH_v01

Step 5: Ethyl 7-(6,7-di-p-tolyl-3,4-dihydro-1,5-naphthyridin-1(2H)-yl)heptanoate A suspension comprising 6,7-di-p-tolyl-1,2,3,4-tetrahydro-1,5-naphthyridine (step 4) (43 mg, 0.100 mmol) and ethyl 7-oxoheptanoate (172 mg, 0.998 mmol) in DCM (998 μl) was stirred at room temperature for 30 minutes. To this mixture was added sodium triacetoxyborohydride (106 mg, 0.499 mmol) and stirring continued overnight at room temperature. The resulting mixture was loaded onto silica and purified by column chromatography eluting with 0-100% EtOAc in iso-hexane. The product fractions were concentrated under reduced pressure to yield an orange oil. This oil was loaded onto a pre-wetted (MeOH) Isolute®

SCX-2 cartridge and eluted with 2M NH₃ in MeOH. The product fractions were concentrated under reduced pressure to afford the title compound;

LCMS: Rt 1.19 mins; MS m/z 471.8 [M+H]+; Method 2minLowpH_v01

Step 6: 7-(6,7-Di-p-tolyl-3,4-dihydro-1,5-naphthyridin-1(2H)-yl)heptanoic acid

A solution comprising ethyl 7-(6,7-di-p-tolyl-3,4-dihydro-1,5-naphthyridin-1(2H)-yl)heptanoate (step 5)(45 mg, 0.091 mmol) in EtOH (908 µl) was treated with NaOH (136 µl, 0.272 mmol) and stirred at room temperature for 4 hours. The resulting solution was acidified to pH2 and extracted with EtOAc. The organic extracts were dried by passing through a phase separating column and concentrated under reduced pressure to afford the title compound;

LCMS: Rt 1.13 mins; MS m/z 444.7 [M+H]+; Method 2minLowpH_v01

$^1$H NMR (400 MHz, CDCl₃) δ 7.28 (1H, s), 7.25 (2H, d), 7.11 (4H, m), 7.00 (2H, d), 3.49 (2H, t), 3.43 (2H, m), 3.37 (2H, t), 2.34 (3H, s), 2.32 (2H, m), 2.31 (3H, s), 2.09 (2H, m), 1.63 (4H, m), 1.39 (4H, m).

The invention claimed is:
1. A compound represented by Formula Ia

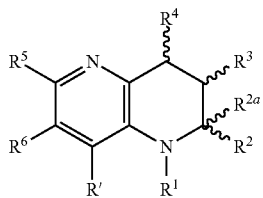

or a pharmaceutically acceptable salt thereof, wherein
R' is H, $C_1$-$C_8$ alkyl optionally substituted by one or more halogen atoms;
$R^1$ is H, $C_1$-$C_8$ alkyl optionally substituted by one or more halogen atoms, $C_1$-$C_4$ alkyl, OH, OR', —NR$^{19}$R$^{21}$, CN or $C_3$-$C_7$ cycloalkyl; or
$R^1$ is —X—Y; or
$R^1$ is —W—R$^7$—X—Y; or
$R^1$ is —S(O)₂—W—X—Y; or
$R^1$ is —S(O)₂—W—R$^7$—X—Y;
$R^2$ is H, $C_1$-$C_8$ alkyl optionally substituted by one or more halogen atoms, $C_1$-$C_4$ alkyl, OH, OR', —NR$^{19}$R$^{21}$, CN or $C_3$-$C_7$ cycloalkyl; or
$R^2$ is —X—Y; or
$R^2$ is —W—R$^7$—X—Y; or
$R^2$ is —S(O)₂—W—X—Y; or
$R^2$ is —S(O)₂—W—R$^7$—X—Y;
wherein either $R^1$ or $R^2$ is —X—Y, —W—R$^7$—X—Y, —S(O)₂—W—X—Y; or —S(O)₂—W—R$^7$—X—Y;
$R^{2a}$ is hydrogen; or
$R^2$ and $R^{2a}$ taken together are oxo;
$R^3$ is H, $C_1$-$C_4$ alkoxy, OH, —NR$^{19}$R$^{21}$, CN, halogen, $C_3$-$C_7$ cycloalkyl or $C_1$-$C_8$ alkyl optionally substituted by one or more halogen atoms;
$R^4$ is H, $C_1$-$C_4$ alkoxy, OH, —NR$^{19}$R$^{21}$, CN, halogen, $C_3$-$C_7$ cycloalkyl or $C_1$-$C_8$ alkyl optionally substituted by one or more halogen atoms;
$R^5$ is $C_1$-$C_8$ alkyl optionally substituted by one or more halogen atoms, $C_1$-$C_4$ alkyl, OH, OR', —NR$^{19}$R$^{21}$, CN or $C_3$-$C_7$ cycloalkyl; $C_1$-$C_8$ alkoxy optionally substituted by one or more halogen atoms; $C_6$-$C_{14}$ aryl; —(C₀-C₄ alkyl)-4 to 14 membered heteroaryl, or —(C₀-C₄ alkyl)-3 to 14 membered heterocyclyl wherein the heteroaryl and heterocyclyl contain at least one heteroatom selected from N, O and S, wherein the aryl, heteroaryl and heterocyclyl are each optionally substituted by one or more Z substituents;
$R^6$ is $C_6$-$C_{14}$ aryl; —(C₀-C₄ alkyl)-4 to 14 membered heteroaryl, —(C₀-C₄ alkyl)-3 to 14 membered heterocyclyl wherein the heteroaryl and heterocyclyl contain at least one heteroatom selected from N, O and S, wherein the aryl, heteroaryl and heterocyclyl are each optionally substituted by one or more Z substituents;
W is $C_1$-$C_8$ alkylene optionally substituted by hydroxy, halogens or $C_1$-$C_4$ alkyl;
X is $C_1$-$C_8$ alkylene optionally substituted by hydroxy, halogens or $C_1$-$C_4$ alkyl;
Y is carboxy, alkoxycarbonyl, tetrazolyl, carbamoyl, monoalkylcarbamoyl, dialkylcarbamoyl, or —CONH—S(O)$_q$—R$^x$, wherein R$^x$ is —$C_1$-$C_4$ alkyl or —NR$^{19}$R$^{21}$,
q is 0, 1 or 2;
$R^7$ is a divalent moiety represented by —O—, —NHC(O)—, —CH₂=CH₂—, —$C_6$-$C_{14}$ aryl-D-; -3 to 14 membered heterocyclyl-D-, wherein the heterocyclyl contains at least one heteroatom selected from N, O and S, wherein D is O, S, NH or not present;
Z is independently OH, aryl, O-aryl, benzyl, O-benzyl, $C_1$-$C_6$ alkyl optionally substituted by one or more OH groups or NH₂ groups, $C_1$-$C_6$ alkyl optionally substituted by one or more halogen atoms, $C_1$-$C_6$ alkoxy optionally substituted by one or more OH groups, $C_1$-$C_6$ alkoxy optionally substituted by one or more halogen, $C_1$-$C_6$ alkoxy optionally substituted by $C_1$-$C_4$ alkoxy, NR$^{18}$(SO₂)R$^{21}$, (SO₂)NR$^{19}$R$^{21}$, (SO₂)R$^{21}$, NR$^{18}$C(O)R$^{21}$, C(O)NR$^{19}$R$^{21}$, NR$^{18}$C(O)NR$^{19}$R$^{21}$, NR$^{18}$C(O)OR$^{19}$, NR$^{19}$R$^{21}$, C(O)OR$^{19}$, C(O)R$^{19}$, SR$^{19}$, OR$^{19}$, oxo, CN, NO₂, halogen or a 3 to 14 membered heterocyclyl, wherein the heterocyclyl contains at least one heteroatom selected from N, O and S;
$R^{18}$ is independently H or $C_1$-$C_6$ alkyl;
$R^{19}$ and $R^{21}$ are each independently H; $C_1$-$C_8$ alkyl; $C_3$-$C_8$ cycloalkyl; alkoxy-$C_1$-$C_4$ alkyl; (C₀-C₄ alkyl)-aryl optionally substituted by one or more groups selected from $C_1$-$C_6$ alkyl, $C_1$-$C_6$ alkoxy and halogen; (C₀-C₄ alkyl)- 3- to 14-membered heterocyclyl, the heterocyclyl including one or more heteroatoms selected from N, O and S, optionally substituted by one or more groups selected from halogen, oxo, $C_1$-$C_6$ alkyl and C(O)$C_1$-$C_6$ alkyl; (C₀-C₄ alkyl)-O-aryl optionally substituted by one or more groups selected from $C_1$-$C_6$ alkyl, $C_1$-$C_6$ alkoxy and halogen; and (C₀-C₄ alkyl)-O-3- to 14-membered heterocyclyl, the heterocyclyl including one or more heteroatoms selected from N, O and S, optionally substituted by one or more groups selected from halogen, $C_1$-$C_6$ alkyl or C(O)$C_1$-$C_6$ alkyl; wherein the alkyl groups are optionally substituted by one or more halogen atoms, $C_1$-$C_4$ alkoxy, C(O)NH₂, C(O)NHC₁-$C_6$ alkyl or C(O)N(C₁-$C_6$ alkyl)₂; or
$R^{19}$ and $R^{21}$ together with the nitrogen atom to which they attached form a 5- to 10-membered heterocyclyl, the heterocyclyl including one or more further heteroatoms selected from N, O and S, the heterocyclyl being optionally substituted by one or more substituents selected from OH; halogen; aryl; 5- to 10-membered heterocyclyl including one or more heteroatoms selected from N, O and S; S(O)₂-aryl; S(O)₂—$C_1$-$C_6$ alkyl; $C_1$-$C_6$ alkyl optionally substituted by one or more halogen atoms; $C_1$-$C_6$ alkoxy optionally substituted by one or more OH groups or $C_1$-$C_4$ alkoxy; and C(O)O$C_1$-$C_6$ alkyl, wherein the aryl and heterocyclyl substituent groups are themselves optionally substituted by $C_1$-$C_6$ alkyl, $C_1$-$C_6$ haloalkyl or $C_1$-$C_6$ alkoxy.

2. The compound according to claim 1, wherein
$R^1$ is —X—Y; or —W—$R^7$—X—Y;
$R^2$ is H, $C_1$-$C_8$ alkyl optionally substituted by one or more halogen atoms, $C_1$-$C_4$ alkyl, OH, or OR';
$R^3$ is H, $C_1$-$C_4$ alkoxy, OH, —$NR^{19}R^{21}$, CN, halogen, $C_3$-$C_7$ cycloalkyl or $C_1$-$C_4$ alkyl optionally substituted by one or more halogen atoms;
$R^4$ is H, $C_1$-$C_4$ alkoxy, OH, —$NR^{19}R^{21}$, CN, halogen, $C_3$-$C_7$ cycloalkyl or $C_1$-$C_4$ alkyl optionally substituted by one or more halogen atoms;
W is $C_1$-$C_6$ alkylene optionally substituted by hydroxy, halogens or $C_1$-$C_4$ alkyl;
X is $C_1$-$C_6$ alkylene optionally substituted by hydroxy, halogens or $C_1$-$C_4$ alkyl;
Y is —C(O)OH, —C(O)O$R^x$, tetrazolyl, carbamoyl, monoalkylcarbamoyl, dialkylcarbamoyl, or —CONH—S(O)$_q$—$R^x$, wherein $R^x$ is —$C_1$-$C_4$ alkyl;
q is 2;
R' is H, $C_1$-$C_4$ alkyl optionally substituted by one or more halogen atoms;
$R^7$ is a divalent moiety represented by —$C_6$-$C_{14}$ aryl-D-; -3 to 14 membered heterocyclyl-D-, wherein the heterocyclyl contains at least one heteroatom selected from N, O and S, wherein D is O; and
$R^{19}$ and $R^{21}$ are each independently H; $C_1$-$C_8$ alkyl.

3. The compound according to claim 1, wherein
$R^1$ is —(CH$_2$)$_m$—C(O)OR", or —(CH$_2$)$_m$—$R^7$—(CH$_2$)$_n$—C(O)OR";
$R^2$ is H, $C_1$-$C_4$ alkyl optionally substituted by one or more halogen atoms;
$R^3$ is H, $C_1$-$C_4$ alkoxy, OH, —$NR^{19}R^{21}$, CN, halogen, $C_3$-$C_7$ cycloalkyl or $C_1$-$C_4$ alkyl optionally substituted by one or more halogen atoms,
$R^4$ is H, $C_1$-$C_4$ alkoxy, OH, —$NR^{19}R^{21}$, CN, halogen, $C_3$-$C_7$ cycloalkyl or $C_1$-$C_4$ alkyl optionally substituted by one or more halogen atoms;
m is 1, 2, 3, 4, 5 or 6;
n is 0, 1, 2 or 3;
R" is H or $C_1$-$C_4$ alkyl optionally substituted by one or more halogen atoms; and
$R^7$ is a divalent moiety represented by —$C_6$-$C_{14}$ aryl-D-; -3 to 14 membered heterocyclyl-D-, wherein the heterocyclyl contains at least one heteroatom selected from N, O and S, wherein D is O.

4. The compound according to claim 1, wherein
$R^5$ is phenyl optionally substituted by OH, $C_1$-$C_4$ alkyl optionally substituted by one or more OH groups or NH$_2$ groups; $C_1$-$C_4$ alkyl optionally substituted by one or more halogen atoms; $C_1$-$C_4$ alkoxy optionally substituted by one or more OH groups or $C_1$-$C_4$ alkoxy; $NR^{19}R^{21}$, C(O)O$R^{19}$; C(O)$R^{19}$; S$R^{19}$; O$R^{19}$; CN; NO$_2$; or halogen; and
$R^6$ is phenyl optionally substituted by OH, $C_1$-$C_4$ alkyl optionally substituted by one or more OH groups or NH$_2$ groups; $C_1$-$C_4$ alkyl optionally substituted by one or more halogen atoms; $C_1$-$C_4$ alkoxy optionally substituted by one or more OH groups or $C_1$-$C_4$ alkoxy; $NR^{19}R^{21}$, C(O)O$R^{19}$, C(O)$R^{19}$, S$R^{19}$, O$R^{19}$, CN, NO$_2$, or halogen.

5. The compound according to claim 1, which is 7-(6,7-Di-p-tolyl-3,4-dihydro-1,5-naphthyridin-1(2H)-yl) heptanoic acid of formula

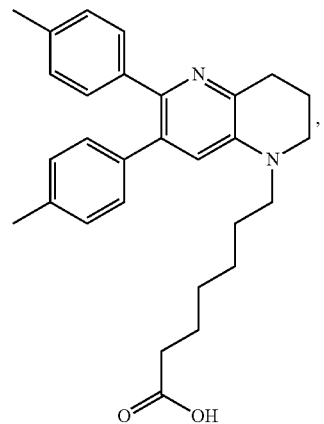 [SMILES: Cc1ccc(-c2cc3c(nc2-c2ccc(C)cc2)CCCN3CCCCCCC(=O)O)cc1]

or a pharmaceutically acceptable salt thereof.

6. A pharmaceutical composition, comprising:
a compound according to claim 1, or a pharmaceutically acceptable salt thereof, and
one or more pharmaceutically acceptable carriers.

7. A pharmaceutical combination, comprising:
a compound according to claim 1, or a pharmaceutically acceptable salt thereof, and a second active agent.

8. A method for the treatment of PAH, disorders in need of antiplatelet therapy, atherosclerosis, asthma, COPD, hyperglycemia, inflammatory disease, or fibrotic diseases in a patient in need thereof, comprising:
administering to the subject in need thereof a therapeutically effective amount of the compound according to claim 1, or a pharmaceutically acceptable salt thereof.

9. A method for the treatment of PAH, asthma, COPD, or cystic fibrosis diseases in a patient in need thereof, comprising:
administering to the subject in need thereof a therapeutically effective amount of the compound according to claim 1, or a pharmaceutically acceptable salt thereof.

* * * * *